United States Patent
Leng et al.

(10) Patent No.: US 11,027,474 B2
(45) Date of Patent: Jun. 8, 2021

(54) FLUIDIC SYSTEMS, DEVICES AND METHODS FOR INDUCING ANISOTROPY IN POLYMERIC MATERIALS

(71) Applicants: THE GOVERNING COUNCIL OF THE UNIVERSITY OF TORONTO, Toronto (CA); BETH ISRAEL DEACONESS MEDICAL CENTRE, INC., Boston, MA (US)

(72) Inventors: Lian Leng, Lasalle (CA); Stephanie Grainger, Stoneham, MA (US); Elliot L. Chaikof, Newton, MA (US); Axel Guenther, Toronto (CA); David Miranda Nieves, Somerville, MA (US); Shashi Malladi, Toronto (CA); Richard Cheng, Toronto (CA)

(73) Assignees: Beth Israel Deaconess Medical Center Inc., Boston, MA (US); The Governing Council of the University of Toronto, Toronto (CA)

( * ) Notice: Subject to any disclaimer, the term of this patent is extended or adjusted under 35 U.S.C. 154(b) by 307 days.

(21) Appl. No.: 15/748,036

(22) PCT Filed: Jul. 22, 2016

(86) PCT No.: PCT/CA2016/050869
§ 371 (c)(1),
(2) Date: Jan. 26, 2018

(87) PCT Pub. No.: WO2017/015750
PCT Pub. Date: Feb. 2, 2017

(65) Prior Publication Data
US 2018/0215088 A1  Aug. 2, 2018

Related U.S. Application Data

(60) Provisional application No. 62/197,405, filed on Jul. 27, 2015.

(51) Int. Cl.
B29C 48/255 (2019.01)
B29C 48/00 (2019.01)
(Continued)

(52) U.S. Cl.
CPC ........ B29C 48/2556 (2019.02); B29C 48/002 (2019.02); B29C 48/022 (2019.02);
(Continued)

(58) Field of Classification Search
CPC ... B29C 48/2556; B29C 48/002; B29C 48/08; B29C 48/022; B29C 48/28; B29C 48/92;
(Continued)

(56) References Cited

U.S. PATENT DOCUMENTS

| | | |
|---|---|---|
| 8,222,049 B2 | 7/2012 | Linder et al. |
| 9,764,505 B2 | 9/2017 | Guenther et al. |

(Continued)

FOREIGN PATENT DOCUMENTS

| | | |
|---|---|---|
| CA | 2378678 A1 | 12/2000 |
| CA | 2856063 A1 | 5/2013 |
| WO | 2012/146458 A2 | 11/2012 |

OTHER PUBLICATIONS

Kim et al., Recellularization of decellularized human adipose-tissue-derived extracellular matrix sheets with other human cell types, 2012, Springer, 348, p. 559-567. (Year: 2012).*

(Continued)

Primary Examiner — Lore R Jarrett
(74) Attorney, Agent, or Firm — Hill & Schumacher

(57) ABSTRACT

Systems, devices and methods are provided for fabricating anisotropic polymer materials. According to various embodiments, a fluidic device is employed to distribute a polymer solution and a flow-confining solution in order to generate a layered flow, where the layered flow is formed such that a polymer liquid sheet is sheathed on opposing (Continued)

sides by flow-confining liquid sheets. The fluidic device includes first and second fluid conduits, where the first fluid conduit receives the layered flow. The second fluid conduit has a reduced height relative to the first fluid conduit, such that the layered flow is constricted as it flows through the second fluid conduit. The construction formed by the second flow conduit causes hydrodynamic focusing, reducing the thickness of the polymer liquid sheet, and inducing molecular alignment and anisotropy within the polymer liquid sheet as it is hardened and as strain is applied during extrusion of the sheet.

50 Claims, 27 Drawing Sheets

(51) Int. Cl.

| | | |
|---|---|---|
| *B29C 48/08* | (2019.01) | |
| *B29C 48/92* | (2019.01) | |
| *C08J 3/24* | (2006.01) | |
| *C08J 5/18* | (2006.01) | |
| *C12N 5/077* | (2010.01) | |
| *B29C 48/28* | (2019.01) | |
| *B29K 105/00* | (2006.01) | |
| *B29K 105/24* | (2006.01) | |
| *C12M 1/00* | (2006.01) | |
| *C12M 3/06* | (2006.01) | |
| *B29L 7/00* | (2006.01) | |

(52) U.S. Cl.
CPC .............. *B29C 48/08* (2019.02); *B29C 48/92* (2019.02); *C08J 3/24* (2013.01); *C08J 5/18* (2013.01); *C12N 5/0661* (2013.01); *B29C 48/28* (2019.02); *B29K 2089/00* (2013.01); *B29K 2105/0073* (2013.01); *B29K 2105/243* (2013.01); *B29K 2995/0044* (2013.01); *B29L 2007/002* (2013.01); *C08J 2389/00* (2013.01); *C08J 2489/00* (2013.01); *C12M 23/16* (2013.01); *C12M 23/20* (2013.01)

(58) Field of Classification Search
CPC ... C08J 3/24; C08J 5/18; C08J 2389/00; C08J 2489/00; C12N 5/0661; B29K 2105/243; B29K 2089/00; B29K 2995/0044; B29K 2105/0073; C12M 23/20; C12M 23/16; B29L 2007/002
See application file for complete search history.

(56) References Cited

U.S. PATENT DOCUMENTS

| | | | |
|---|---|---|---|
| 2004/0238052 A1* | 12/2004 | Karp | B01F 15/0205 137/822 |
| 2010/0022680 A1* | 1/2010 | Karnik | B01F 11/0071 523/105 |
| 2011/0151578 A1 | 6/2011 | Abate et al. | |
| 2016/0068385 A1 | 3/2016 | Chen et al. | |

OTHER PUBLICATIONS

L'Heureux, N. et al., A completely biological tissue-engineered human blood vessel, FASEB J. 12, 47-56 (1998).
Berglund, J.D. et al., A biological hybrid model for collagen-based tissue engineered vascular constructs, Biomaterials 24, 1241-1254 (2003).
Caves, J. M. et al., Fibrillogenesis in Continuously Spun Synthetic Collagen Fiber, Journal of Biomedical Materials Research Part B—Applied Biomaterials, 93B, 24-38 (2009).
Koester, S. et al., An in situ study of collagen self-assembly processes, Biomacromolecules 9, 199-207 (2008).
Lanfer, B. et al., Aligned fibrillar collagen matrices obtained by shear flow deposition, Biomaterials, 29, 3888-3895 (2008).
Lee, P. et al., Microfluidic alignment of collagen fibers for in vitro cell culture, Biomed Microdevices, 8, 35-41 (2006).
Saeidi, N. et al., Molecular crowding of collagen: A pathway to produce highly-organized collagenous structures, Biomaterials, 33, 7366-7374 (2012).
Saeidi, N. et al., Dynamic Shear-Influenced Collagen Self-Assembly, Biomaterials, 30, 6581-6592 (2009).
Lai, E S. et al., Aligned nanofibrillar collagen regulates endothelial organization and migration, Regenerative Medicine, 7, 649-661 (2012).
Cavallaro et al., Biotech. and Biomed. 43, 781-791 (1994).
International Search Report for PCT/CA2016/1050869, dated Feb. 2, 2017.

* cited by examiner

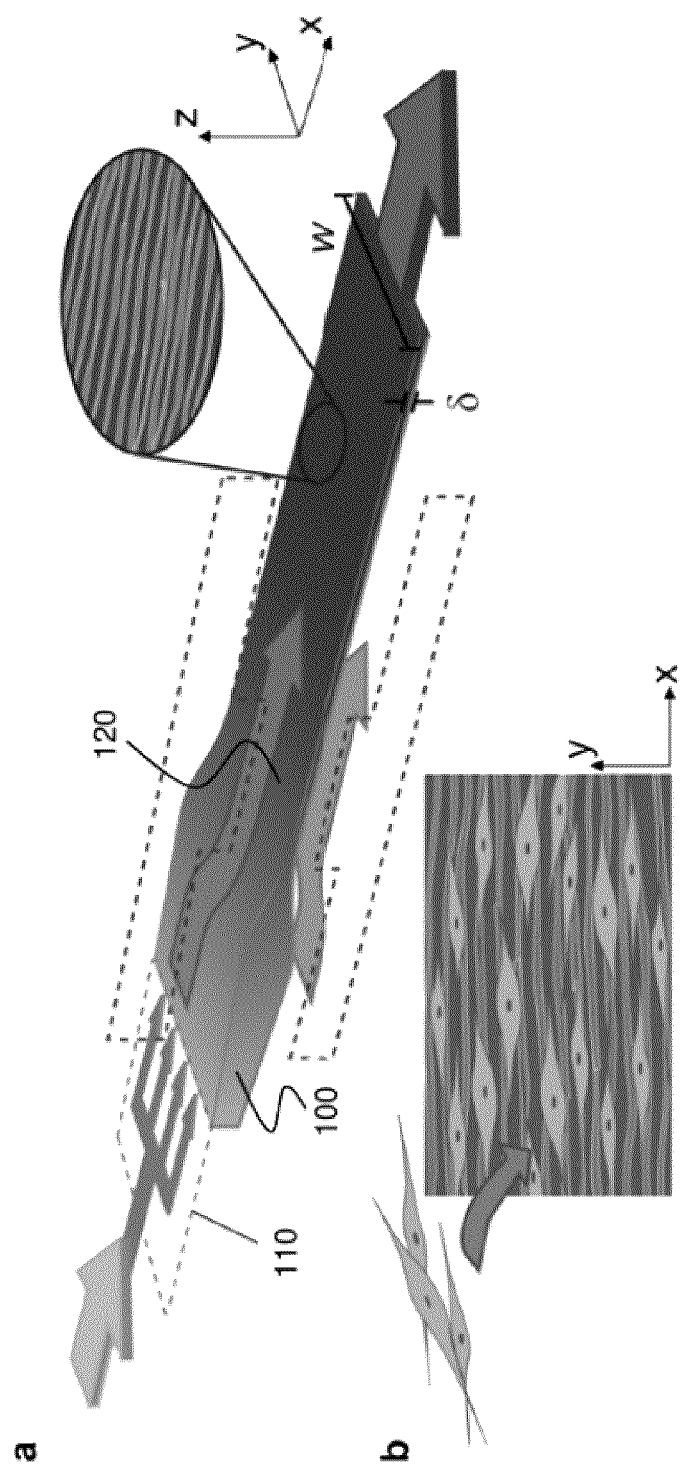
FIGS. 1A-B

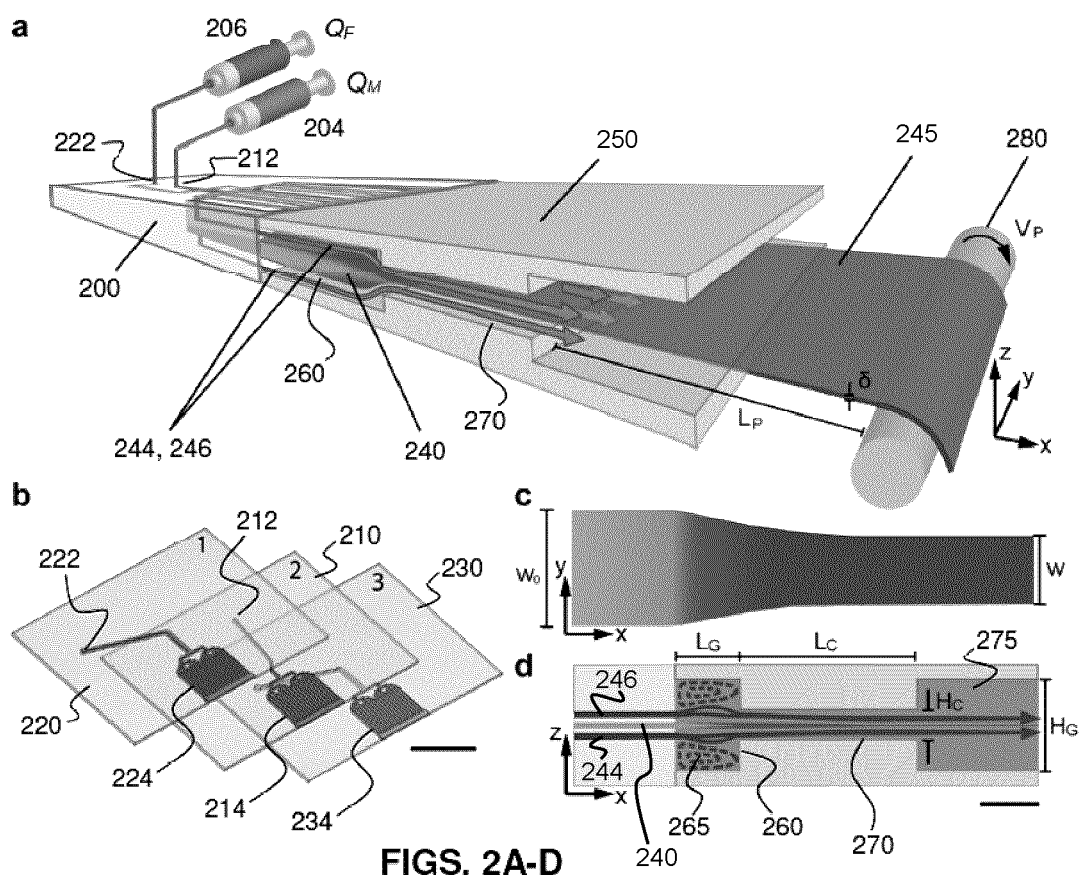
FIGS. 2A-D

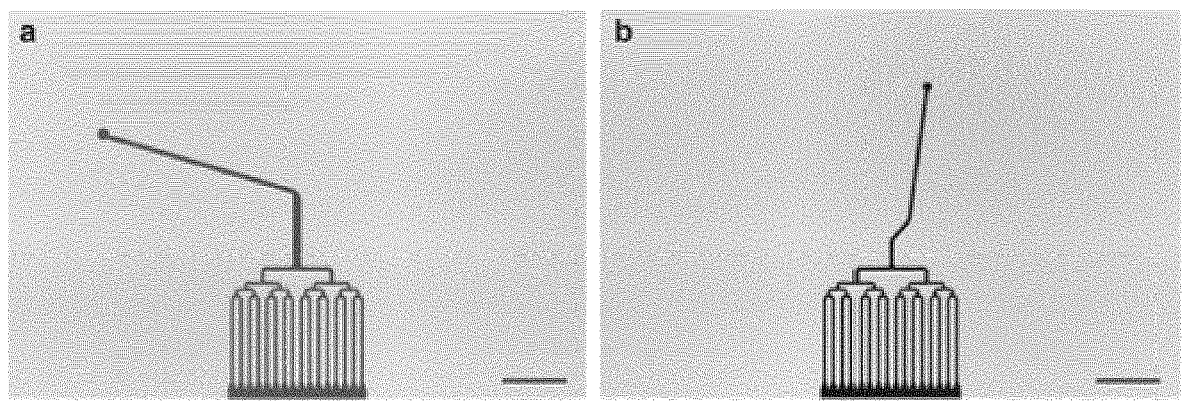
FIGS. 3A-B

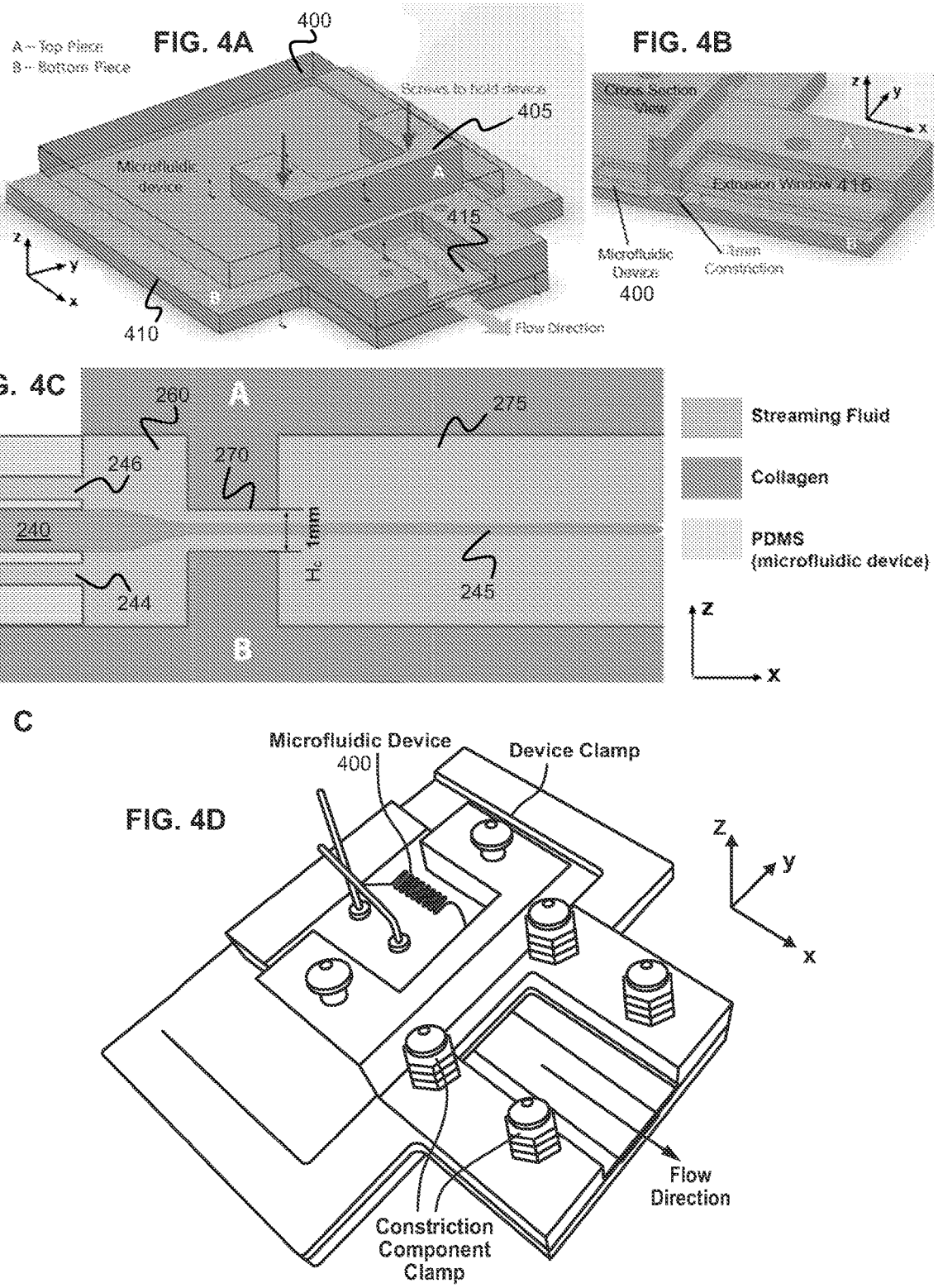

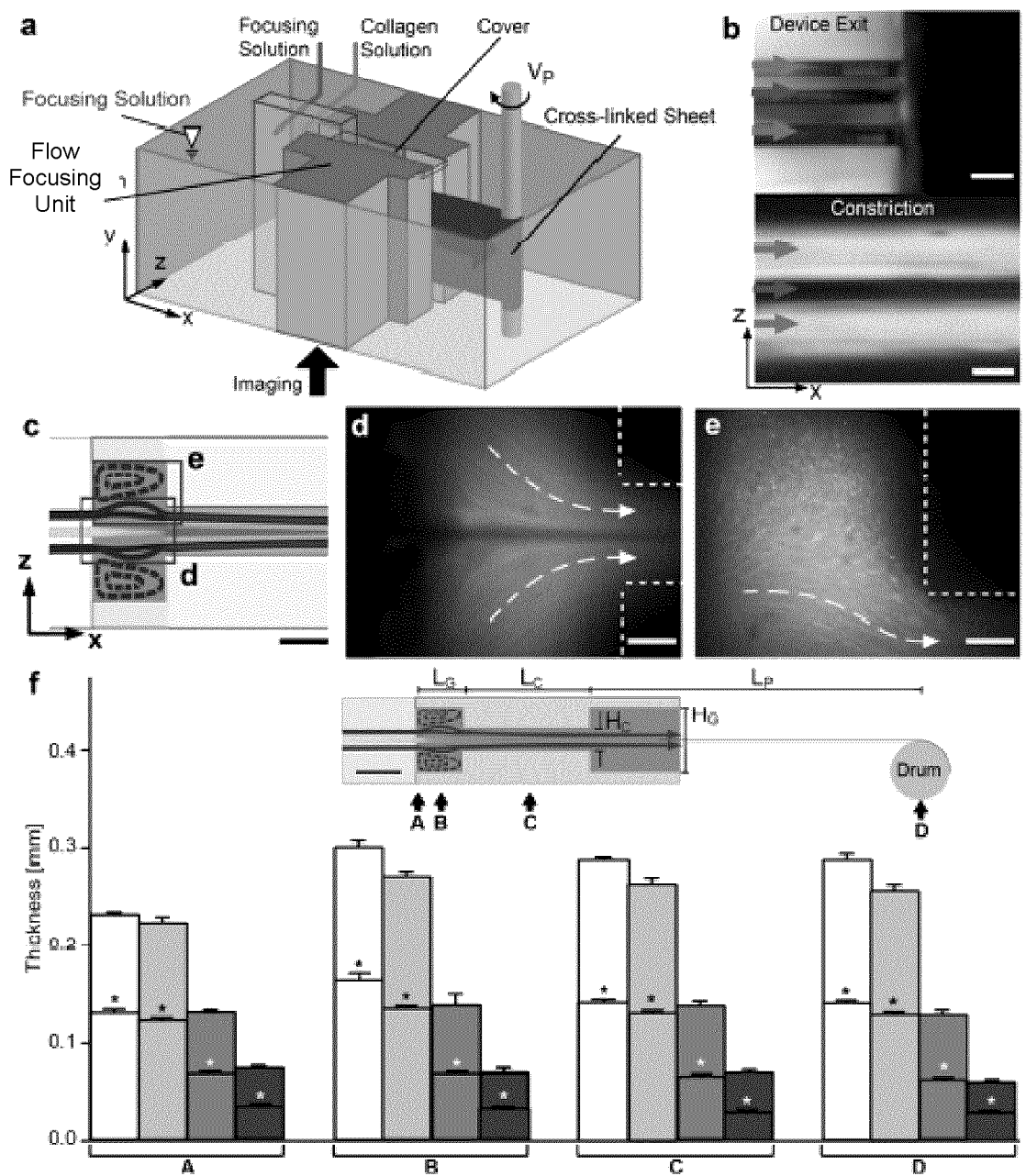
FIGS. 5A-F

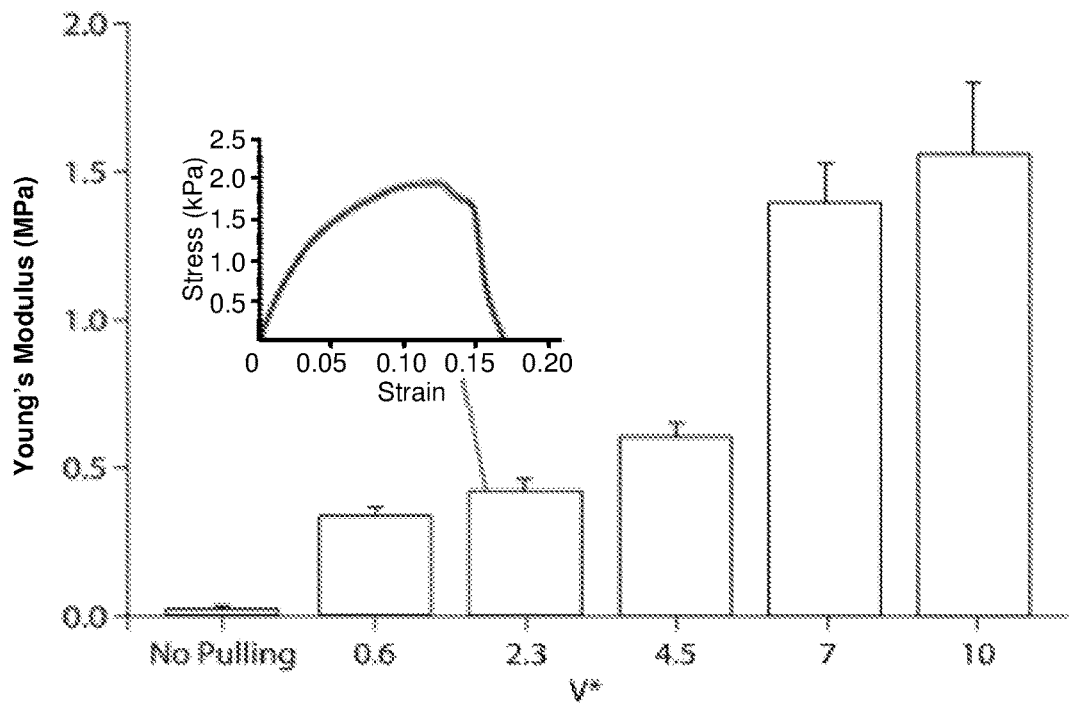
FIG. 8
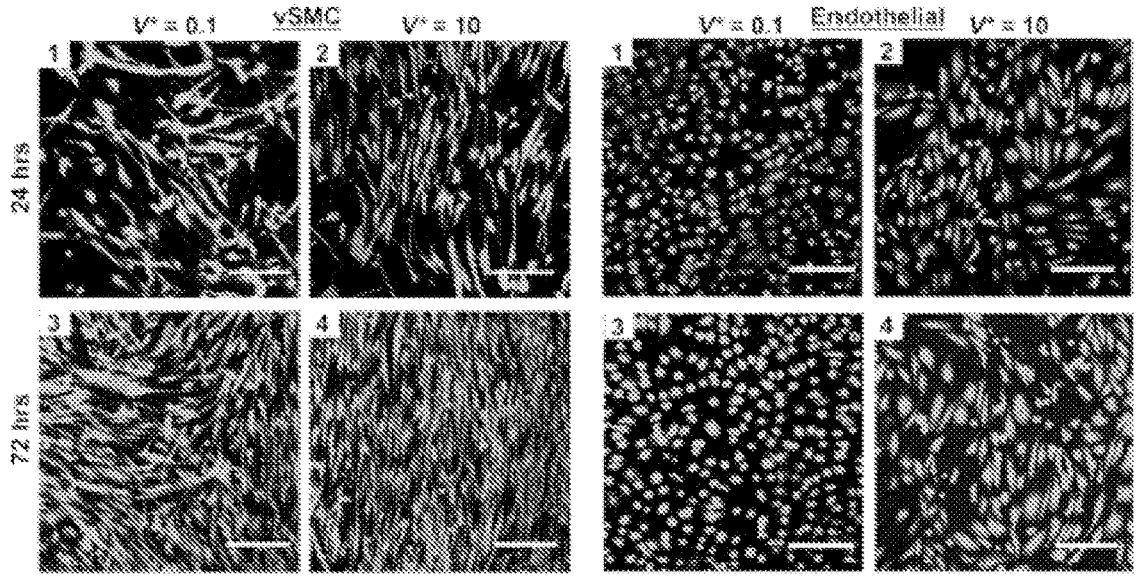
FIG. 9A
FIG. 9B
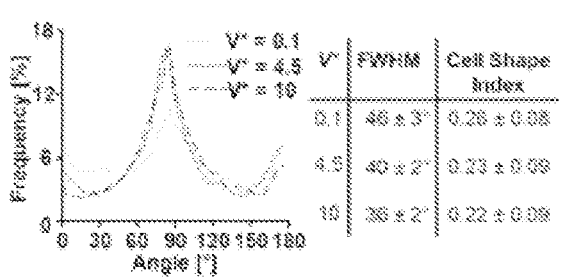
FIG. 9C
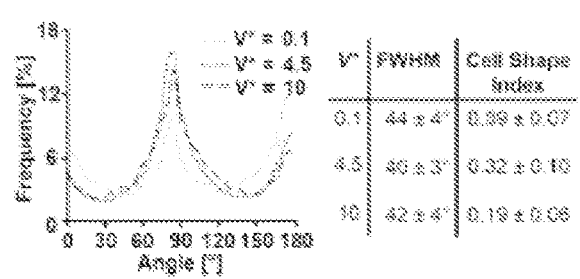
FIG. 9D

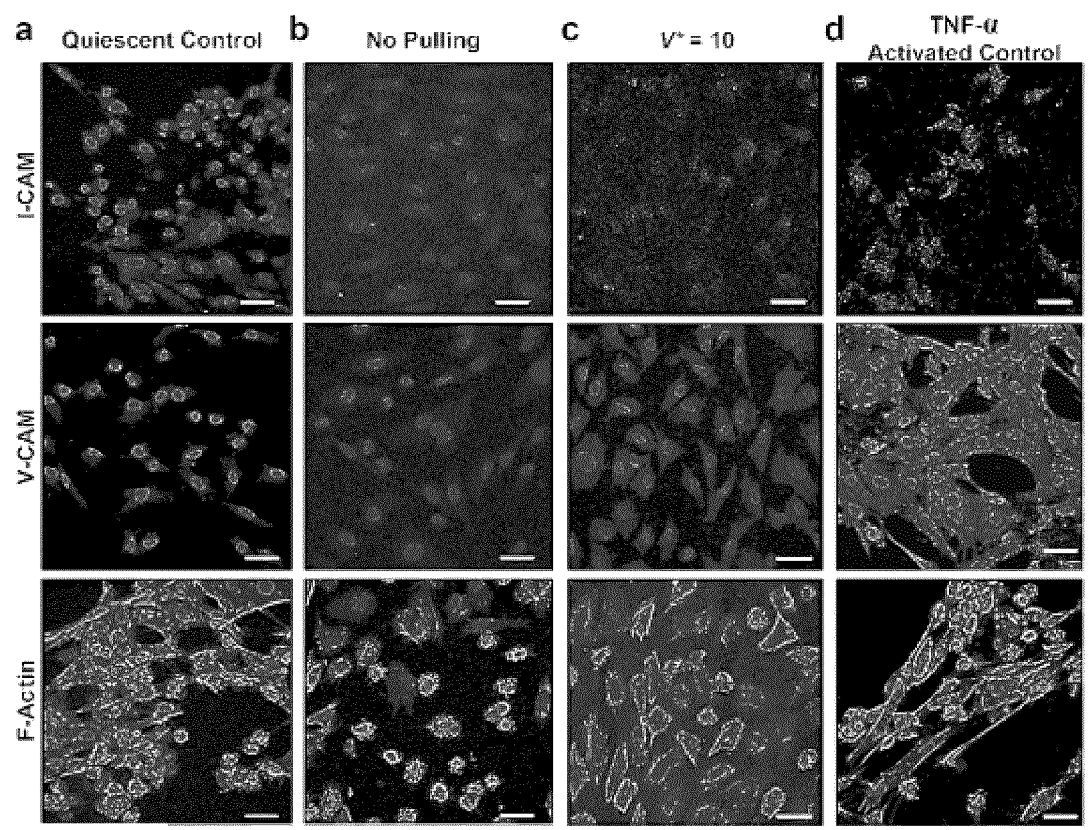
FIGS. 10A-D

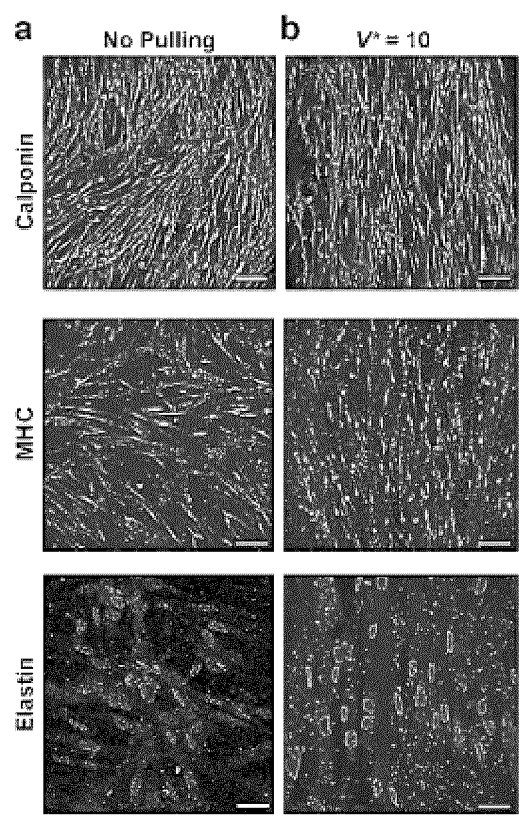
FIGS. 11A-B

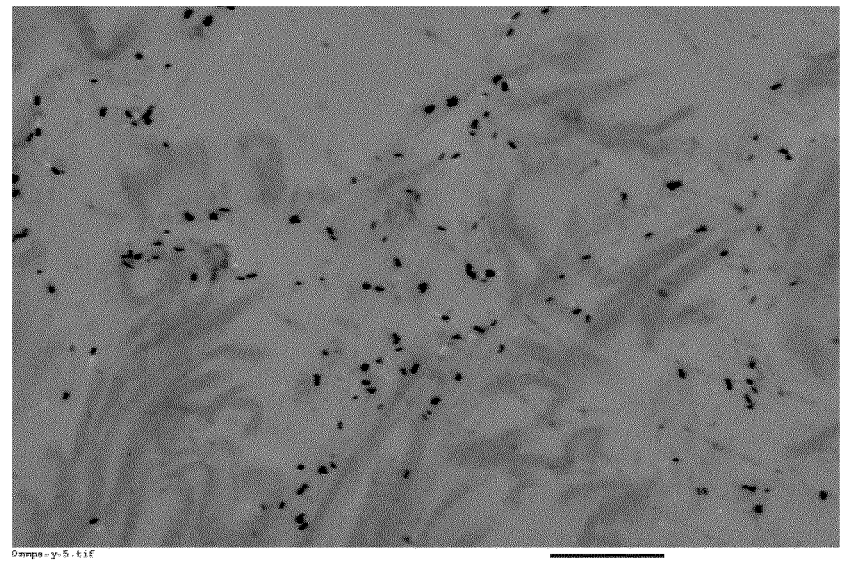
a
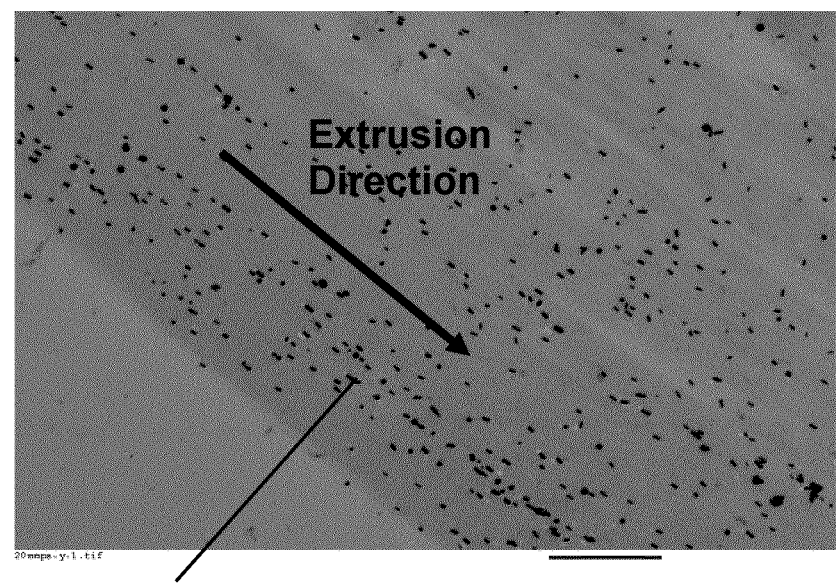
Au Nanorods   b
FIG 12A-B

Tubular Assemblies of aligned Collagen Tubes onto Split Mandrels

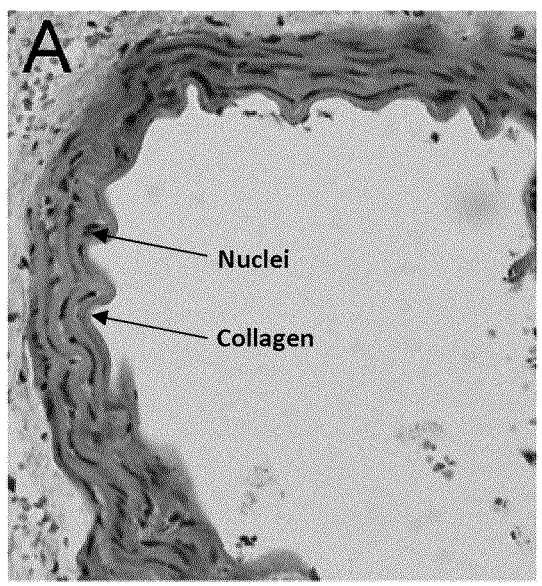 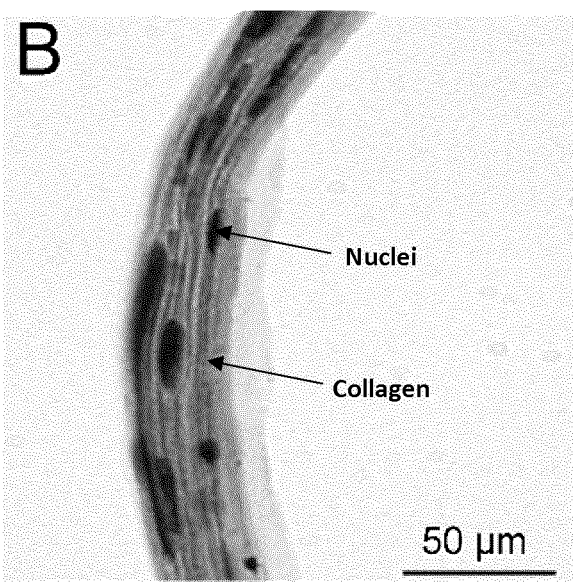
FIG. 14A  FIG. 14B

Formation of Bi-Layered Sheet (Aligned Collagen, SMCs)

Formation of TEBV

FLUIDIC SYSTEMS, DEVICES AND METHODS FOR INDUCING ANISOTROPY IN POLYMERIC MATERIALS

CROSS-REFERENCE TO RELATED APPLICATION

This application is a National Phase application claiming the benefit of the international PCT Patent Application No. PCT/CA2016/050869, filed on Jul. 22, 2016, in English, which claims priority to U.S. Provisional Application No. 62/197,405, titled "FLUIDIC SYSTEMS, DEVICES AND METHODS FOR INDUCING ANISOTROPY IN POLYMERIC MATERIALS" and filed on Jul. 27, 2015, the entire contents of which are incorporated herein by reference.

GOVERNMENT LICENSE RIGHTS

This invention was made with government support under Grant No. HL083867 awarded by the National Institutes of Health. The government has certain rights in the invention.

BACKGROUND

The present disclosure relates to microfluidic methods and devices for the preparation of polymeric structures with anisotropic properties.

High degrees of molecular alignment have been achieved for synthetic polymeric fibers, such as para-aramid ("Kevlar"), polyethylene naphthalate, or polyethylene terathalate fibers using a variety of techniques including the melt spin-draw or liquid isothermal bath processes. Likewise, molecularly aligned fibers composed of biopolymers, such as collagen have been produced by wet spinning and cellulose filaments composed of aligned cellulose nanofibrils have been produced using a microfluidic flow channel [Hakansson K M O, et al. Nature Communications 2014; 5:4018-28]. In contrast, large-scale generation of robust 2-D planar sheets composed of highly aligned biopolymers or synthetic polymers has been difficult to achieve. This has been particularly challenging for the production of planar sheets of aligned collagen.

Nature possesses the unique ability to organize tissues with respect to their cellular and material composition. In plants, animals and humans, biological tissues possess a hierarchical organization of the extracellular matrix with characteristic length scales that often span six orders of magnitude—from macromolecular dimensions to tissue dimensions. In several tissues, a crucial requirement for the multi-scale organization of the extracellular matrix is a high degree of molecular alignment.

A key contributor to achieving the tensile properties of intact tissues is associated with the multiscale organization of collagens that account for 25 to 35% of the total protein mass in mammals and are one of the main constituents of the extracellular matrix (ECM).[2,15] The collagen family consists of 28 different proteins, with type I representing more than 90 wt % of all collagen in humans.[2,15] f Three polypeptide strands or alpha peptides are left-handed helices that form the collagen molecule, a right-handed triple helix with a length of approximately 300 nm and a diameter of 1.5 nm.[17,18] The latter, serves as a monomeric unit, which self-assembles through an entropy-driven process, known as fibrillogenesis, to yield fibrils with diameters between 20 nm and 70 nm that display a 67 nm long D-periodic structure.[2,15] Aligned fibrils subsequently assemble into 10 to 300 nm diameter collagen fibers, which is then organized into a variety of forms. For example, collagen fibers in tendon are aligned parallel to the longitudinal axis. In the stroma of the cornea, collagen types I and V fibrils are arranged as stacked sheets with parallel orientation of fibrils within a layer, but with orthogonal orientation of fibrils between layers.[4,3,5,21] The wall of large arteries contains circumferentially aligned fibers of collagen types I and III.

Controlling multi-scale assembly of collagen in vitro remains a major challenge. The difficulty in consistently promoting high degrees of fibrillar alignment and compactness limit the ultimate tensile strength and Young's modulus attainable in engineered tissues. Collagen gels have been formed with the inclusion of viable cells in culture media at neutral pH. The gels formed are often mechanically weak due to the lack of fibril alignment and require months of culture to allow handling without disruption of the construct.[28,30] Several reports describe attempts to align collagen through shear stress,[31-33,35] tensional forces,[31,36,37] geometric confinement,[38] electric currents,[39] magnetic fields,[40-45] and electrospinning.[1,46-48] Typically these techniques have achieved only limited alignment and packing density of collagen or have otherwise not afforded an approach for the scalable production of robust, free-standing, planar sheets composed of highly aligned collagen fibrils.

SUMMARY

Systems, devices and methods are provided for fabricating anisotropic polymer materials. According to various embodiments, a fluidic device is employed to distribute a polymer solution and a flow-confining solution in order to generate a layered flow, where the layered flow is formed such that a polymer liquid sheet is sheathed on opposing sides by flow-confining liquid sheets. The fluidic device includes first and second fluid conduits, where the first fluid conduit receives the layered flow. The second fluid conduit has a reduced height relative to the first fluid conduit, such that the layered flow is constricted as it flows through the second fluid conduit. The constriction formed by the second flow conduit causes hydrodynamic focusing, reducing the thickness of the polymer liquid sheet, and inducing molecular alignment and anisotropy within the polymer liquid sheet as it is hardened and as strain is applied during extrusion of the sheet.

Accordingly, in a first aspect, there is provided a fluidic device for forming a polymer sheet from a polymer liquid while applying flow construction thereto, comprising:

a polymer distribution fluidic network, wherein a distal portion of said polymer distribution fluidic network is configured to generate a polymer solution liquid sheet when a polymer solution is provided to a proximal inlet of the polymer distribution fluidic network;

a first flow-confining distribution Fluidic network, wherein a distal portion of said first flow-confining distribution fluidic network is configured to generate a first flow-confining liquid sheet when a flow-confining solution is provided to a proximal inlet of the first flow-confining distribution fluidic network;

a second flow-confining distribution fluidic network, wherein a distal portion of said second flow-confining distribution fluidic network is configured to generate a second flow-confining liquid sheet when the flow-confining solution is provided to a proximal inlet of the second flow-confining distribution fluidic network;

wherein said distal portions of said polymer distribution fluidic network, said first flow-confining distribution fluidic network and said second flow-confining distribution fluidic network are arranged in a stacked configuration and are in flow communication with a first flow conduit, such that a layered flow is formed within said first flow conduit, the layered flow comprising the polymer solution liquid sheet, contacted and sheathed on opposing sides thereof by the first flow-confining liquid sheet and the second flow-confining liquid sheet; and a second flow conduit in fluid communication with said first flow conduit, said second flow conduit being configured for flow-focusing of the layered flow, wherein a height of said second flow conduit is smaller than a height of said first flow conduit, such that the layered flow is constricted as the layered flow flows into and through said second flow conduit, wherein the height of said first flow conduit and said second flow conduit is determined in a direction that is perpendicular to the polymer solution liquid sheet.

In another aspect, there is provided a method of forming an anisotropic polymer material, the method comprising:

providing a fluidic device as described above;

flowing the polymer solution into said polymer distribution fluidic network at a first controlled rate;

flowing the flow-confining solution into the first flow-confining distribution fluidic network and the second flow-confining distribution fluidic network at a second controlled rate;

wherein a composition of the polymer solution is selected such that at least an outer portion of the polymer solution liquid sheet is hardened as the polymer solution liquid sheet flows through the second flow conduit, thereby forming a polymer sheet; and collecting the polymer sheet under applied tension, wherein the applied tension and confinement provided by the second flow conduit are selected such that the collected polymer sheet exhibits anisotropic properties.

In another aspect, there is provided a system for forming an anisotropic polymer material, the system comprising:

a fluidic device as described above;

a polymer solution dispensing device in flow communication with said proximal inlet of said polymer distribution fluidic network for providing the polymer liquid thereto at a first controlled flow rate;

a flow-confining solution dispensing device in flow communication with said proximal inlets of said first flow-confining distribution fluidic network and said second flow-confining distribution fluidic network for providing the flow-confining solution thereto at a second controlled flow rate; and a rotating device configured to apply tension to a polymer sheet produced by the fluidic device as the polymer sheet emerges from the fluidic device.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIG. 1A shows an example schematic illustration of the flowable conversion of polymer solution (indicated by the arrow at the left side) to polymer sheets (indicated by the arrow at the right side) with aspect ratios, w/δ, between 15:1 and 375:1, and high degrees of molecular alignment. The illustrated approach involves the uniform lateral distribution of a polymer solution using a microfluidic device, the formation of a layered fluid at the device exit, hydrodynamic focusing of the biopolymer sheet through a constriction, and initiation of fibril formation and cross-linking. Strain is applied on sheet in the axial direction.

FIG. 1B illustrates how macromolecular alignment in the flow direction, x, allows one to tune the macroscopic properties of prepared sheets, such as tensile properties, electrical conductivity, and permeability. The figure also illustrates an example implementation involving the alignment of cells seeded and cultured on or within the prepared sheets.

FIG. 2A is a schematic illustration of an example apparatus consisting of a multi-layer microfluidic device with separate inlets for the polymer solution supplied at volumetric flow rate, $Q_M$, and the two focusing solutions, supplied at volumetric flow rate, $Q_F$. The polymer solution was laterally distributed within the center layer. The two confining solutions were laterally distributed in layers above and below the polymer solution, respectively. At the exit of the microfluidic device, a layered fluid was obtained with the polymer solution at the center bounded by two confining solutions. Solidification of the sheet was initiated and progressed from the planes where the polymer solution was in direct contact with the confining solution. The thickness δ of the layered polymer solution was reduced while passing through a flow focusing unit. The sheet was collected on a rotating collection device, which in this instance is a drum that rotates with velocity, $V_P$, and is located a distance $L_P$=20 mm downstream of the flow-focusing unit.

FIG. 2B provides an exploded view of three microfluidic device layers of the example apparatus (10 mm wide device shown): Layers 1 (top) and 3 (bottom) distribute the confining solutions and center layer 2 distributes the polymer solution. Scale bar is 10 mm.

FIG. 2C illustrates conversion of the polymer solution to a solid polymer sheet in top the view that corresponds to the (x, y) plane in FIG. 1A.

FIG. 2D illustrates polymer sheet formation within the represented flow-focusing unit. Example of machined confinement dimensions are $L_G$=2 mm, $L_C$=6 mm, $H_C$=1 mm, $H_G$=4 mm. Scale bar is 2 mm.

FIG. 2F shows a more detailed rendered engineering design where the temperature difference between T1 and T2 is established using a thermoelectric element mounted below the microfluidic device.

FIGS. 3A-B shows fluidic channel layouts of different planes of an example multilayered microfluidic device. FIG. 3A shows the microchannel layout for distributing the confining solution, while FIG. 3B shows the microchannel layout for distributing the biopolymer solution. The scale bars are 5 mm.

FIGS. 4A-D show an example flow-focusing unit for the formation of thin collagen sheets (e.g. thicknesses below 200 μm). FIGS. 4A and 4B show design drawings of flow-focusing manifold components, FIG. 4C shows cross-section schematic of flow-focusing region on the manifold (1 mm constriction).

FIG. 4D is a photograph of an example microfluidic device that was fabricated using multilayer soft lithography with an attached constriction unit that consisted of two milled aluminum parts. The scale bar is 10 mm.

FIGS. 5A-F illustrates various examples of cross-sectional aspects of polymer sheet formation for a representative flow-focusing unit and rotating collection unit. FIG. 5A provides a schematic illustration of an example apparatus consisting of an example microfluidic device, an example flow-focusing unit, and an example reservoir with optical access from underneath to sheet formation in the (x,z)-plane. The sheet is extruded into the flow-confining solution. FIG. 5B shows bright-field images of collagen sheet formation using the vertically-oriented manifold shown in FIG. 5A. Images were taken at the device exit (top) and within the flow-focusing region (bottom). Flow parameters were $Q_M$=100 μL/min, $Q_F$=1 mL/min, $V^*$=4.5, $w_0$=10 mm. FIG. 5C provides a schematic illustration of the regions (d) and (e), for which fluorescence microscopy images are shown in FIGS. 5D and 5E, respectively. FIG. 5D shows the imaged flow profile at the entrance to the flow-focusing unit, with flow parameters $Q_M$=100 μL/min, $Q_F$=1 mL/min, $V^*$=10. FIG. 5E shows the imaged recirculation zone within the confining solution in the entrance region to the flow-focusing unit, with flow parameters $Q_F$=1 mL/min. Fluorescent microbeads were added to focusing solution at a concentration of 0.08% v/v. FIG. 5F shows the measured sheet thickness, evaluated at four different locations within the flow-focusing focusing unit with example dimensions of $L_G$=2 mm, $L_C$=6 mm, $L_P$=20 mm, $H_C$=1 mm, and $H_G$=4 mm. Data were obtained using the flow parameters $Q_M$=100 μL/min, $Q_F$=0.5 mL/min, $Q_F$=1 mL/min (*), and $V^*$=0.1, 2, 4.5, 10 (light to dark bars). The scale bars are 250 μm (FIG. 5B), 1 mm (FIG. 5C), 500 μm (FIG. 5D, 5E), 2 mm (Insert FIG. 5F).

FIG. 6A presents collagen sheet thickness, obtained using the flow-focusing unit (solid line, $w_0$=5 mm, 10 mm, and 25 mm) and without the flow-focusing unit (dotted line, $w_0$=5 mm). For the 5 mm wide devices, $Q_M$=50 μL/min, $Q_F$=1 mL/min. $Q_M$ and $Q_F$ were varied proportionally with device width.

FIGS. 7A-H shows measurement results that relate the nanoscale organization of collagen to macroscopic properties of the polymer sheets. FIG. 7A shows TEM images of fibrillar alignment in collagen sheets obtained at $V^*$=0 (1) and 10 (2). FIG. 7B displays SEM images of collagen fiber alignment obtained at $V^*$=0 (1), 10 (2). FIG. 7C shows a one-dimensional autocorrelation function that was calculated by evaluating the intensity distribution of a TEM image of a collagen sheet produced at $V^*$=10 along the direction of alignment, x. The distance between the $0^{th}$ and $1^{st}$ peak corresponds to an average spacing of ~6.5 nm. FIG. 7D is a plot showing the absolute fibril spacing in nm quantified by autocorrelation of SEM images of collagen fibers obtained at $V^*$=0.1, 0.6, 4.5, and 10. In the insert, the plot illustrates the degree of compaction quantified as a percent change in fibril spacing in reference to the fibril spacing at $V^*$=0.1. Results were plotted in comparison to the percent change in cross-sectional area obtained in FIG. 6B (insert). FIG. 7E plots the autocorrelation function of a SEM image (insert) showing the repeated banding pattern (D-period) of ~67 nm. FIG. 7F plots the collagen fibril alignment obtained from SEM image processing of sheets for med at $V^*$=0, 0.1, 0.6, and 10. The full width half max (FWHM) values were summarized in the table insert. FIG. 7G plots the measured Young's modulus (E), ultimate tensile strength (UTS), and strain to failure (%) of collagen sheets formed by passing through a constriction and subsequent alignment induced by different values of $V^*$=0.6 to 10. All experiments were conducted with $Q_M$=100 μL/min and $Q_F$=1 mL/min. The scale bars are 200 nm (FIG. 5A), 1 μm (FIG. 5B, 1 left), 500 nm (FIG. 5B, right), 50 nm (FIG. 5B, 2-left), 500 nm (FIG. 5E, insert). FIG. 7H plots Fourier transform infrared (FTIR) spectroscopy data showing the absence of macromolecular crowding agent PEG in the collagen sheet, indicating physical cross-linking between PEG and collagen during the sheet formation process.

FIG. 8 shows the measured Young's modulus (E) for hydrogel sheets that were prepared with 2% w.t. alginate solution (alginic acid sodium salt, Novamatrix, Norway) as the biopolymer solution and sodium chloride as the flow confining solution for different pulling velocities $V^*$. All experiments were conducted with $Q_M$=100 μL/min and $Q_F$=1 mL/min. The Young's modulus increases by more than one order of magnitude by increasing $V^*$ from 0 to 10.

FIGS. 9A-D illustrates the effect of molecular alignment of collagen sheets on cellular alignment and morphologies. In FIG. 9A, images 1 and 2 show vascular smooth muscle cells (vSMCs) cultured on collagen sheets of increasing r over 24 hrs, and images 3 and 4 show vSMCs cultured on collagen sheets of increasing $V^*$ over 72 hrs. In FIG. 9B, images 1 and 2 show endothelial cells (ECs) cultured on collagen sheets of increasing $V^*$ over 24 hrs, and images 3 and 4 show ECs cultured on collagen sheets of increasing r over 72 hrs. FIG. 9C is an analysis of the alignment of vSMCs cultured on collagen sheets of increasing $V^*$ for 72 hrs along with a table of corresponding full width at half maximum (FWHM) values. FIG. 9D is an analysis of the alignment of ECs cultured on collagen sheets of increasing $V^*$ for 72 hrs, along with a table of corresponding full width at half maximum (FWHM) values and the measured cell shape index.

FIG. 9E shows the vasoconstriction and relaxation responses of human vascular SMCs grown on non-aligned (top) and aligned (bottom), 3 µm thick, collagen sheets. FIG. 9F plots the averaged time traces of stress generated by engineered vascular smooth muscle on aligned (V*=4.5; red line, n=6) and non-aligned (V*=0.1; blue line, n=10) collagen sheets. FIG. 9G plots the contraction stress generated in response to vasoconstrictor treatment, basal tone revealed by vasodilator treatment, and the residual stress were calculated from time traces for aligned (V*=4.5) and non-aligned (V*=0.1) collagen sheets (mean±SEM).

FIGS. 10A-D represent images, which confirm that molecular aligned collagen surfaces do not promote endothelial cell activation. FIG. 10A shows serum-starved quiescent ECs without expression of ICAM or VCAM pro-inflammatory markers. FIGS. 10B and 10C show ECs on non-aligned and aligned collagen sheets (V*=10) without expression of ICAM or VCAM. FIG. 10D shows TNF-α activated positive controls. Scale bar=20 µm.

FIGS. 11A-B illustrates expression of smooth muscle cell contractile proteins, calponin and myosin heavy chain (MHC), and elastin. Immunofluorescent staining of vSMCs cultured on non-aligned (FIG. 11A) and highly aligned collagen sheets (FIG. 11B). Scale bars=100 µm for calponin and MHC in FIGS. 11A and 116B.

FIGS. 12A-B show TEM images of extruded collagen sheets containing gold nanorods that were prepared at (A) V*=0 and (B) V*=10. Scale bars are 500 nm.

FIGS. 14A-B demonstrate the fabrication of an engineered living blood vessel. Hematoxylin and eosin stained cross-section of the (A) murine aorta and an (B) engineered blood vessel. A lamellar ultrastructure consistent with alternating layers of SMCs and collagen is observed.

FIG. 15A shows a machined and assembled control unit for vascular bioprinter allowing for the temperature of the printer cartridge to be controlled.

FIGS. 15B-C shows a schematic of a microfabricated printhead (1) for the formation of an aligned collagen sheet (scale bar 15 mm). FIG. 15B shows a schematic of vascular bioprinter that produces an aligned collagen sheet (bottom) onto which SMCs and potentially other biopolymers, such as elastin, are deposited (top). Biopolymer and cell containing solutions (2-5) are controllably supplied to the printhead and the cell-collagen sheet construct deposited onto a collecting drum (6). FIG. 15C shows a schematic of automated transfer of cell-collagen sheet from drum (6) to mandrel (7) for engineered blood vessel formation. FIG. 15D shows rendered 3D design drawings of vascular bioprinter cartridge (to scale). Scale bars are 200 mm (left and right).

FIG. 16A shows a first-generation microfluidic chip, with channel width ranging from 300 to 400 um, dead volume of 0.049 mL, and device footprint of 37.95 mm×40 mm. FIG. 16B shows a second-generation of microfluidic chip, with channel widths obeying Murray's Law, ranging from 250 to 800 um, dead volume of 0.0228 mL, and a device footprint of 46 mm×25 mm. FIG. 16C shows an exploded view of the multi-layered bonding of multiple-layered devices, with each layer being 1 mm in thickness.

DETAILED DESCRIPTION

Figure 2E:
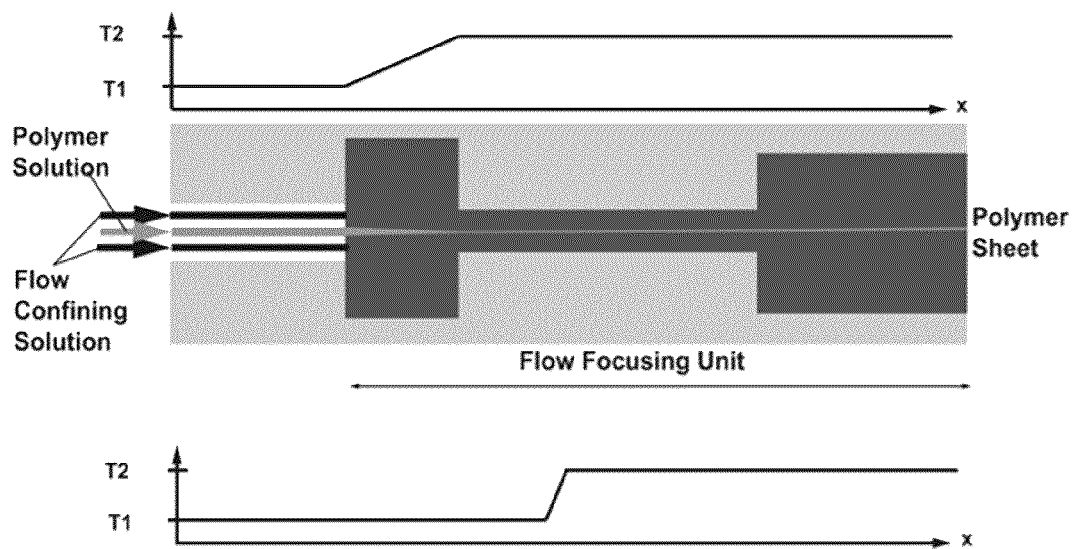
FIGS. 2E and 2F show embodiments of an example flow-focusing unit that promote the temperature-induced conversion of a polymer solution to a polymer sheet. As FIG. 2E illustrates, the microfluidic device, the polymer solution and the confining fluid are kept at temperature, T1. The flow focusing unit, the reservoir, and the rotating collection device are kept at a different temperature, T2.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

As used herein, the phrase "microfluidic channel" refers to fluidic channel, where at least one cross-sectional dimension of the fluidic channel is less than 1 mm.

As used herein, the phrases "mesofluidic channel" and "millifluidic channel" refers to fluidic channel, having cross-sectional dimensions of 1 mm or more, where at least one cross-sectional dimension is between 1 mm and 3 mm.

As used herein, the phrase "nanofiber" refers to a fiber having a diameter less than 1 micron.

As used herein, the phrase "sheet" refers to a polymeric material that has a sheet or ribbon shape. In some embodiments, a sheet has with a lateral width of at least one millimeter and an aspect ratio (sheet width to thickness) of at least 5:1.

As used herein, the phrase "anisotropic polymer sheet" refers to a polymer sheet displaying anisotropy. The anisotropy may by exhibited along an axis that is aligned with the extrusion direction, x, as compared with the longitudinal axis, y, or the normal direction, z, of the polymer sheet.

As used herein, the phrases "polymer liquid", "liquid polymer" and "polymer solution" refer to a liquid that can be solidified to form a solid or hardened material. A polymer solution may include nanoscale objects such as nanobrils, nanofibers and nanoparticles, or may include one or more components that forms such upon polymerization. A polymer solution may consist of polymer molecules in solution and/or monomers that are polymerizable. All components may or may not be subject to cross-linking during the process. As an example of a biopolymer solution, monomeric collagen solution can undergo self-assembly to form collagen fibrils and fibers, which may or may not be subsequently cross-linked. A polymer solution may also include a suspension of nanoscale or microscale particles, such as, but not limited to, nanoparticles, nanorods, nanotubes, nanofibers, flakes of nanosheets, or cells Some example embodiments of the present disclosure are directed to systems, methods and devices that achieve a high degree of molecular alignment in planar polymeric sheets. In some example embodiments, polymeric sheets may be formed with thicknesses such as, but not limited to, of 1 µm to 1 mm, 1 µm to 10 µm, 1 µm to 50 µm, 1 µm to 100 µm, 3 µm to 1 mm, 3 µm to 10 µm, 3 µm to 50 µm, and 3 µm to 100 µm. The polymeric sheets may be uniform in thickness. The width of the polymer sheet may range, for example, from 3 to 40 mm, and an arbitrary length. Molecular alignment may be achieved by a combination of uniform lateral flow distribution of the polymer solution using a microfluidic or millifluidic device in combination with a flow constriction unit. Molecular alignment may induce tunable, non-isotropic properties of the produced polymer sheets, including tensile properties, electrical and thermal conductivity, and permeability. The present disclosure is also concerned with the assembly of such planar materials to "monolithic" three-dimensional objects, including but not limited to stacks of planar materials, tubular constructs and spheroids.

In some embodiments of the present disclosure, a fluidic bioprinter, and methods of use thereof, are described for the continuous formation of polymer sheets having an aligned microstructure through a combination of flow-focusing and strain-induced stretching. As shown in many of the example embodiments provided below, the fluidic bioprinter may be employed to form structurally anisotropic biopolymer sheets, such as biopolymer sheets formed from collagen, where the collagen sheets include oriented, aligned, and close packed, collagen fibers. Such anisotropic polymer sheets have been formed with thicknesses as low as three microns, and lower thicknesses (under three microns) are expected to be readily achievable.

As also shown below, increasing the collagen fibril alignment has been found to correlate with enhanced mechanical properties with preferential alignment of vascular wall cells and physiologically relevant changes in cell shape. The example embodiments provided herein, and variations thereof, in which large scale, microfluidic focusing is employed, affords the fabrication of thin planar collagen sheets with exquisite control over molecular alignment and organization with dramatic effects on material properties.

In some of the examples provided below, aligned collagen sheets are as a tubular form that simulates an arterial wall. Since the arterial wall consists of collagen fibrils organized in a well-defined circumferential and helical alignment, the example embodiments disclosed herein provide an approach to generate living arterial equivalents with a structure that mimics native vessels. The ability to controllably incorporate a wide range of additional structural and soluble proteins, as well as proteoglycans, according to example systems and methods described below, provides the capability to further tailor the biochemical and biomechanical properties of the scaffold.

The present disclosure thus provides devices and methods for the continuous formation of an anisotropic polymer sheet with molecular anisotropy induced by flow-focusing. Referring to FIGS. 1A-B, an illustration is provided that demonstrates the method of forming an anisotropic polymer sheet via alignment induced by a flow-focusing region of a fluidic device. A polymer solution initially forms a non-solidified liquid sheet (stream) 100 using a microfluidic or millifluidic network, which laterally distributes the polymer solution, as shown schematically at 110. Similar distribution (not shown in FIG. 1A) are used to generate flow-confining liquid sheets (streams; not shown in FIG. 1A) that flow above and below the non-solidified, liquid polymer sheet 100. A layered flow is thus generated, consisting of a central sheet of liquid polymer 100, which is sheathed, or otherwise contacted on opposite sides, by flow-confining liquid sheets. Downstream of the formation of the layered flow, the thickness of the central non-solidified liquid polymer sheet 100 is reduced via a flow-focusing region 120, which causes hydrodynamic focusing in the sheet-normal direction.

As shown in FIG. 1B, the flow-focusing of liquid polymer sheet generates and controls macromolecular alignment in the flow direction, x. The figure illustrates an example implementation involving the alignment of cells seeded and cultured on or within the prepared sheets. The flow-focused region may therefore be employed to control one or more macroscopic properties of the solidified polymer sheets, such as tensile properties, electrical conductivity, and permeability, via the control of induced molecular alignment.

Referring now to FIG. 2A, an example fluidic device is shown for producing an anisotropic polymer sheet by flow-focusing and imposed strain. The example apparatus consists of a fluidic device including a multilayer microfluidic region 200, a flow-focusing region 250, and a rotating collecting device 280. The polymer solution and the flow-confining solution are separately delivered, at their respective flow rates, $Q_M$ and $Q_F$, to different layers of the multilayered microfluidic region 200 of the device by a polymer solution dispensing device 204 and a flow-confining dispensing device 206. Non-limiting examples of dispensing devices include syringe pumps, air-displacement pumps, peristaltic pumps, and various other pump mechanisms known to those skilled in the art.

FIG. 2B illustrates an example of a layered structure forming the microfluidic region 200 of the fluidic device. The microfluidic region 200 may be provided as a multi-layered or multi-laminate device, including an intermediate layer 210 having a polymer distribution fluidic network having an inlet port 212 and a distal array of polymer distribution microfluidic channels 214. The distal outputs of the polymer distribution microfluidic channels 214 are arrayed to generate a polymer solution liquid sheet 240 (as shown at 100 and 110 of FIG. 1A).

The multilayered microfluidic region 200 also includes first and second flow-confining fluid distribution layers 220 and 230, each providing a respective flow-confining fluid distribution network. The distal outputs (224 and 234, respectively) of the first and second flow-confining fluid distribution networks are arrayed to generate first and second flow-confining liquid sheets arranged on opposing sides of the central polymer solution liquid sheet. While the present example illustrates an embodiment employing microfluidic channels, it will be understood that in other implementations, one or more of the channels may be mesofluidic channels. In the example embodiment shown, both the first and second fluid flow-confining distribution networks are connected to a common inlet port 222. Although a single flow-confining fluid dispensing device 206 is shown providing a flow-confining solution to both flow-confining fluid distribution networks, it will be understood that separate flow-confining fluid dispensing devices could be employed.

As shown in FIGS. 2A and 2D, the polymer solution liquid sheet 240 and the flow-confining liquid sheets 244, 246 enter a first conduit 260 as a layered flow, where the polymer solution liquid sheet 240 occupies the central region, bounded above and below by flow-confining liquid sheets 244, 246. The layered flow is then guided into a second conduit 270 within the flow-focusing device region 250. The second conduit 270, also referred to herein as a flow-focusing conduit, forms a constriction, such that the height of the second conduit 270 is less than the height of the first conduit 260. The constriction produced by the second (flow-focusing) conduit 270 causes hydrodynamic focusing in the sheet-normal direction, such that the thickness of the central polymer liquid sheet is reduced.

As shown in FIG. 2D, the height of the first conduit 260 may be larger than the initial thickness of the layered flow. This may be beneficial in coalescing fluidic streams to fluid layers, and thereby producing a multi-layered fluid prior to the entering the second (flow-focusing) conduit 270 (as shown in the figure, the flow-confining fluid may form recirculating flows 265 within region 260). Furthermore, a third conduit 275 may be connected to the second conduit, where the height (thickness) of the third conduit is larger than that of the second conduit. This third conduit may be employed to minimize external fluid disturbances during the initial period of sheet formation. In total, regions 260, 270, and 275 form the flow-focusing region 250 of the fluidic device.

The outlet of the flow focusing region may be in flow communication with a reservoir (or channel) filled with a liquid for receiving the emerging polymer liquid sheet 245 (either which may be solidified or partially solidified). The liquid provided within the reservoir may have a composition that is similar to or equal to that of the flow-confining liquid. In one example embodiment, at least the flow-focusing portion 250 of the device may be immersed in such a reservoir.

In at least some embodiments of the present disclosure, the non-solidified, liquid polymer sheet can be configured to be wholly or partially cross-linked during or after it flows through the flow-focusing region or collected onto a rotating collecting device. Cross-linking may be initiated, for example, by contact between the central liquid polymer sheet and the flow-confining liquid sheets. The compaction and straining of the central polymer sheet as it flows through the flow-confining unit 120 followed by cross-linking may be employed to produce an anisotropic cross-linked polymer sheet.

In some example embodiments, the anisotropic polymer sheet may include additional additives such as, but not limited to, organic or inorganic nanoparticles, nanorods, nanotubes, nanofibers, and/or cells that have been added to the polymer solution, where alignment of these additives would be induced as the non-solidified, liquid polymer sheet passes through the flow-focusing region or the fully or partially solidified sheet is collected on the rotating collecting unit. The anisotropic polymer sheet may be formed from a polymer solution containing nanoscale payloads such as, but not limited to nanofibers, nanofibrils or other colloidal nanomaterials. The anisotropic polymer sheet is then formed from cross-linkable or non-cross-linkable polymers. The nanoscale payloads may be themselves physically or chemically bound to each other, or to the polymer matrix they are embedded in. In such an embodiment, the nanofibers may be organic or inorganic nanofibers. In some embodiments, the anisotropic polymer sheet may be formed, at least in part, from fibril forming biopolymers, such as collagen, cellulose, and fibrin. The nanofibers may be formed by fibrillogenesis or molecular self-assembly during processing of the non-solidified, liquid polymer sheet, as described in detail below for the case of collagen.

If so desired, covalent or ionic cross-linking of the polymer solution may also be achieved according to various methods. In many of the illustrative embodiments provided herein, cross-linking may be achieved via contact of the non-solidified, liquid polymer sheet with the flow-confining liquid sheets. For example, in some embodiments, the flow-confining liquid sheets may include a cross-linking species, such as an ionic species, a chemical or photochemical cross-linker, or crosslinking enzymes. The central liquid polymer solution may include polymers or pre-polymers that are cross-linked in the presence of the cross-linking species, such that cross-linking is initiated when the polymer solution contacts the confining fluid within or beyond the flow-focusing region. In other embodiments, the cross-linking of the polymer solution may be induced by other mechanisms, such as through the use of a photo-initiator along with external radiation of the liquid polymer sheet within or beyond the flow-focusing region.

If so desired, the temperature may be controlled within the flow-focusing region, for example, to promote or induce solidification of the liquid polymer sheet. Solidification could be achieved either by lowering the temperature of a polymer melt or by increasing the temperature of a polymer solution above its lower critical solution temperature (LCST).

Figure 2F:
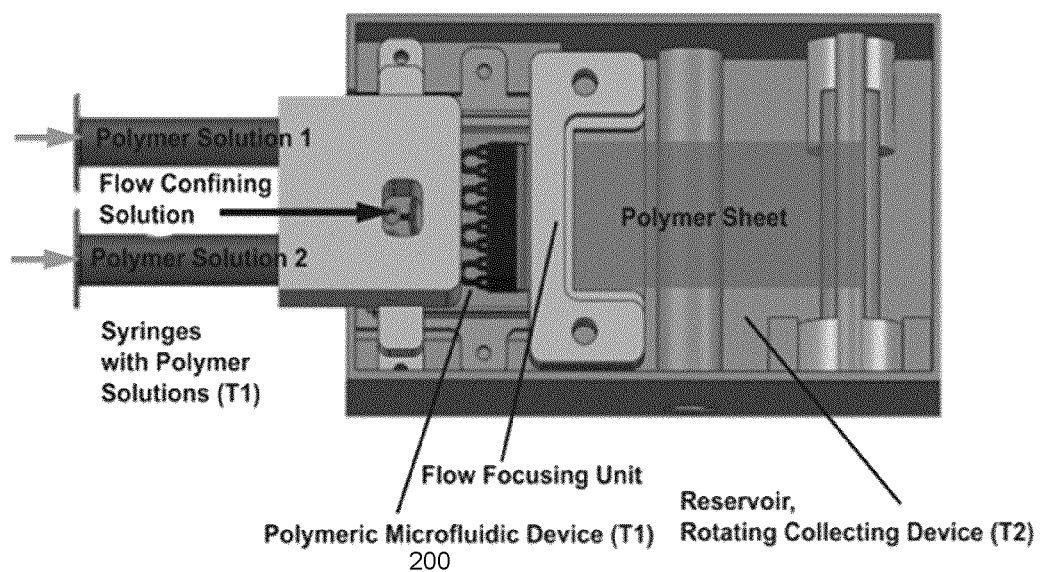

For example, FIGS. 2E and 2F show an illustration of the polymer solution being converted to an aligned polymer sheet by establishing a temperature difference between (i) the temperature of the microfluidic region of the device (T1) and the temperature within and downstream from the flow-focusing region (T2). The narrow distance HC of the flow constriction section of the flow-focusing device (270 in FIG. 2D) allows the temperature change to be rapidly conveyed to the polymer solution.

Depending on the solidification mechanism, the temperature difference may be established such that T1 is lower or higher than T2. An example of the former case is the temperature induced gelation of neutral pH collagen solution delivered at approximately 4° C. and passing through a flow-focusing region that is kept at physiological temperature, 37° C. Temperature induced gelation of elastin and recombinant elastin may be achieved using the same temperature levels. The gelation of agarose and thermoplastic polymers are examples for the latter case.

FIG. 2F shows a rendered engineering design for an example implementation where the temperature difference between T1 and T2 is established by a thermoelectric element. The TE element is located underneath the Polymeric Microfluidic Device 200 (held a temperature T1). This allows the chip and the polymeric solutions to be maintained at the required temperatures.

As shown in FIG. 2A, the emerging polymer liquid sheet 245 may be collected on a collection device, such as a rotating drum 280. The strain applied by the collection device may be employed to achieve further molecular alignment and anisotropy. Although the rotating collecting device in the examples provided below was employed for the dual purpose of collection and strain application, it will be understood that this configuration is provided merely as an illustrative example embodiment for the collection of the anisotropic polymer sheet and the application of strain thereto during its formation. For example, strain could additionally or alternatively be applied (optionally without the use of a collection device) by a modified flow-focusing region unit that contains a constriction section with a gradually decreasing height. Strain would be applied on the polymer layer via a shear stress exerted from the confining streams.

The collection device can take on a wide variety of different forms according to various implementations. The following example embodiments provide three non-limiting example implementations of a rotating collection device. A first example embodiment is a cylindrical mandrel, as shown in the figure, which is rotating around the cylinder axis and may in addition be translated in a direction parallel to the axis. Such a rotating collection device may be configured to collect polymer sheets in a spiral pattern, without overlap in the axial direction, or as a tubular assembly, with overlap in the axial direction.

Figure 2G:
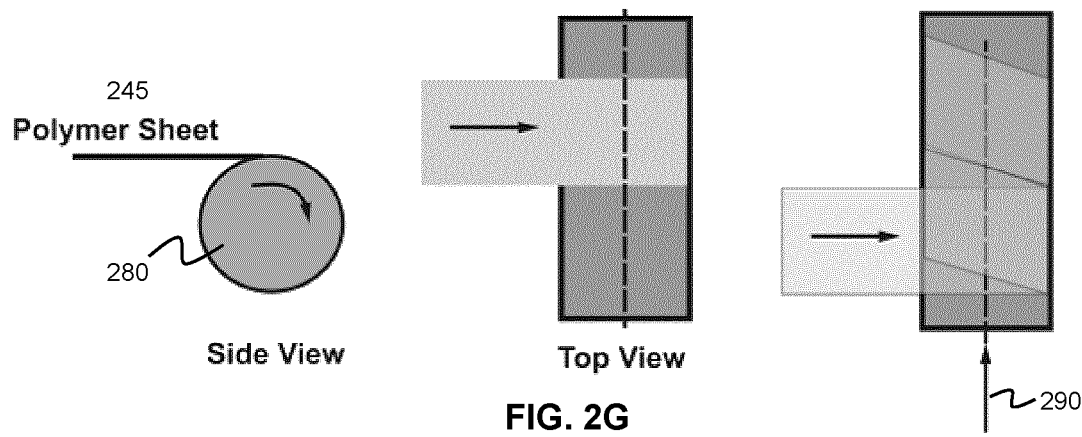
FIG. 2G shows top view and side few illustrations of an example rotating collecting device for the case where the polymer sheet is collected on a cylindrical mandrel.

FIG. 2G shows top and side view illustrations of such an example rotating collecting device, in which the polymer sheet 245 is collected on a cylindrical mandrel 280 (it will be understand that in general, the mandrel cross-section need not be circular in shape). This configuration can be used to collect a polymer sheet under tension on top of itself (i.e. self-overlapping), for example, in the presence of a chemical or physical bond between individual layers. Bonding between layers can occur, for example, due to an on-going polymerization or cross-linking process or a subsequent post-processing step performed on the stack. Accordingly, such an embodiment allows a monolithic tubular assembly with molecular alignment in the circumferential direction to be obtained. Alternatively, as also shown in FIG. 2G, the rotating cylindrical mandrel may be translated such that rolling sheets are collected along the mandrel circumference with partial or no overlap. For example, the mandrel may be translated along the direction of its axis of rotation (or along an oblique angle), as shown at 290. In one example implementation, tubular assemblies with a direction of molecular alignment following a corkscrew pattern may be obtained. In another example implementation, non-overlapping sheets may be obtained, where the sheets may be unrolled after collection and processing.

Figures 2H, 2I:
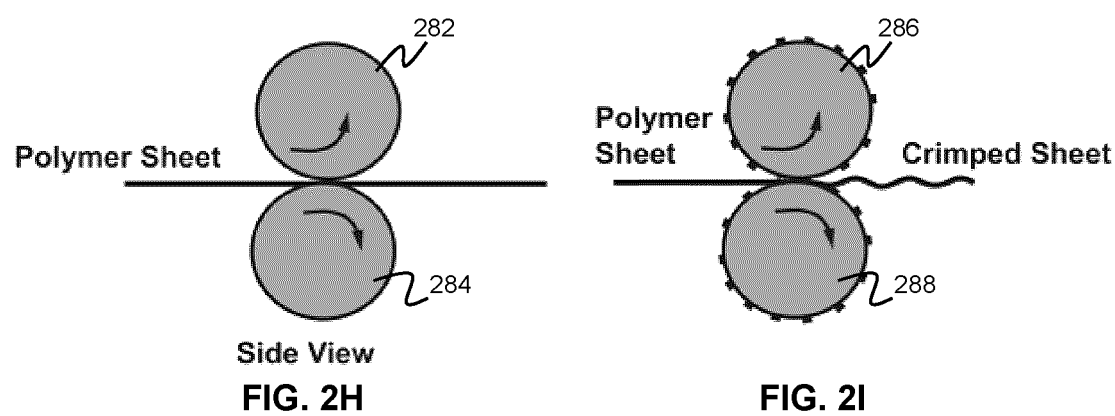
FIG. 2H shows an example embodiment of a rotating collecting device where a polymer sheet passes through two counter rotating drums with smooth surfaces.
FIG. 2I shows an example embodiment of a rotating collecting device where a polymer sheet passes through two counter rotating drums where at least one of the surfaces possesses a microstructured roughness pattern to induce crimping.

A second example embodiment of a collection device is a pair of counter-rotating drums with parallel axes. The polymer sheet is fed in between the two drums, contacting each drum. This configuration could be used not only to apply tension/strain but also by applying a force in the sheet normal direction that may yield further compaction and reduction in sheet thickness. FIG. 2H shows an example embodiment of a rotating collecting device where a polymer sheet passing through two counter rotating drums (284, 284) with smooth surfaces. This configuration allows applying a well-defined strain but does not require the sheet to be rolled or collected on a mandrel (e.g. the sheet could be forwarded for downstream post-processing or collection). FIG. 2I shows an alternative example embodiment of a rotating collecting device where a polymer sheet passes through two counter-rotating cylinders (286, 288) where at least one of the surfaces possesses a microstructured roughness pattern to induce crimping. The polymer sheet may be collected on one of the drums. Alternatively, the polymer sheet, after passing between the two drums, may be collected downstream at an additional rotating collection device, or fed through for downstream in-line processing. By passing the sheet onto a second collection device that has lower tangential velocity than the velocity of the drums of the first collection device crimping may be induced.

Figure 2J:
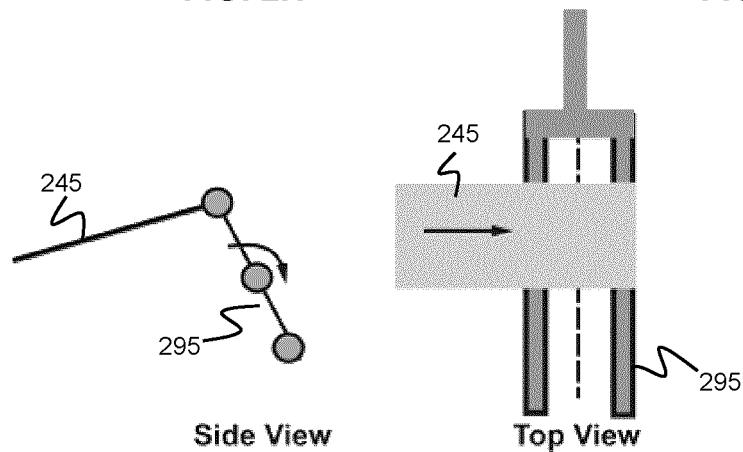
FIG. 2J shows an example embodiment of a rotating collecting device where a polymer sheet is collected on a rotating fork.

A third example embodiment of a collection device is an open frame that is rotating around its axis and may in addition be translated in a direction parallel to the axis. Such a rotating collection device may serves to stack sheets in a planar assembly. FIG. 2J shows an example of such an embodiment, in which a polymer sheet 245 is collected on a rotating fork 295. This configuration may allow the formation, for example, of a planar stack of molecularly aligned sheets.

Figure 2K:
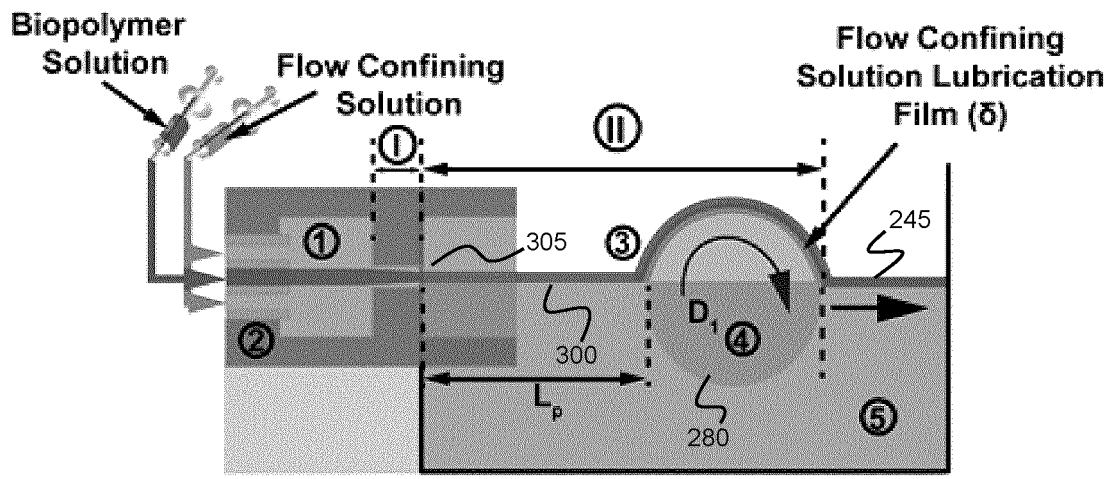
FIGS. 2K-L illustrate an example embodiment in which the polymer sheet, upon emerging from the device, floats on a gas-liquid interface before and after passing over a collection device.

Referring again to FIG. 2A, the emerging 245 polymer sheet is shown wrapped around a rotating collection device that rotates with a velocity $V_P$. In this case the attainable sheet length is limited to $L_P$ and $V_{Sheet}=V_P$. FIG. 2K illustrates an example embodiment in which the collection device has been modified in order to permit the fabrication of longer sheets. As can be seen in FIG. 2K, the reservoir liquid has a surface 300 (gas-liquid interface) contacting the location of the output of the flow-focusing region 305 of the fluidic device, such that the emerging sheet 245 floats on the surface of the reservoir liquid. The emerging polymer sheet 245 is pulled via contact with the rotating collection device 280 (e.g. a cylindrical mandrel), and then continues to float on the liquid surface after passing over the collection device 280. In the case of forming sheets from monomeric collagen, the reservoir liquid may be a solution of 10% w.t. PEG (MW 35 kDa), 4.14 mg/mL monobasic sodium phosphate, 12.1 mg/mL dibasic sodium phosphate, 6.86 mg/mL TES, and 7.89 mg/mL sodium chloride, which promotes continued collagen fibrillogenesis.

It is noted that the velocity at which the sheet is pulled, $V_{Sheet}$, is smaller than $V_P$, for a wide range of V* values. One advantage of this approach is that sheets of length $L>L_P$ can be produced, which can be beneficial in selected applications, such as for the subsequent assembly of the polymer sheets into tissue engineered blood vessels. It is noted that the value of $L_P$ can take on a range of values, and that it may be desirable to use a longer value of $L_P$ in some applications. For example, a value of $L_P$=70 mm was employed by the inventors in one experimental demonstration, and sheets with L=150 mm were produced for assembling tissue engineered arterial substitutes in mouse and rat models. Non-limiting example ranges for the value of LP are 2 mm to 70 mm.

Figure 2L:
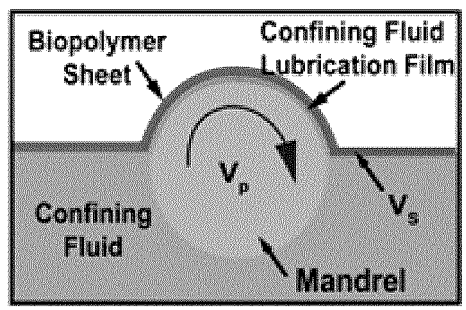
Figure 2M:
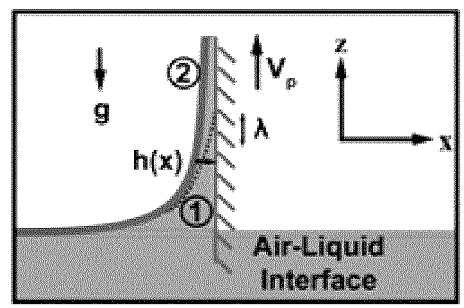
FIG. 2M schematically shows a model of the static and dynamic meniscus formed at the collection device.
Figure 2N:
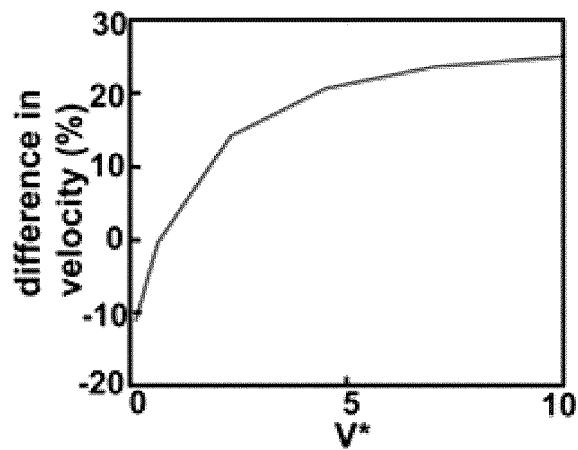
FIG. 2N shows the results predicted by the model.

An analytical model was employed to quantitatively estimate the degree of slippage between the mandrel velocity, $V_P$, and the pulling velocity experienced by the sheet, $V_{sheet}$. FIGS. 2L and 2M schematically show the configuration and parameters of the model, where (1) is the dynamic meniscus region and (2) is the static meniscus region. The model predicts the difference between the sheet and mandrel velocity which is indicative of sheet slippage. (D) Model and experimental prediction of the velocity difference between sheet and collecting device with increasing V*. FIG. 2N shows the results predicted by the model, predicting that the velocity difference between sheet and collecting device increases with increasing V*, and grows to over 20% as V* is increased beyond approximately 5.

As illustrated in the examples below, the anisotropy and thickness of the polymer sheet may be controlled by one or more of the flow rates, $Q_M$ and $Q_F$, as well as the strain applied during collection. For example, in the case of collagen, control over these parameters has produced collagen sheets with thicknesses of 2 to 250 μm, widths of 3 to 17 mm, ultimate tensile strengths of 1.25 to 13 MPa, Young's moduli of 1.3 to 130 MPa and strains to failure of 15 to 35%.

A non-dimensionalized velocity parameter, V*, may be employed to provide a parameter associated with the shear stress induced by the flow focusing unit and mechanical strain induced by the collecting device. This parameter is obtained by relating the pulling velocity with the total velocity of the working fluids and is quantified as $V^*=(V_P-V_{Total})/V_{Total}$, where $V_{Total}=(Q_F+Q_M)/A_{Const}$, and the cross-sectional area at the site of constriction $A_{Const}=W \times H_C$. The inventors have found that the anisotropic molecular and nanoparticle alignment is associated with V*. In various example implementations, the flow and strain parameters may be selected such that V* is greater than 2, greater than 3, greater than 4, or greater than 5.

The example embodiment shown in FIGS. 2A-D employs a microfluidic device 200 for forming the layered flow and a flow-focusing unit 250. In one example implementation, these components may be formed as separate components that are attached or connected. In another example implementation, these components may be integrated into a single device, such as a single multilayer device, with at least a portion of the flow-focusing region integrated with at least a portion of the microfluidic device (see, for example, Example 9 described below). It will also be understood that the flow-focusing unit may employ microfluidic and/or macrofluidic channels.

As described in detail below, in some embodiments, the liquid polymer sheet may be formed from a collagen solution and the flow-confining solutions be provided as a buffered PEG solution. Both hydrodynamic flow-focusing and strain-induced pulling serve to molecularly align collagen within the sheet. The sheet can be collected on the rotating collection device and may be further processed, as desired. As the collagen and flow-confining solutions meet at their common interface, the composition of the confining fluid, for example 10% w/v PEG at pH 8, initiates fibrillogenesis of collagen. Such manipulation of the material structure results in the formation of collagen sheets with a wide range of mechanical properties directly linked to the degree of molecular alignment and fiber packing density induced by the flow-focusing region 250 of the device. As described in the examples provided below, the onset of sheet formation was observed within the flow-focusing unit as the collagen solution comes in contact with the PEG solution. The degree of molecular alignment and packing density of collagen fibers were dependent on both the flow-focusing region, the employed flow rates and the strain imposed by the rotating collecting device 280.

In one non-limiting embodiment, the polymer solution may be an acidic solution of collagen, and the flow-focusing liquid may be a polyethylene glycol (PEG) solution, such that collagen fibrillogenesis is induced in the flow direction and a collagen sheet is generated. Anisotropy is further enhanced by the application of strain to the emerging solid collagen sheet, when collecting it onto a drum or other collection device at a location downstream of the flow-focusing region. It is noted that in 1994, Cavallaro et al. produced collagen threads by extrusion of native, acid-extracted bovine collagen into a buffered solution bath of polyethylene glycol, followed by treatment in a rinsing bath, alcohol bath, air drying, and subsequent collection on a spool.[57] Following this observation, others have utilized a similar approach that involves a multi-step process of serial incubation baths to generate collagen threads and microfibers[56,58-60]. In contrast to these methods for thread formation, the present example embodiments that employ a flow-focusing region for the controlled generation of anisotropy enable the formation of robust anisotropic collagen sheets.

In the examples provided below, it is shown that the present methods when applied to the formation of anisotropic collagen sheets, produce anisotropic collagen sheets with changes in tensile properties that are directly related to the degree of fibril alignment and packing density within the sheet. The scalability of this approach is demonstrated by forming meter-long highly aligned collagen sheets of very large aspect ratio, defined by the ratio of sheet width to thickness, for example, of between 5:1 and 400:1. In addition to the influence of molecular alignment of sheet mechanical properties, aligned collagen sheets induce aligned orientation of endothelial and smooth muscle cells, which is a useful property for tissue engineering. In the examples provided below that involve the formation of collagen sheets, the flow-focusing region was found to be critical for the formation of collagen sheets that were sufficiently robust to be manipulated for collection on a rotating collecting device (as shown in the examples provided below). In the absence of a flow-focusing region, a very weak, gelled collagen sheet is produced that is not sufficiently strong to be handled.

Aligned sheets could be directly delivered from the combined microfluidic device and modified flow-focusing region into wells of multi-well plates, or organ-on-a-chip devices for culture and functional assessment.

Examples of payloads that could be integrated within collagen sheets (or other types of anisotropic polymer sheets) include different types of mammalian cells, bacteria, extracellular matrix molecules and factors that promote cell attachment and/or proliferation and/or migration, drugs, growth factors, proteoglycans, as well as conducting, insulating or semiconducting nanoparticles, stimulus responsive nanoparticles, and organic or semiconductor-nanocrystal based fluorescent labels.

The example embodiments disclosed herein may be employed for a wide range of applications and uses. For example, the devices and methods disclosed herein may be employed for the controlled organization of structures on nanoscale, mesoscale and macro length scales, for the engineering of tissue substitutes, bio-hybrid devices, polymer-based electronics, soft robotics, or other applications.

For example, non-cell containing aligned collagen sheets may be used as tissue constructs in applications such as, but not limited to, vascular grafts, heart patches, tissue engineered aortic valves, as well as skin substitutes. In the latter case, a highly aligned collagen layer may provide an effective replacement of epithelial barrier function against water loss and bacterial infiltration.

In some of the clinically used collagen based skin grafts, such as those produced by Integra Biosciences, barrier function is achieved by a thin layer of silicone that needs to be removed with a separate procedure. In contrast, using the methods described according to the embodiments provided herein, a collagen based bi-layered graft may be produced where the top layer consists of highly aligned and dense, thin collagen layer and the bottom layer of a highly porous collagen layer.

As explained below in Example 11, the two layers may be assembled in a two-step process. In the first step, the aligned and dense collagen layer will be extruded and deposited on a large rotating mandrel, as explained above. In the second step, the second biopolymer (elastin, collagen, fibrin and hydrogels) layer may be extruded, for example, also using the microfluidic device portion, and deposited on the first layer. If the second biopolymer layer involves anisotropic materials such as collagen and fibrin, it may be extruded using the embodiments of the present disclosure to achieve alignment. Even in the case of non-anisotropic materials such as elastin, the microfluidic device portion may be employed to achieve well-defined sheet dimensions (controllable, width and height). Such control over the sheet dimensions may be employed to mimic the microstructure of bilayer constructs such as blood vessels as opposed to using alternative methods (e.g. spraying the layer using commercially available guns).

In the case of elastin being the second layer, the temperature may be lowered for reflow of elastin layer and then increased to ensure that the elastin and collagen layer bind to each other to form a bilayer. When neutral pH collagen is used as the second layer, binding may be achieved by adding a small amount of fibrinogen to the neutral pH collagen solution before extruding it. Once the bilayer is formed, it may be transferred into a thrombin solution to cause the gelation of fibrinogen and indirectly binding the two layers to form an intact bilayered sheet. Additionally or alternatively, the addition of photoactive functional groups such as, but not limited to, benzophenones and acrylate groups, to the biopolymer solution may be employed to facilitate UV cross-linking between layers.

Bi-layered sheets of highly aligned (high elastic modulus E and low permeability P) collagen with an attached layer composed of a low E/high P biopolymer (e.g., collagen, elastin, fibrin, hydrogels and mixtures thereof, may provide immediately handleable engineered tissues. The high degree of fibril alignment and compaction of the aligned collagen layer could render it impermeable for bacteria and permit the moisture flux of the overall membrane to be controlled to about 0.1 to 1 mg/cm$^2$/hr.

Collagen or other biopolymer sheets could be fabricated with anisotropic electrical or magnetic conductivity through the alignment of electrically conductive or magnetic components, respectively. For example, electrically conductive collagen or biopolymer sheets could be used to embed sensors or otherwise fabricate electrically responsive sheets for controlled contraction and relaxation of sheets containing skeletal muscle cells or cardiomyocytes. Electrically conductive sheets could be produced to bridge nerve or spinal cord defects or to create neuromotor units. Likewise, electrically conductive sheets could be used for controlled delivery of embedded drugs. Directionally dependent electrical conductivity in aligned collagen sheets can be achieved with a variety of biologically compatible metallic colloidal nanomaterials as payloads, such as, but not limited to, spherical nanoparticles, gold nanorods, gold nanowires and carbon nanotubes.

Other applications include the creation of cell-containing or acellular vascular grafts by rolling collagen sheets with or without smooth muscle cells and endothelial cells or undifferentiated cells, including induced pluripotent cells, on a cylindrical rotating collection unit (mandrel). The aligned collagen sheets may be deposited in a way that the axis of the collection device is perpendicular to the direction of sheet extrusion (90 degrees) or at a well-defined angle between 45 degrees and 120 degrees to better mimic the circumferential alignment of collagen in intact vessels. The angle may a fixed angle, or a time-variable angle that varies relative to an extrusion direction of the polymer sheet. Similar tubular constructs composed of aligned collagen or other biopolymer sheets with appropriate cell types include the trachea and bronchi, esophagus, small and large intestine, or urethra.

Other planar structures with appropriate cell types could be used to create other tissues placement materials or tissue mimicking materials, such as, but not limited to, cornea, dura, heart valve leaflets, and cardiac patches. Solid cylindrical structures with appropriate cell types could be used to create skeletal muscle or tendon. Hollow spheroids with appropriate cell types could be used to create bladder. Stacks of aligned sheets of collagens that may contain proteoglycans or other chemically bound biomolecules to improve optical transparency across the visible spectrum may be used as collagen-based contact lenses.

Other non-tissue engineering applications include the production of sheets of precursor polymers with downstream processing. One example is a tanning step after cross-linking of the aligned collagen sheet assembly is completed that may be used for the production of artificial leather products (e.g., shoes, gloves). An example downstream processing step associated with a non-biological application of as-produced aligned polymeric sheets is the heat treatment for producing non-woven carbon fiber or Kevlar sheets. Applications of such high strength and energy absorbing materials include armor as well as the production of reinforced composite materials.

Colloidal electro-optical and electro-chemical devices could be produced in either one-step process or with the downstream integration of other processing steps. Examples for electro-optical devices are colloidal light emitting devices, solar cells, displays and lasers. Examples for colloidal electro-chemical and colloidal electrical devices are batteries, fuel cells, capacitors and supercapacitors.

EXAMPLES

The following examples are presented to enable those skilled in the art to understand and to practice embodiments of the present disclosure. They should not be considered as a limitation on the scope of the disclosure, but merely as being illustrative and representative thereof.

The examples below demonstrate a microfluidic approach for the continuous formation of wide collagen sheets, with the examples demonstrating a width-to-thickness ratio up to 400, with tunable alignment and compaction of collagen fibrils and fibers. The combination of a flow-focusing region and collection device results in collagen alignment in the direction of flow, with the degree of alignment and the density of collagen consistent throughout the sheet.

In the various non-limiting examples provided below, an acidic solution of collagen and a polyethylene glycol (PEG) solution were separately delivered to different layers of a multilayered microfluidic device at room temperature. At the device exit, a multilayered fluid, with a central collagen solution bound above and below by PEG solutions emerged and was guided through a fluid constriction unit. Gelation took place immediately at the areas where collagen was in contact with the PEG solution, with molecular alignment and an increase in collagen packing induced by the flow-focusing region and collecting device.

Using this method, and the example device described below, large aspect-ratio collagen sheets with dimensions that ranged from 3 to 17 mm in width and 30 to 250 μm in thickness were continuously produced. The degree of alignment of collagen and collagen compaction could be controlled affording the ability to tune mechanical properties. As a result, the range of collagen sheet properties included elastic moduli between 1.3 and 130 MPa, ultimate tensile strengths between 1.25 and 13 MPa, and strains to failure between 15 and 35%. The presence of D-periodic banding of ~67 nm typical of collagen fibrils and fibers was consistently observed in these collagen sheets. Vascular smooth muscle cells cultured on collagen sheets expressed contractile smooth muscle markers and aligned in the direction of the oriented collagen sheet. Endothelial cells did not display an inflammatory phenotype when cultured on collagen sheets. The examples provided herein suggest the application of the present example methods and devices for developing large collagen sheets of biologically relevant composition and tunable mechanical properties for a variety of applications.

Example 1

Microfluidic Device and Flow-Focusing Unit

In order to demonstrate the aforementioned example embodiments, an example fluidic device for forming aligned polymer sheets was fabricated as a microfluidic device portion and a multicomponent flow-focusing unit, as illustrated in FIGS. 4A-D.

The microfluidic device portion was fabricated using standard soft-lithography techniques and consists of three polydimethylsiloxane (PDMS) layers that were individually fabricated and subsequently bonded to form the final multilayered microfluidic device.[51] The top and bottom layers are configured to distribute a flow-confining solution, while the middle layer is configured to distribute an acidic collagen solution. These layers are shown in FIG. 2B and in FIGS. 3A-B.

FIG. 4A, and the cross-sectional view shown in FIG. 4B, show the interfacing of the microfluidic device portion 400 (the flow distribution portion of the fluidic device for generating the layered flow) with the flow-focusing unit 405. As can be seen in FIG. 4A, the microfluidic device portion was supported on a substrate 410, and the flow-focusing unit 405 was secured to the substrate 410 such that the microfluidic device 400 portion was clamped between the substrate 410 and a proximal portion of the flow-focusing unit 405. The distal region of the flow-focusing unit included an extrusion window 415 permitting visual observation (and/or optical processing, e.g. for inducing cross-linking) of the polymer sheet after it emerges from the flow-focusing constriction (conduit).

As shown in FIG. 4C, on the top and bottom, the collagen solution was bounded by flow-confining liquid layers as it exits the device and enters a flow-focusing unit. Hydrodynamic focusing takes place at a location downstream of the microfluidic device within a flow-focusing unit that is 12 mm wide (30 mm for wide sheets that were also produced), with a $L_G=2$ mm long section with a gap height of $H_G=4$ mm and a $L_C=6$ mm long flow constriction. The horizontal distance between the end of the constriction unit and the edge of the rotating drum is $L_P$, as shown in the inset to FIG. 2F.

As shown in FIG. 4D, the focusing system which consists of a separate (milled aluminum) part that is mounted to the outflow side of an elastomeric microfluidic device. The flow-focusing unit was machined in aluminum in order to retain a uniform constriction height, $H_C$, across the 12:1 aspect ratio ($W_O/H_C$) slit and, thereby, avoid any unwanted deformation that would be expected in the case of an elastomeric substrate material.[52] The constriction gap was horizontally aligned and tightly sealed against the exit section of the microfluidic device. The value of $H_G$ exceeded slightly the height of the device exit section by approximately 2.5 mm to ensure fluids from all three layers are consistently guided through the constriction.

The fluidic device shown in FIGS. 4A-D had the following properties:
Channel width (um): From outlet: 300 to 400 (inlet)
Dead volume of single layer: 326 mm^2*0.15 mm (channel depth)=48.9 mm^3=0.0489 mL
Device footprint: 37.95 (width)×40 (length)
Target (aligned) sheet width: ~15 mm
Target flow rate: Collagen: 400 ul/min, PEG: 4000 ul/min
Flow resistance in Collagen layer: Viscosity of Collagen solution at 23 C: 74 cp
Predicted inlet pressure: Inlet: 9.5E4Pa=0.94 atm, last bifurcation: 1.42E3Pa=0.014 atm
Ratio between last bifurcation and inlet=0.015=1.5% pressure drop
Flow resistance in PEG layers. Viscosity of PEG solution at 23 C: 19 cp. Predicted inlet pressure: Inlet: 2.46E5Pa=2.43 atm, last bifurcation: 3.7E3Pa=0.0365 atm, Ratio between last bifurcation and inlet=0.0150=1.5% pressure drop
Inlet hole size and positions: diameter: 1.27 mm holes, no justification for position
Composition of fluid: Top & Bottom layer focusing fluid: 10% wt/v PEG, 35 kDa (pH 8), middle layer: 2-5 mg/ml lyophilized collagen (pH 2)

As described below, the example apparatus enables the continuous formation of collagen sheets with a controlled width, w, thickness, δ, and angle of fibrillar alignment, θ. In the results described below, the sheet width was determined at the collecting unit from measurements performed with three microfluidic devices that had exit widths of $w_0=5$ mm, 10 mm, and 25 mm. The thickness and fibril alignment of the collagen sheets depended upon the following experimental parameters including the collagen flow rate, $Q_M$, the flow rate of the flow-confining fluid, $Q_F$, and the pulling velocity, $V_P$, each of which are controllable. In the following examples, the roles of hydrodynamic focusing and strain-imposed on the formed sheets are assessed.

Example 2

Characterization of Flow-Focusing Unit

In the present non-limiting example, the microfluidic flow network distribution region and flow focusing region were provided as separate device components, in order to experimentally characterize how the sheet thickness locally varies at different locations downstream of the exit section of the microfluidic device region. This was evaluated as the central collagen sheet flows through the flow-focusing unit and pulling-induced strain is being applied. As can be seen in FIG. 5A, the microfluidic device, formed from the microfluidic flow-distribution portion and the flow-focusing region, was oriented in the vertical direction, providing for visual access from below, within the constriction, thereby allowing the collagen sheet thickness variation to be imaged in the (x, z)-plane, using an inverted microscope.

FIG. 5B shows bright-field images of the exit region of a microfluidic region (top image), and of a collagen sheet being formed within the flow-focusing region (bottom image). The bottom image was captured for a device with $w_0=10$ mm at conditions $Q_M=100$ µL/min, $Q_F=1$ mL/min, $V^*=4.5$. As explained above, a non-dimensionalized velocity parameter $V^*$, which is obtained by relating the pulling velocity to the total velocity of the working fluids, may be employed to characterize the experimental conditions. The flow profile of the focusing solution within the flow focusing conduit was further visualized by incorporating fluorescent microspheres (1 µm diameter carboxylate microspheres labeled with Nile red) at a concentration of 0.08% v/v.

Long-term exposure images (exposure time 400 ms) captured the streamlines within the two regions of interest that are indicated in FIG. 5C. Specifically, streamlines within the entrance region entering the constriction (window d) and the upper wall of the chamber before the constriction (window e) were investigated. The images shown in FIG. 5D, corresponding to window d, were obtained at $Q_M=100$ µL/min, $Q_F=1$ mL/min, $V^*=10$ and illustrate the streamlines of the focusing fluid travelling parallel to the moving liquid collagen sheet in its proximity. In FIG. 5E, corresponding to window e, no collagen was flown through the microfluidic device and $Q_F=1$ mL/min. The presence of recirculating flows can be observed in the upper wall of the open region before the constriction. The size of the recirculation zone decreased when increasing $Q_F$ from 1 mL/min to 6 mL/min. However, the recirculating vortices do not interact with the collagen sheet, suggesting that the formation of collagen with consistent control over the width and thickness is unaffected by their presence.

Example 3

Sheet Formation

Employing the flow-focusing unit allowed the formation of thinner collagen sheets. As $V^*$ increased, the cross-sectional area of the sheet was reduced by close to 90% with a sheet thickness as small as 3 microns. In principle additional reductions in sheet thickness could be achieved as $V^*$ is further increased. The experiments were conducted using three devices with $w_0$ values of 5 mm, 10 mm, and 25 mm.

For the device with $w_0=5$ mm, the conditions $Q_M=50$ µL/min, $Q_F$ at 1 mL/min, and $V_P=1$ to 20 mm/s were applied. In the case of the two other devices ($w_0=10$ mm and 25 mm), the same range of $V_P$ was considered, and $Q_M$ and $Q_F$ were adjusted proportionally with the increase in device width (i.e., the flow rates were twofold higher in case of $w_0=10$ mm, and five-fold higher in case of $w_0=25$ mm), and the corresponding $V^*$ were calculated accordingly.

The use of the flow-focusing unit produced wider and thinner collagen sheets. Collagen sheets formed without constriction were between 0.65±0.21 mm and 3.3±0.17 mm wide. With the inclusion of the constriction, the widths, at the same flow rates, were between 3.3±0.09 mm and 17.3±0.1 mm wide.

Figure 6A:
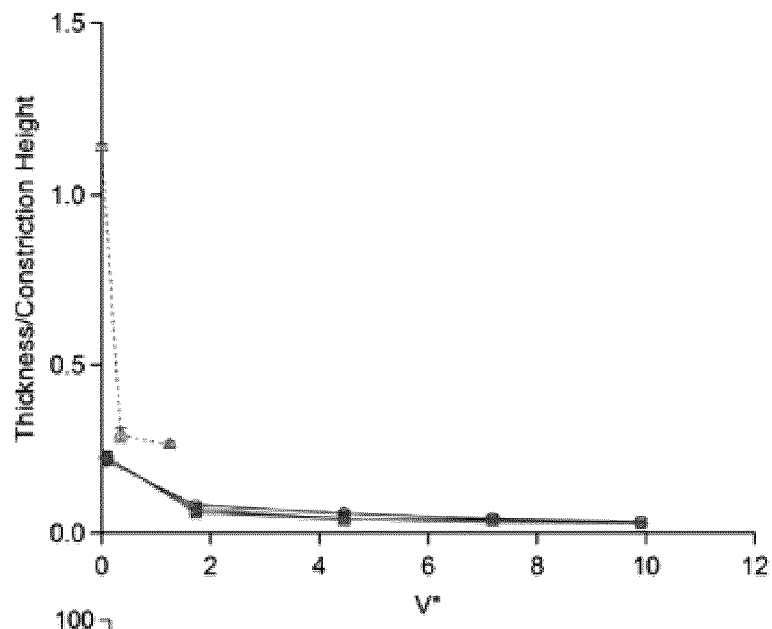
FIGS. 6A and B presents the measured collagen sheet width and thickness as a function of $V^*$ ranging from 0.1 to 10.

The constriction unit reduced the thickness of the produced sheets by up to 88%, from $\delta=260\pm8$ µm to 1140±10 µm without the constriction unit and from 30±3 µm to 213±15 µm with the constriction unit (FIG. 6A). The measurements of the external sheet dimensions w and δ for all three devices were non-dimensionalized by $w_0$ and $H_C$, respectively.

The self-similarity of the results demonstrates the utility of the approach for the predictive formation of a large aspect ratio collagen sheet with a certain target width, by selecting a microfluidic device with an appropriate width $w_0$. Sheet dimensions w and δ were studied for $w_0=10$ mm, $V^*=0.1$ to 10, $Q_M=100$ µL/min, and $Q_F=1$ to 6 mL/min. The obtained data suggest a decrease in both width and thickness for an increasing flow rate of the PEG solution, $Q_F$, with $w/w_0=0.32$ to 0.8, and $\delta/H_C=0.025$ to 0.3.

Example 5

Nanoscale Properties

As shown in the inset to FIG. 2D, the formed collagen sheet was collected on a rotating drum at a distance $L_P$ downstream from the flow-focusing unit. Along with the applied flow rates, $Q_F$ and $Q_M$, the speed of drum rotation, V, and the corresponding dimensionless parameter, $V^*$, affects not only sheet dimensions but also the alignment of collagen and fibril packing density. The cross-sectional area of the wet collagen sheets, w·δ, was calculated, plotted against $V^*$, and compared to the calculated cross-sectional area. The calculated values were obtained from $Q_M/V_P$. Data obtained from experiments were conducted with three device widths, $w_0=5$ mm, 10 mm and 25 mm, where $Q_M=50$ µL/min ($w_0/5$ mm) and $Q_F=1.5$ mL/min ($w_0/5$ mm).

Figure 6B:
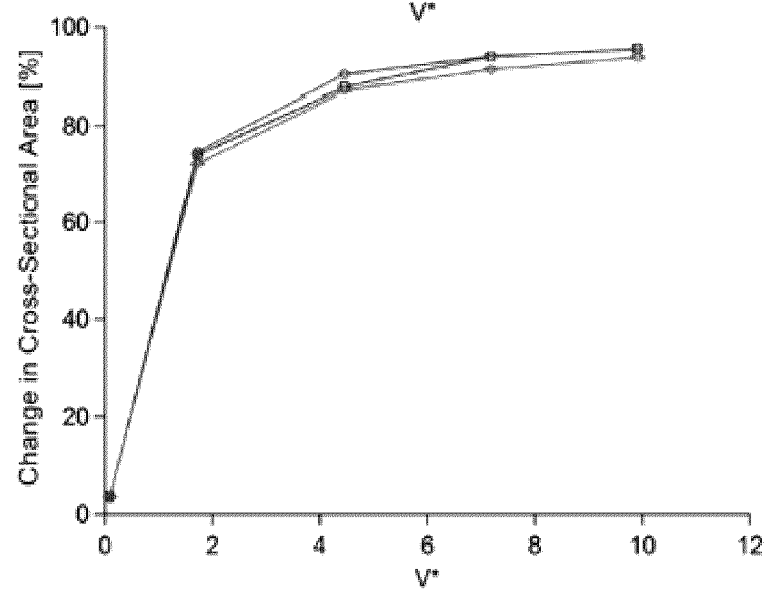
FIG. 6B shows the percentage change in cross-sectional area of the formed polymer sheets, evaluated after sheet formation, and normalized by the area of the device exit for $w_0$=5 mm, 10 mm, and 25 mm as a function of $V^*$.

For values of $V^*$ below a threshold, $V^*_{th}$, the measured cross-sectional area exceeded the one predicted under the assumption of a conserved volume. For $V^*>V^*_{th}$, the opposite case was observed, demonstrating compaction of the collagen sheet. The degree of compaction was determined by comparing the final and initial cross-sections of the sheets and ranged from 3 to 96% (FIG. 6B).

This can be explained by the relationship between the flow rates, $Q_M$ and $Q_F$, with the pulling velocity, $V_P$. At an initially low $V_P$, the average total velocity of the collagen and flow-confining solutions through the flow focusing unit is larger than the pulling velocity, suggesting that the fibril alignment is solely due to hydrodynamic focusing and no strain is being exerted by the collecting device rotation. However, once $V_P$ exceeds the average velocity of the collagen sheet leaving the microfluidic device, a strain is applied by the collecting device that causes the alignment of fibrils along the length of the sheet, a reduction of the average fibril-to-fibril spacing and a compaction of the sheet.

The degree of compaction and fibril packing density was also characterized by transmission electron microscopic (TEM) and scanning electron microscopic (SEM) imaging of collagen sheets. Collagen samples produced across a wide range of $V^*$ were examined. TEM and SEM images revealed the degree of fibril alignment and packing density with an observed increase in fibril packing density and alignment with increasing $V^*$ from 0 to 10 (FIG. 7A, B).

D-periodic banding of collagen fibers can be observed in TEM and SEM images of highly aligned collagen sheets (FIG. 7A-2, B-2). The D-periodic banding of collagen fibers was calculated by applying an autocorrelation function to line intensity plot obtained in the x-axis of the SEM image in FIG. 7E ($V^*=7$). A banding period of 67 nm was determined, which is characteristic of intact collagen fibrils and confirms that the triple helical structure of collagen was preserved.

The degree of compaction was measured by analysis of the SEM images of collagen sheets formed at $V^*=0.1$, 0.6, 4.5, and 10. An autocorrelation function was calculated for the intensity distributions in SEM and TEM images using the software program Matlab (Mathworks, Econometrics Toolbox, Natick, Mass., USA). Fibril spacing was measured from the resulting plots. As a sample, FIG. 7C shows an autocorrelation function of the TEM image in FIG. 7A-2. Fibril spacing for all V* conditions are summarized in FIG. 7D and indicate a 95% decrease, from 139±37 nm for V*=0.1 to 6.5±1.2 nm for V*=10 (FIG. 7D, insert).

In addition to the degree of compaction and the banding length, fibril alignment of the collagen sheets was characterized by applying a Fast Fourier Transform (FFT) algorithm to the SEM images obtained using an image processing software (ImageJ). The percentage of aligned fibrils was plotted as frequency (%) versus the angle of alignment (FIG. 7F), confirming the degree of alignment was directly proportional to V*, with up to 40% alignment observed at V*=10* (obtained by adding the frequencies within ±5 degrees of the reference angle of alignment at 90 degrees).

Figure 7G:
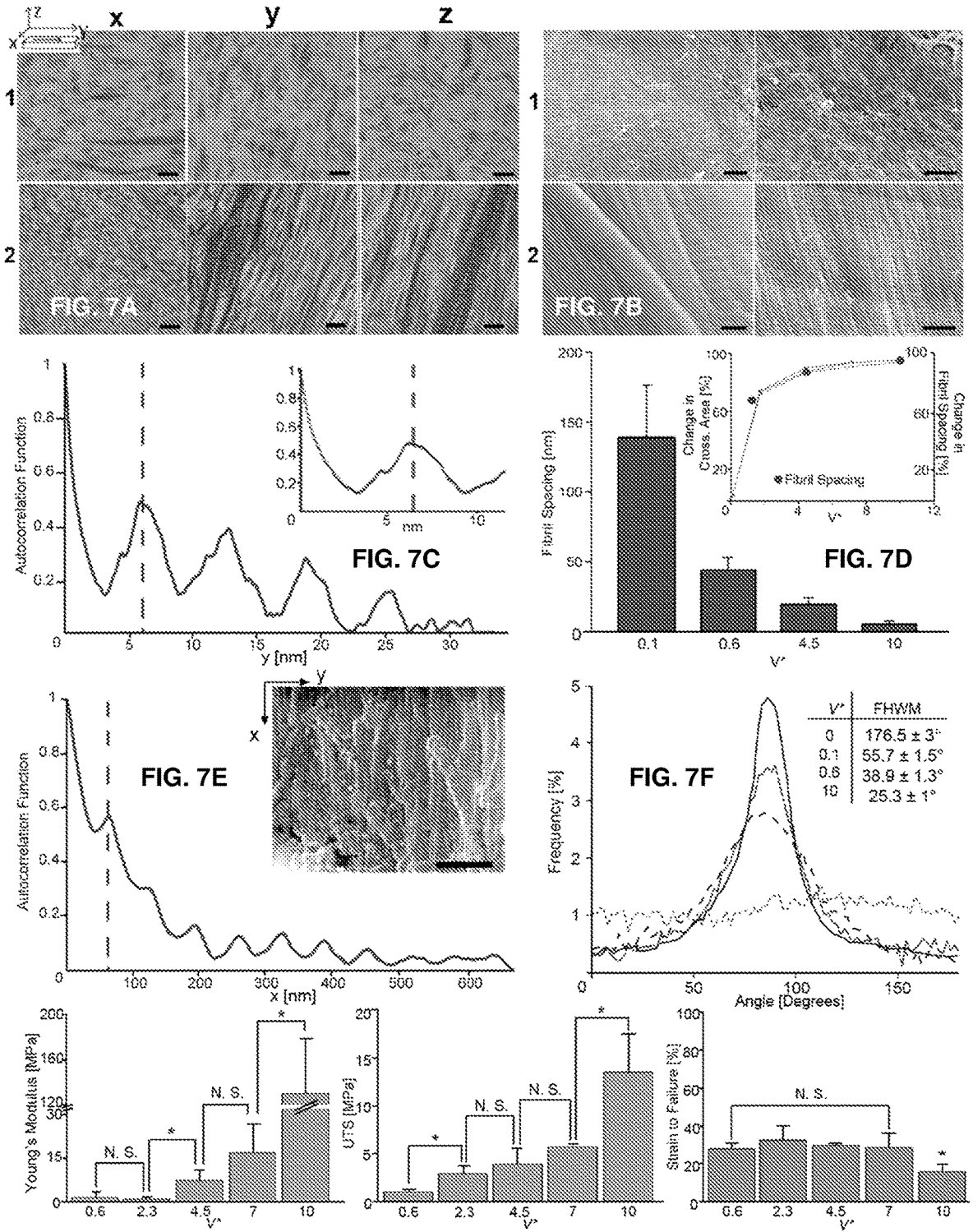
Figure 7H:
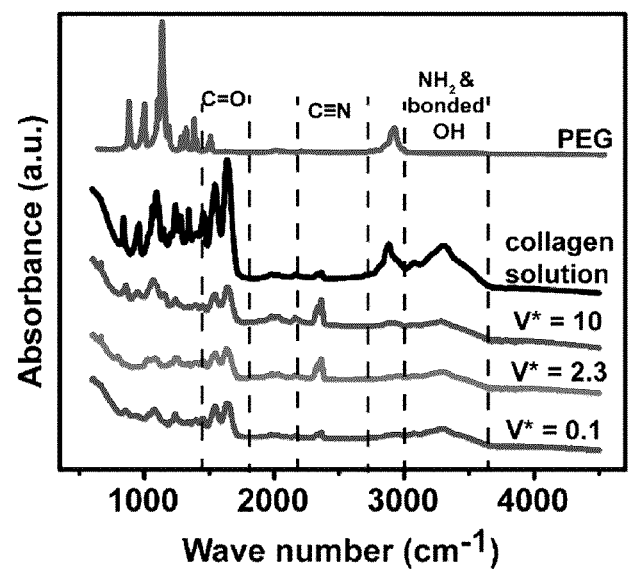

Fourier Transform Infrared Spectroscopy (FTIR) was performed on the extruded sheets to determine the cross-linking (physical/chemical) between the WSB and collagen solutions. FIG. 7H plots the FTIR data for the collagen and WSB solutions (containing 10 wt %) PEG along with the sheets extruded at different V*. The resemblance of the functional group peaks ($NH_2$ and bonded OH and CN) in the extruded sheets to collagen solution and not the WSB solution, shows the absence of any traces of PEG in the collagen sheet. This indicates physical crosslinking between PEG and collagen solution as it is removed before transferring into Fiber Incubation Buffer (FIB) to begin fibrillogenesis.

Figure 7I:
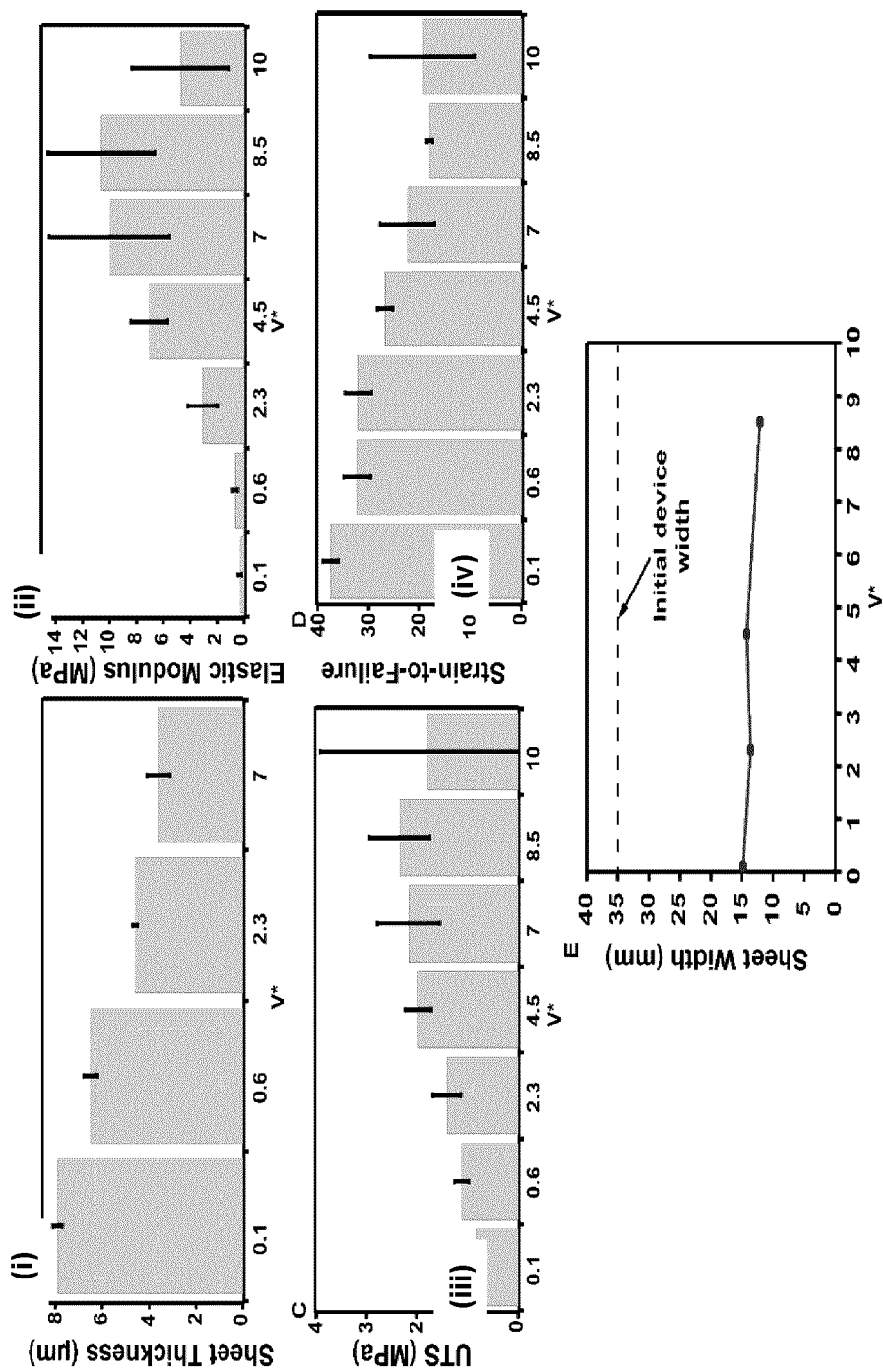
FIG. 7I plots the tensile properties of aligned collagen sheets. (i) Thickness of aligned collagen sheets as a function of $V^*$. With increase in $V^*$, sheet thickness decreases due to compaction with the smallest thickness of 4 μm for $V^*$=10. (ii) Measured aligned sheet elastic moduli. (iii) The ultimate tensile strength (UTS) of our aligned collagen sheets, (iv) Stress-Strain failure ratios for the aligned sheets. The flow-rate for the collagen stream, QM, and confining fluid solution, QF, are 400 μl/min and 4 ml/min respectively.

FIG. 7I plots the tensile properties of aligned collagen sheets. Graph (i) plots the thickness of aligned collagen sheets as a function of V*. As can be seen from the figure, with increase in V*, the sheet thickness decreases due to compaction of fibers with the smallest thickness of 4 μm for V*=10. Graph (ii) plots the measured aligned sheet elastic moduli as a function of V*. As seen, the elastic modulus increases with the pulling velocity. The shear rate and strain imposed by the rotating mandrel together increase the Weissenberg Number (Wi) making it greater than 1. This allows the uniaxial stretching of the collagen molecule in the direction of pulling, hence anisotropic alignment. The greater the imposed strain, greater is the degree of alignment and fiber compaction leading to increase in elastic modulus and decrease in sheet thickness. Graph (iii) plots the ultimate tensile strength (UTS) of the aligned collagen sheets as a function of V*. Graph (iv) Plots the stress-strain failure ratios for the aligned sheets as a function of V*. The increase in fiber compaction with increase in pulling velocity causes the sheet to become more brittle causing failure at lower strain-to-failure. For all these conditions, the flowrate for the collagen stream, $Q_M$, and confining fluid solution, $Q_F$, are 400 μl/min and 4000 μl/min respectively.

Example 6

Macroscale Properties

The direct impact of fibril alignment on the mechanical properties of collagen sheets was confirmed through uniaxial tensile measurements. Samples were prepared and mechanically tested using an inverted DMTA (Dynamic Mechanical Thermal Analysis) in PBS at 37° C. for 30 min. Specifically, the Young's modulus and ultimate tensile strength we observed to increase dramatically as a function of increasing V*. The Young's modulus increased by more than two orders of magnitude (1.3 to 130 MPa) and UTS increased by more than one order of magnitude (1.25 to 13 MPa) as V* increased from 0.6 to 10. Strain to failure ranged between 15% to 35% for sheets produced under these conditions (FIG. 7G).

Example 7

Cellular Phenotypic Changes and Behavior on Aligned Materials

The alignment, shape, and phenotype of vascular smooth muscle cells (vSMCs) were probed on collagen sheets under aligned (V*=10) and non-aligned (V*=0.1) conditions.

Culture of vSMCs on non-aligned collagen sheets was associated with the random cell distribution (FIGS. 9A-D). When cells were cultured on aligned collagen sheets, vSMCs were highly oriented in the direction of the aligned collagen. Cell cultured on both aligned and non-aligned collagen sheets expressed contractile smooth muscle markers, calponin and myosin heavy chain, and displayed similar cell shape. Elastin was produced by vSMCs cultured on aligned collagen sheets.

Figure 9E:
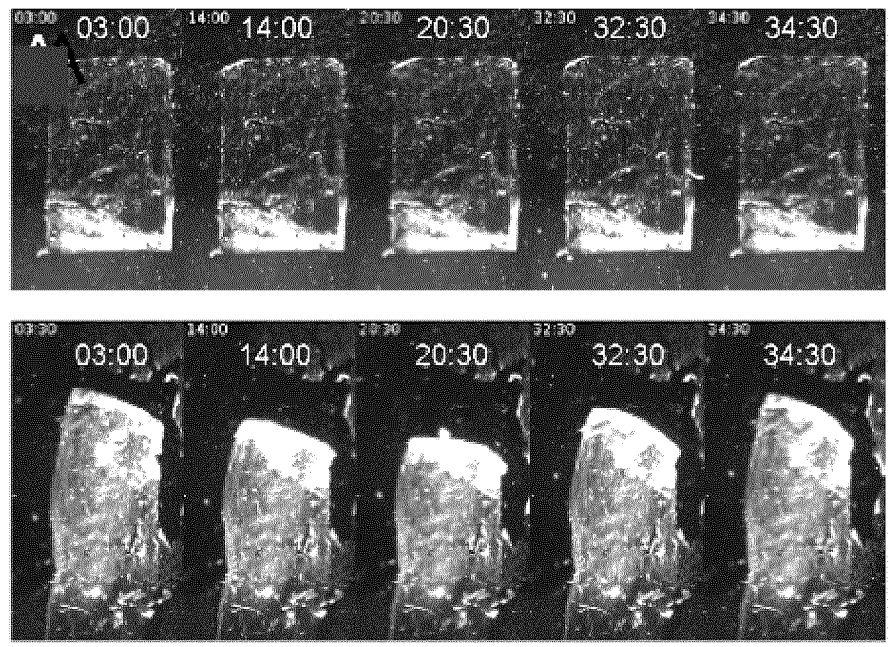
FIGS. 9E-G show functional data on SMC seeded aligned collagen sheets.
Figure 9F:
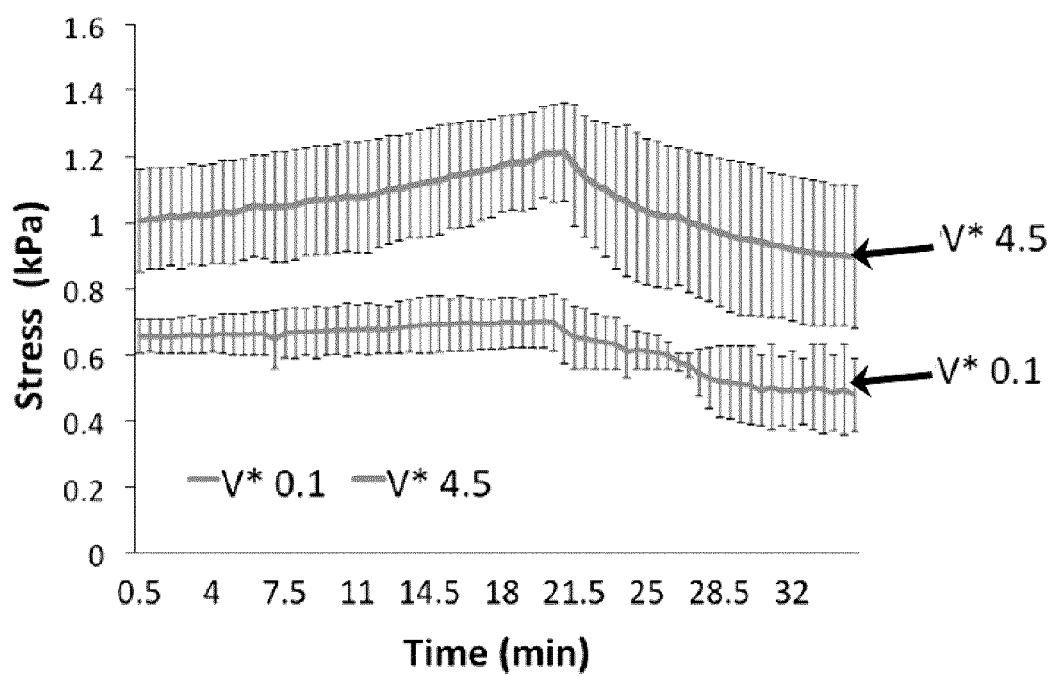
Figure 9G:
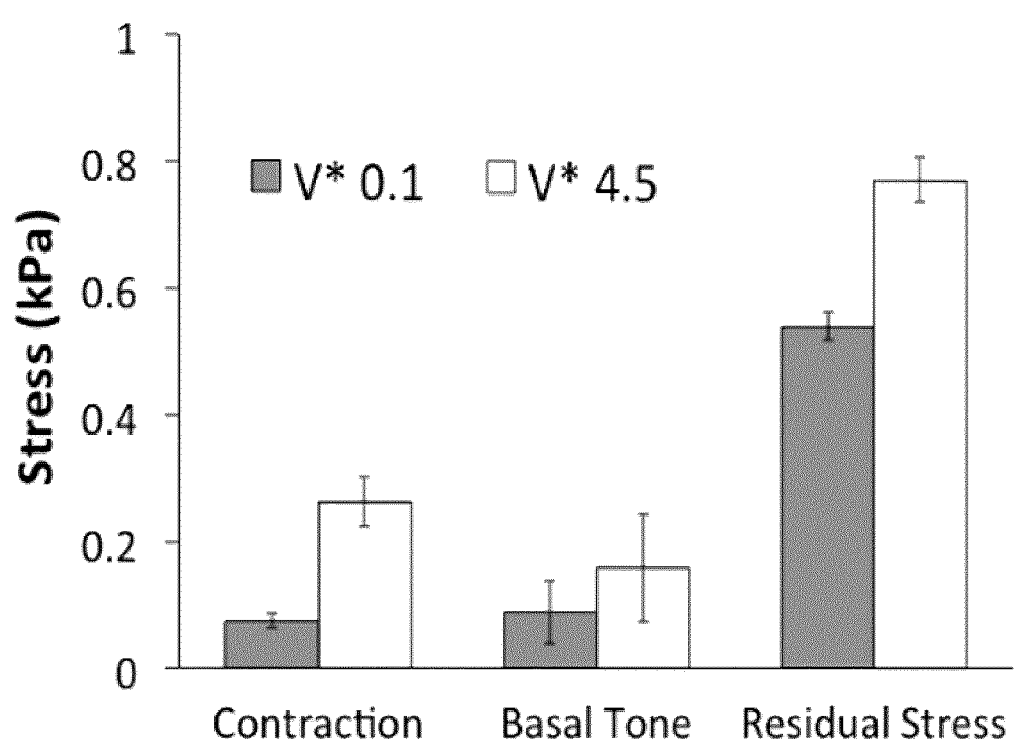

FIGS. 9E-G show functional data on SMC seeded onto aligned collagen sheets. Smooth muscle cells (SMCs) are cultured on aligned collagen sheets. The molecular alignment induces alignment in SMCs (as shown above in FIGS. 9A and 9C). The cellular alignment results in consistent degrees of sheet bending in the cases where SMCs are stimulated with a vasoactive compound. The functional responses from vascular smooth muscle thin films constructed on aligned ultrathin collagen sheets and tissue engineered blood vessels are shown in three figures. FIG. 9E shows the vasoconstriction and relaxation responses of human vascular SMCs grown on non-aligned (top) and aligned (bottom), 3 μm thick, collagen sheets. FIG. 9F plots the averaged time traces of stress generated by engineered vascular smooth muscle on aligned (V*=4.5; red line, n=6) and non-aligned (V*=0.1; blue line, n=10) collagen sheets. The samples were stimulated by 100 nM endothelin-1 at 5 min and 100 μM HA-1077 at 20 min. FIG. 9G plots the contraction stress generated in response to vasoconstrictor treatment, basal tone revealed by vasodilator treatment, and the residual stress were calculated from time traces for aligned (V*=4.5) and non-aligned (V*=0.1) collagen sheets (mean±SEM). This data highlights the potential utility of aligned collagen sheets as a means to perform functional tests in vitro.

Culture of endothelial cells (ECs) on non-aligned and aligned collagen sheets did not influence cell orientation but ECs grown on aligned collagen sheets displayed a different shape index, consistent with cell elongation. Neither inflammatory marker, ICAM-1 or VCAM-1, was expressed by ECs cultured on either sheet type, although, as anticipated, both markers could be induced when cells were exposed to TNF-α (FIGS. 10A-D).

FIGS. 11A-B illustrates expression of smooth muscle cell contractile proteins, calponin and myosin heavy chain (MHC), and elastin. The figures show immunofluorescent staining of vSMCs cultured on non-aligned (FIG. 11A) and highly aligned collagen sheets (FIG. 11B). Scale bars=100 μm for calponin and MHC in FIGS. 11A and 116B.

FIGS. 12 A-B show TEM images of extruded collagen sheets containing gold nanorods that were prepared at (A) V*=0 and (B) V*=10. Scale bars are 500 nm.

Example 8

Materials and Methods

Isolation and Purification of Monomeric Collagen

Acid-soluble, monomeric rat-tail tendon collagen (MRTC) was obtained from Sprague-Dawley rat tails following Silver and Trelstad[65]. Frozen rat tails (Pel-Freez Biologicals, Rogers, AK) were thawed at room temperature and tendon was extracted with a wire stripper, immersed in 10 mM HCl (pH 2.0; 150 mL per tail) and stirred for 4 hr at room temperature. Soluble collagen was separated by centrifugation at 30,000 g and 4° C. for 30 minutes followed by sequential filtration through 20 µm, 0.45 µm, and 0.2 µm membranes. Addition of concentrated NaCl in 10 mM HCl to a net salt concentration of 0.7 M, followed by 1 hr stirring and 1 hr centrifugation at 30,000 g and 4° C., precipitated the collagen. After overnight redissolution in 10 mM HCl the material was dialyzed against 20 mM phosphate buffer for at least 8 hr at room temperature. Subsequent dialysis was performed against 20 mM phosphate buffer at 4° C. for at least 8 hr and against 10 mM HCl at 4° C. overnight. The resulting MRTC solution was stored at 4° C. for the short-term or frozen and lyophilized.

Preparation of Collagen Neutralization Buffer

The flow-confining solution consisted of 10 wt % PEG (MW 35 kDa), 4.14 mg/mL monobasic sodium phosphate, 12.1 mg/mL dibasic sodium phosphate, 6.86 mg/mL TES, and 7.89 mg/mL sodium chloride.

Collagen Sheet Incubation and Drying

After collagen extrusion and pulling onto the collection device, the sheets were collected and immersed in collagen neutralization buffer without PEG (4.14 mg/mL monobasic sodium phosphate, 12.1 mg/mL dibasic sodium phosphate, 6.86 mg/mL TES, and 7.89 mg/mL sodium chloride) for 1 hr, after which they were washed three times with ddH$_2$O. Sheets were subsequently incubated in phosphate buffer (7.89 mg/mL sodium chloride, 4.26 mg/mL dibasic sodium phosphate, 10 mM Tris, pH 7.4) at 37° C. for 48 hr. Following incubation, the collagen sheets were rinsed in ddH$_2$O for 1 hr and dried on a glass slide under constant forced air flow.

Mechanical Testing of Planar Constructs

Collagen sheets were cut to 13 mm in length, mounted onto a Dynamic Mechanical Thermal Analyzer V (DMTA V, Rheometric Scientific, Piscataway, N.J.), and immersed in PBS at 37° C. After 5 minutes of incubation, samples were preconditioned 15 times to 66% of the average maximum failure strain of initial test samples, then tested to failure at 5 mm/min. A total of five samples were tested for each group. Thickness of hydrated samples was measured using optical microscopy. Young's modulus was determined from the slope of the last 4% of the stress-strain curve prior to breakage. Ultimate tensile strength and strain at failure were also reported.[67,68]

SEM Imaging

Dry collagen ribbons were hydrated in water for 24 hours, then dehydrated in serial ethanol washes ranging from 30% to 100%. Samples were then dried in a critical point dryer (auto Samdri 815 Series A, Tousimis, Rockville, Md.), sputter coated for 60 seconds with a platinum/palladium target at 40 mA (208HR Cressington, Watford, England), and imaged. Imaging was completed at an accelerating voltage of 5 kV on a field emission scanning electron microscope (Zeiss Ultra Plus, Center for Nanoscale Systems, Harvard University).[68]

TEM Imaging

Dry collagen ribbons were washed in 0.1 M cacodylate buffer, and fixed in 2.5% gluteraldehyde and 2% paraformaldehyde. After washing in water, samples were partially dehydrated in ethanol, then embedded in LX 112 resin, and polymerized. Ultrathin (60-80 nm) sections were cut with an RMC MT-7000 ultramicrotome (Boeckeler, Tucson, Ariz.). Post-staining was done with 3% uranyl acetate for 10 minutes, followed by Reynolds lead citrate for 5 minutes, then samples were imaged using a JOEL JEM-1400 TEM (JOEL, Tokyo, Japan) at 80 kV. Calculations of collagen fiber packing density were done with x-plane images at 15000× with ImageJ.[67]

Cell Culture

All primary cells were purchased from Lonza (Walkersville, Md.), and cultured at 37° C. and 5% CO$_2$. Human umbilical artery smooth muscle cells (uaSMCs) and human vascular smooth muscle cells (vSMCs) were cultured in fully supplemented SMGM (Lonza, Walkersville, Md.), and were used prior to passage 10. Human umbilical vein endothelial cells (HUVECs) were cultured in fully supplemented EGM-2 (Lonza, Walkersville, Md.), and were used prior to passage 6.

Cell Alignment Study

Collagen ribbons were cut to size and sterilized with 70% ethanol solution containing antibiotic/anti-mycotic solution for 1 hour, then rinsed with 3 washes of PBS pH 7.4. vSMCs were trypsinized and seeded onto the constructs at a concentration of 200,000 cells/cm$^2$. Cells were allowed to adhere for 4 hours, then additional media was added to the tissue culture well. After appropriate culture times, samples were stained with 2 µM calcein AM and 4 µM ethidium homodimer and imaged with a Leica SP5 X inverted confocal microscope (Wetzlar, Germany). Alignment was quantified by using the Fast Fourier Transform function in ImageJ on the binarized image, then utilizing the radial summing profile in 5° increments. This data was then plotted, and full width at half maximum was calculated. Cell shape index (CSI) was quantified using CellProfiler image analysis software to determine the area and perimeter of each cell, then CSI was calculated as previously described.[69]

Immunofluorescent Staining

Collagen ribbons were cut to size and sterilized, and human vSMCs were trypsinized and seeded onto the constructs in an identical manner as described above. Cells were cultured for either 3 or 7 days in fully supplemented serum-free SMGM. After appropriate culture times, media was removed with 3 washes of PBS pH 7.4 for 5 minutes each. Samples were fixed in 10% buffered formalin for 20 minutes at 4° C. and washed 3 times with PBS pH 7.4 for 5 minutes each. Permeabilization was completed with a 5 minute incubation in 0.3% Triton X-100 in PBS. Samples were then washed 3 times with 0.1% Triton X-100 in PBS (PBS-T) for 5 minutes each. Non-specific binding was blocked for 1 hour with a solution of 0.1% Triton X-100 in PBS with 2% BSA at room temperature and washed 3 times with PBS-T for 5 minutes each. Primary antibody (myosin heavy chain, (1:100) calponin (1:100), or elastin (3:100), (Abcam, Cambridge, Mass.)) was diluted 1:100 and incubated overnight at 4° C. and removed with 3 more washes in PBS-T. Secondary antibody (AlexaFluor 660, Life Technologies) was diluted 1:400, incubated for 2 hours at room temperature, and removed with 3 final washes with PBS-T. Samples were mounted with Prolong Anti-fade containing DAPI (Life Technologies), and stored at 4° C. until imaging on a Leica SP5 X inverted confocal microscope (Wetzlar, Germany).

For endothelial cell studies, HUVECs were trypsinized and seeded at 100,000 cells/cm$^2$ in fully supplemented EGM-2 onto collagen sheets or into individual wells of a chambered cover glass and allowed to adhere for 48 hours. Medium was then replaced with fully supplemented EGM-2 without serum for 24 hours to achieve a quiescent phenotype. Positive control samples were treated with TNF-α (100 ng/mL in EGM-2) for 4 hours prior to fixation and staining. All samples were fixed and stained as described above. Primary antibodies were utilized at 1:50 dilutions (ICAM, VCAM; Abcam). Samples were also stained for F-actin (1:40 from a 6.6 µM stock solution, Life Technologies) for 20 minutes following standard protocol.

RT-PCR 6-well plates were coated with a 1:10 ratio of polydimethylsiloxane curative to polymer and allowed to cure overnight at 60° C. Collagen sheets were dried completely onto the PDMS surface, and cells were cultured at 200,000 cells/cm$^2$ for 24 hours (vSMCs) with standard media conditions described above. Constructs containing cells were manually removed from the PDMS surface and RNA was extracted using a standardized kit (Life Technologies). Two-step reverse transcription polymerase chain reaction (RT-PCR) was performed for ACTA2 (alpha-actin), CNN1 (calponin 1), MYH11 (myosin heavy chain), ELN (elastin) and SMTN (Life Technologies). Analysis was done utilizing the standard $\Delta C_t$ method.

Statistics

Mean and standard deviation were obtained for all measurements, with a minimum of n=3 for each condition. Comparisons were made using ANOVA for multiple comparisons, with Tukey post hoc analysis for parametric data, and Kruskal-Wallis for non-parametric data. Values of p<0.05 were considered statistically significant.

Example 9

Monolithic Device with Microfluidic Flow Distribution Region and Flow Focusing Region The example embodiments shown in FIGS. 2A-D and FIGS. 4A-D employed a hybrid design, in which a microfluidic device portion was employed for forming the layered flow and a flow-focusing unit was interfaced with the microfluidic device portion. In another example implementation that is described below, these components may be integrated into a single device, such as a single multilayer device, with at least a portion of the flow-focusing region integrated with at least a portion of the microfluidic device. An example of such an integrated fluidic device is shown in FIG. 13A, in which the flow-confining feature responsible for aligned collagen sheet formation is fully integrated within the same device as the flow-focusing conduit.

In one example implementation, such an integrated layered device may be fabricated using thermoplastics ("hard plastic") and epoxy resins as substrate materials. Standard micromachining procedures may be employed, including, but not limited to, photolithography, hot embossing, carbon dioxide laser machining, and solvent bonding. In the design and fabrication of the example integrated device shown in FIG. 13A, high-resolution 3D Printing, hot embossing, and scalable manufacturing using a commercial microinjection molding production run were employed. The integrated thermoplastic device shown in FIG. 13A had a 1.69 times reduction in device footprint relative to the dual-component hybrid device shown in FIGS. 4A-D. The integrated device fabrication utilized a scalable manufacturing process, non-manual hole drilling, and an on-chip constriction for flow focusing. The on-chip constriction provides improved optical access for in situ characterization, ability to form sheets with pressure controlled delivery of biopolymer solution directly from well (low dead volume, cartridge only wetted part in contact with biopolymer solution, i.e., manifold only for thermal management and PEG solution), extend range of flow rates compatible with aligned sheet formation. In the case of applications involving the formation of collagen sheets, translating device fabrication to the same substrate materials that are already widely adapted in cell and tissue culture (e.g., acrylic, polystyrene, and cyclic olefin copolymers) allows for the inclusion of the flow focusing (constriction) region within the device itself for simultaneous buffer neutralization and initiation of in-flow fibrillogenesis and allow for scalable device manufacturing using hot embossing and injection molding.

Translating device fabrication to the same thermoplastic ("hard plastic") substrate materials that are already widely adapted in cell and tissue culture (e.g., acrylic, polystyrene, and cyclic olefin copolymers) will also provide the option for evaluating simultaneous layering of an elastin analogue onto a collagen sheet by imposing a step-change in temperature between the inflow and the constriction sections of the device for thermally-mediated gelation of the elastin analogue ($T_f$~15° C.); and to facilitate scalable manufacturing using available commercial manufacturing processes for thermoplastic substrates (i.e., hot embossing and microinjection molding). Without intending to be limited by theory, it is estimated that substantially increasing the fluid shear rate an integrated device will enhance flow mediated collagen self-assembly, which when combined with in-flow neutralization of an acidic collagen solution, will avoid the need for buffer incubation to promote collagen fibrillogenesis.

Figure 13A:
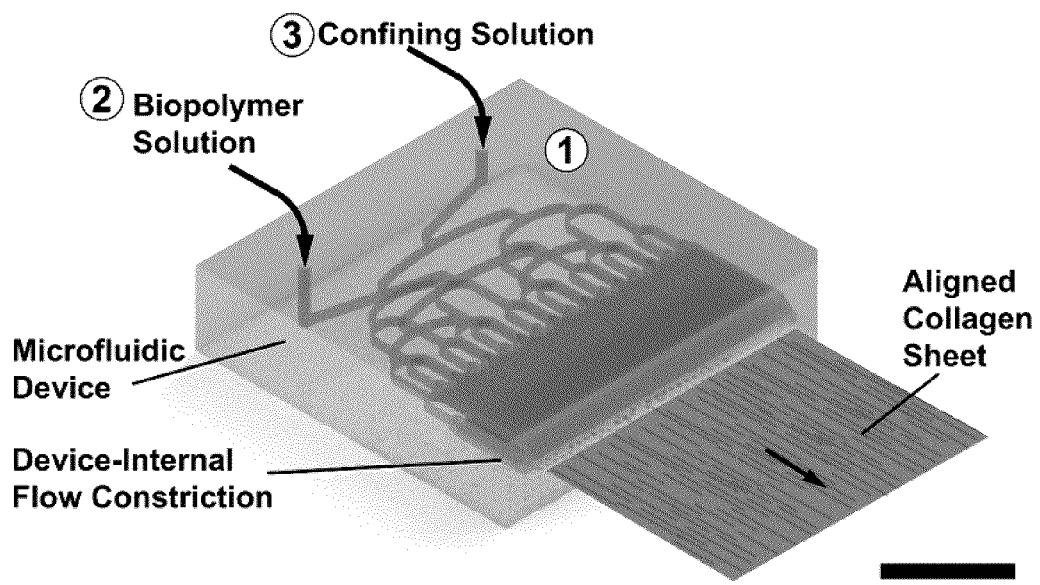
FIG. 13A illustrates an integrated device design in which the flow focusing region is integrated with the microfluidic device region.
Figure 13B:
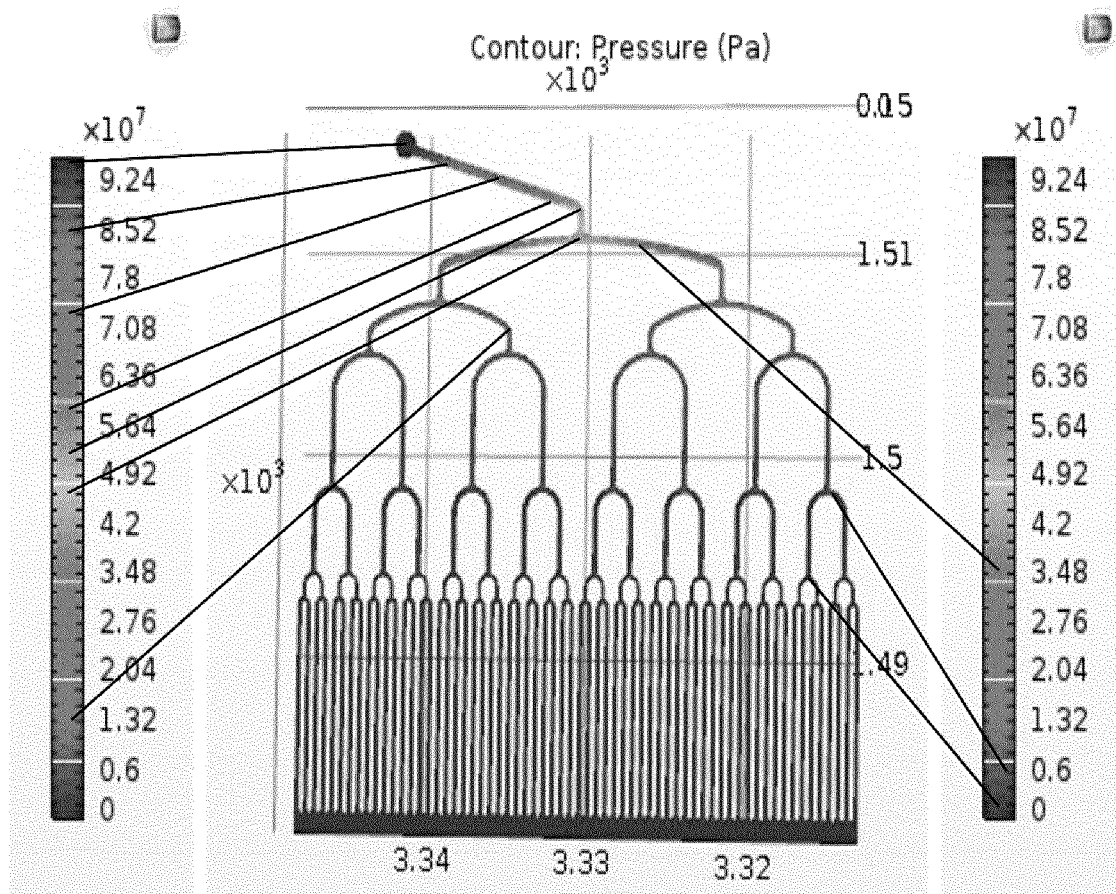
FIGS. 13B and 13C show the reduced footprint device design according to Murray's law with lower inlet pressure and dead volume.
Figure 13C:
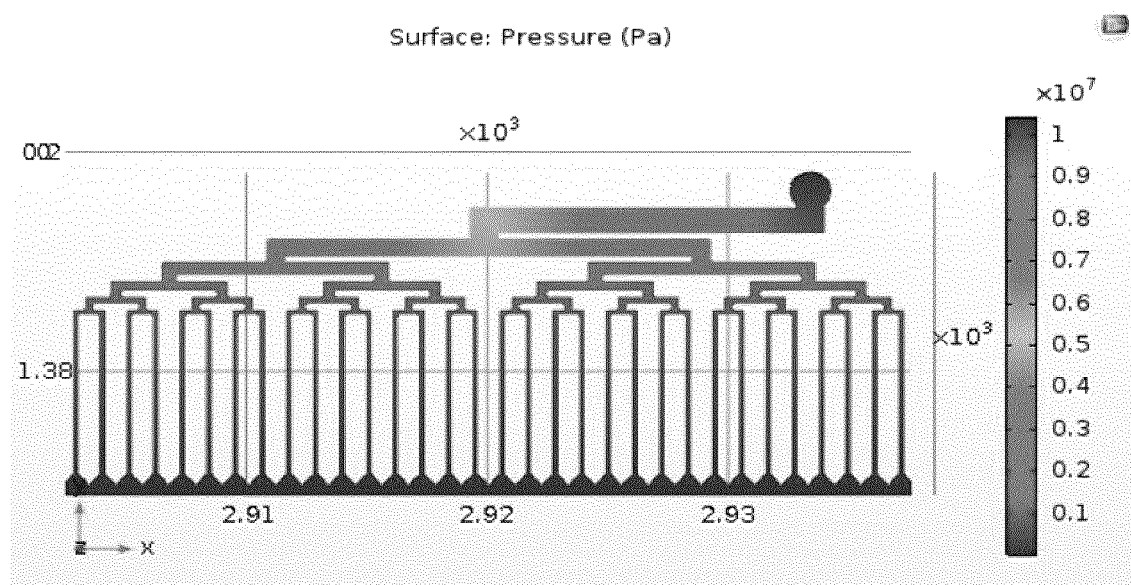

Referring now to FIGS. 13B and 13C, the pressure distribution is shown for a device configuration according to that shown in FIGS. 4A-D (A) as well as the integrated device design shown in FIG. 13A (B). The integrated device design (bottom) is characterized by a reduction in inlet pressure of approximately 50%, and a reduction in device footprint by a factor of approximately 1.7. The increase in the pressure drop along with the increased durability of thermoplastic devices may facilitate the scalable manufacture, and self-starting of devices that produce aligned collagen sheets without the need for pulling.

The fluidic device shown in FIGS. 13A-F had the following properties:

Channel width (um): From outlet: 250, 350, 475, 625, 800 (Murray's Law, X=0.75*)

Dead volume of single layer: 152 mm^2*0.15 mm (channel depth)=22.8 mm^3=0.0228 mL, comparable to volume of 1 cm (w)×1 cm (L)×0.02 cm (d) sheet=0.02 mL (one cell layer of printed skin sheet, mouse)

Device footprint: 36 mm (width)×25 (length)

Target (aligned) sheet width: 15 mm

Target flow rate: Collagen: 400 ul/min, PEG: 4000 ul/min

Flow resistance in Collagen layer. Viscosity of Collagen solution at 23 C 74 cp Predicted inlet pressure: Inlet: 43587 Pa=0.436 atm, last bifurcation: 2908 Pa=0.0287 atm, Ratio=0.067=6.7% pressure drop Flow resistance in PEG layers. Viscosity of PEG solution at 23 C: 19 cp. Predicted inlet pressure: Inlet: 111953 Pa=1.104 atm, last bifurcation: 7220 Pa=0.071 atm, Ratio=0.067=6.7% pressure drop Inlet hole size and positions: 4×1.59 mm (1/16 inch) holes, 9 mm from top and edge, 9 mm distance from each hole Composition of fluid: Top & Bottom layer: Composition of fluid: Top & Bottom layer: 10% wt PEG, 35 kDa (pH 8), middle layer: 2-5 mg/ml lyophilized Collagen (pH 2)

Example 10

Fabrication of Engineered Living Blood Vessel

The fabrication of engineered vessels using either conventional cell sheet engineering or by seeding a biodegradable scaffold with SMCs currently requires 3 to 6 months to generate a vessel. In contrast, the devices and methods of the present disclosure may be employed to engineer living arterial substitutes on within approximately one week.

It was found that a suitable collagen sheet thickness for forming the arterial substitute as in the 3 μm range, as such ultrathin collagen sheets exhibited a suitably high elastic modulus for producing tubular constructs. According to the present example embodiment, SMCs derived from hiPSCs were seeded ($4\times10^4$ cells/cm$^2$) onto aligned, ultrathin (3 μm) collagen sheets (V*=4.5). The collagen sheets were dried over substrates, and through the use of a seeding well, SMCs were statistically seeded on the sheets through sedimentation. A suitable SMC seeding range was selected to produce a confluent monolayer. It was found that a surface density of approximately $4\times10^5$ cells/cm$^2$ was appropriate.

As the presently described implementation of the fluidic system employed a pH-triggered gelation of collagen, in which the acidic collagen (dissolved in pH 2) is combined with a basic phosphate solution (pH 8), cells were not readily incorporated into the polymer solution or the flow-confining solution, because neither of the solutions were cell-compatible. For this reason, the SMCs were externally seeded after formation of the polymer sheets. However, it is noted that the present external seeding method is not intended to be limiting, and that cell inclusion may be performed using the temperature-controlled device, for example, as described in Example 11 below. When a temperature-controlled device is employed, the gelation may be temperature-triggered and the collagen could be dissolved in neutral buffer (pH 7.4)

Figure 13D:
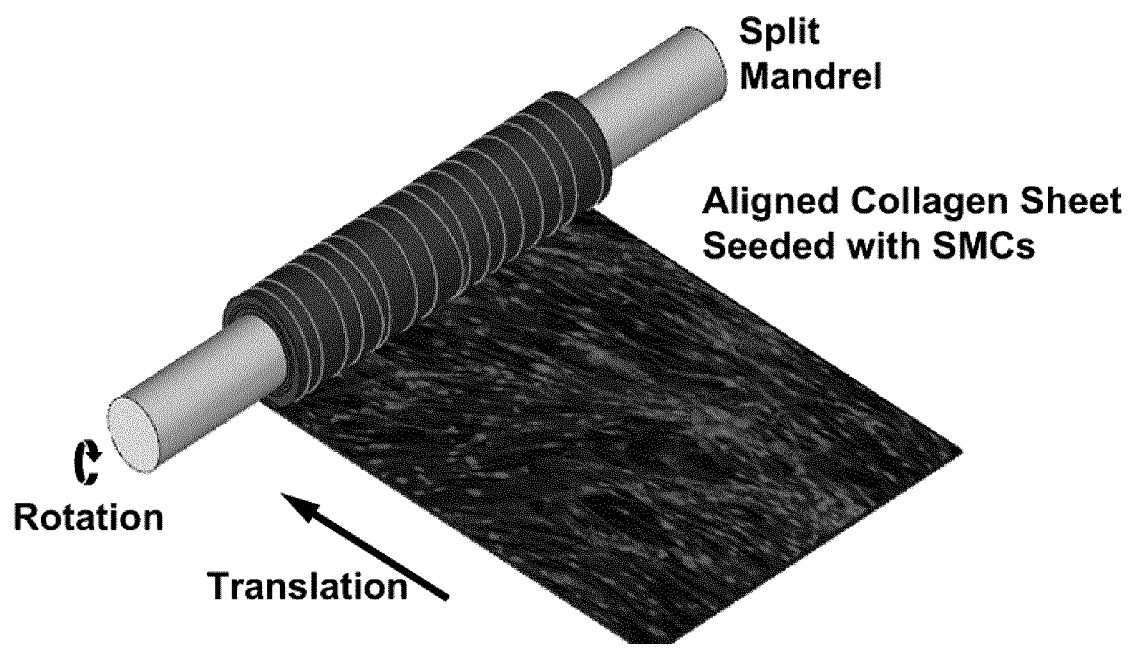
FIGS. 13D-F provide a schematic illustration and photographs of automated formation of arterial substitute (1.5 mm ID) based upon aligned collagen sheets with seeded smooth muscle cells. Custom designed and machined split mandrels were employed.
Figure 13E:
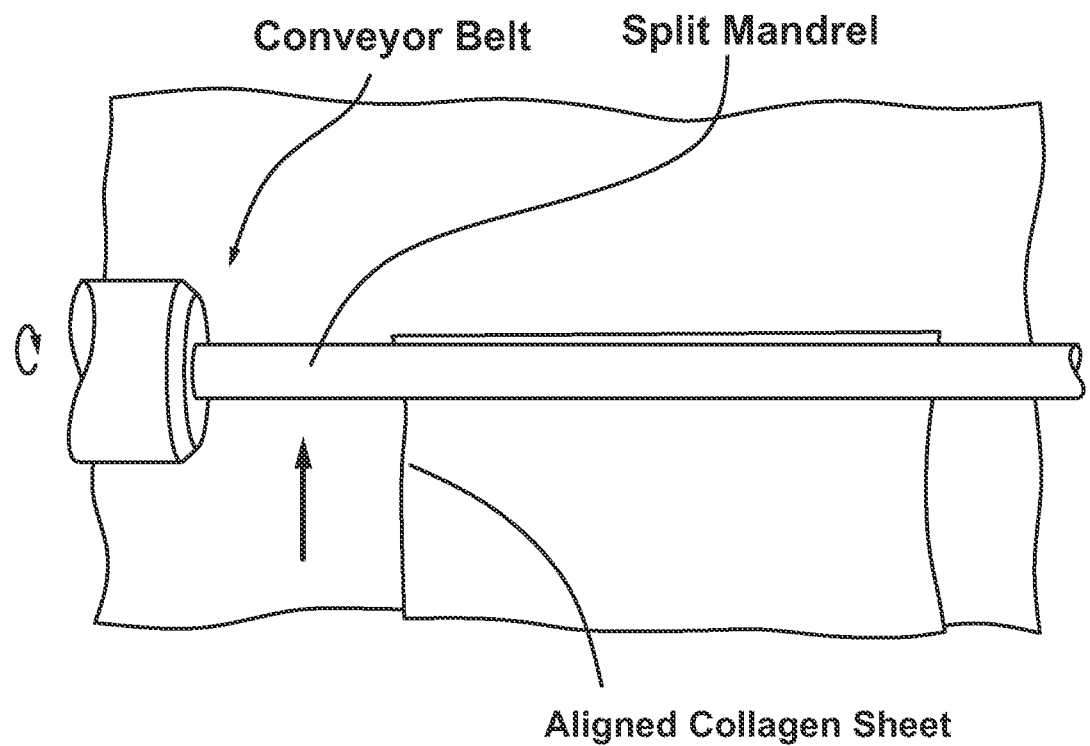
Figure 13F:
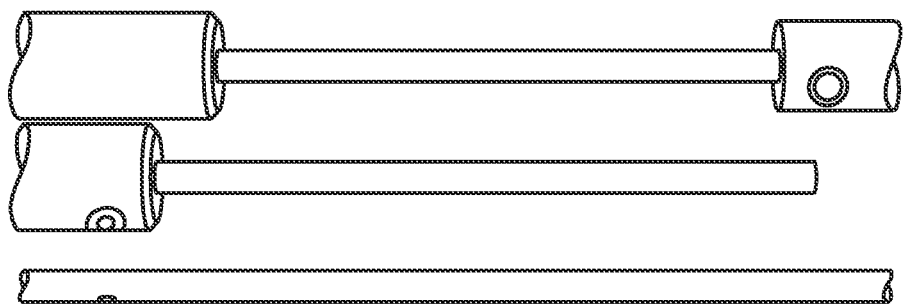

FIG. 13D shows a schematic of the automated formation of an arterial substitute (1.5 mm ID) based upon aligned collagen sheets with seeded smooth muscle cells. As shown in FIGS. 13E and 13F, split mandrels were employed for the collection of the collagen sheets. After a 4 h culture period, the sheet was rolled onto a mandrel, cultured for 7 d in medium supplemented with ascorbic acid and the lumen subsequently seeded with ECs derived from hiPSCs. The artificial vessel was removed from the mandrel using a split mandrel and removing each piece separately.

The engineered blood vessel was confirmed to recapitulate the lamellar ultrastructure typical of a native vessel wall, as shown in FIGS. 14A-B. Hematoxylin and eosin stained cross-section of the (A) murine aorta and an (B) engineered blood vessel. A lamellar ultrastructure consistent with alternating layers of SMCs and collagen was observed. Confocal fluorescence images of an engineered blood vessel were obtained. Cell nuclei and F-actin were imaged and demonstrated circumferential alignment of SMCs. Constructs produced with a 200 μm wall thickness displayed a burst pressure of 629±133 mmHg (mean±SD; n=6).

Example 11

Vascular Bioprinter for Automated Additive Preparation of Arterial Constructs

Figure 15A:
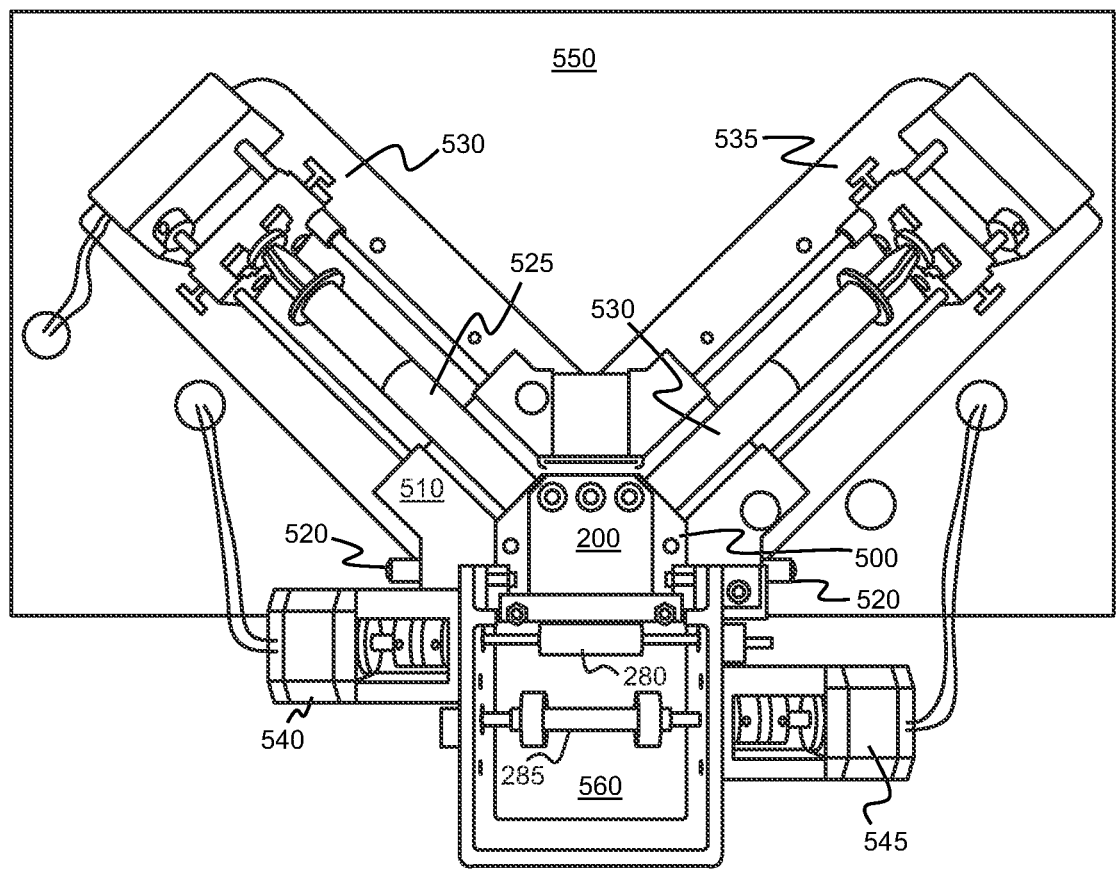
FIGS. 15A-D show aspects of a vascular bioprinter for automated additive preparation of arterial constructs.

FIG. 15A shows a photograph of one example embodiment of an assembled vascular bioprinter for automated additive preparation of arterial constructs. As shown in the figure, a machined and assembled control unit 500 is provided for vascular bioprinting, allowing for the temperature of the printer cartridge to be controlled. The assembly of the present example vascular bioprinter employs a bottom up approach. The temperature control 510 unit has a pocket milled out to house the TE element. The cold side of the TE element faces the fluid control unit 500 to actively cool the flow control unit 500 to 4° C., which in turn cools the microfluidic device 200 that is placed above the flow control unit 500. The temperature control unit is also connected at 520 to a recirculating water bath maintained at 37° C. to remove the excessive heat from the unit. The cooling jackets 525 and 530 around the syringe pumps 530 and 535 maintain the polymer solutions at 4° C. The flow through the flow unit 500 is controlled by the syringe pumps 530 and 535. The temperature controller 510, fluid flow controller 500 and the stepper motor drivers 540 and 545 to rotate the mandrels are all housed in the electrical enclosure 550. As per the previously described example embodiments, aligned biomaterial sheets emerge from the flow-focusing region of the device into a liquid filled reservoir 560, where they are guided over a first rotating collection device 280, and further for assembly onto an optional second rotating collection device 282.

Figure 15B:
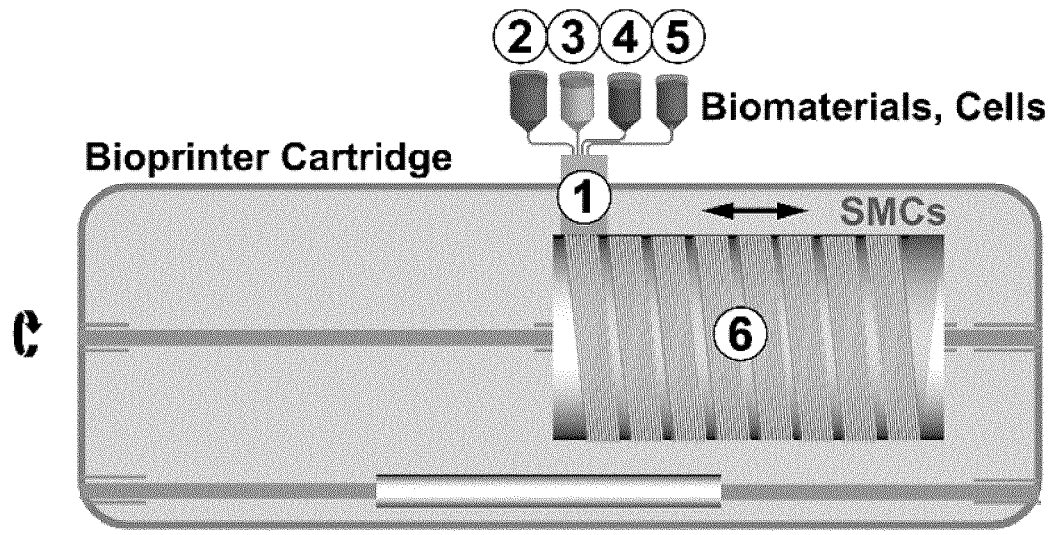
Figure 15C:
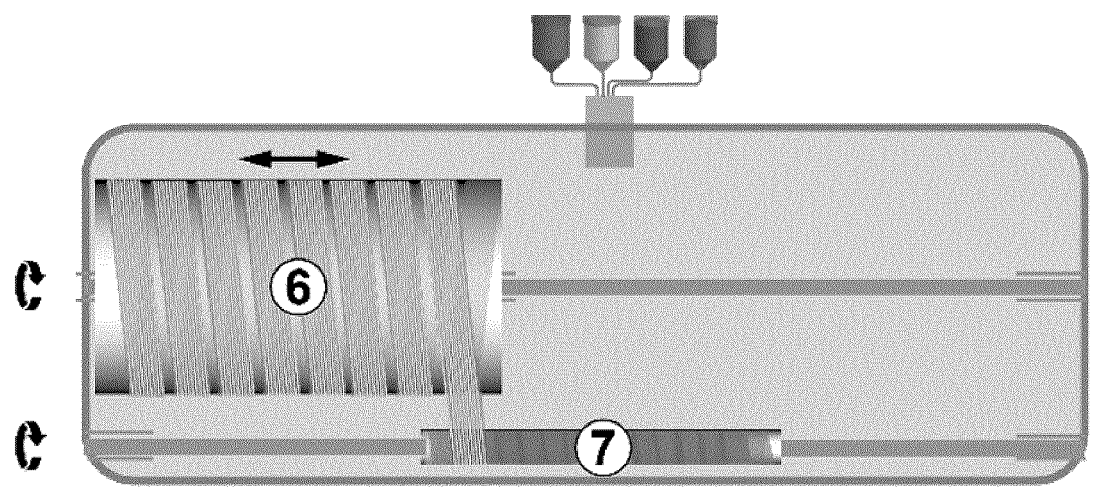
Figure 15D:
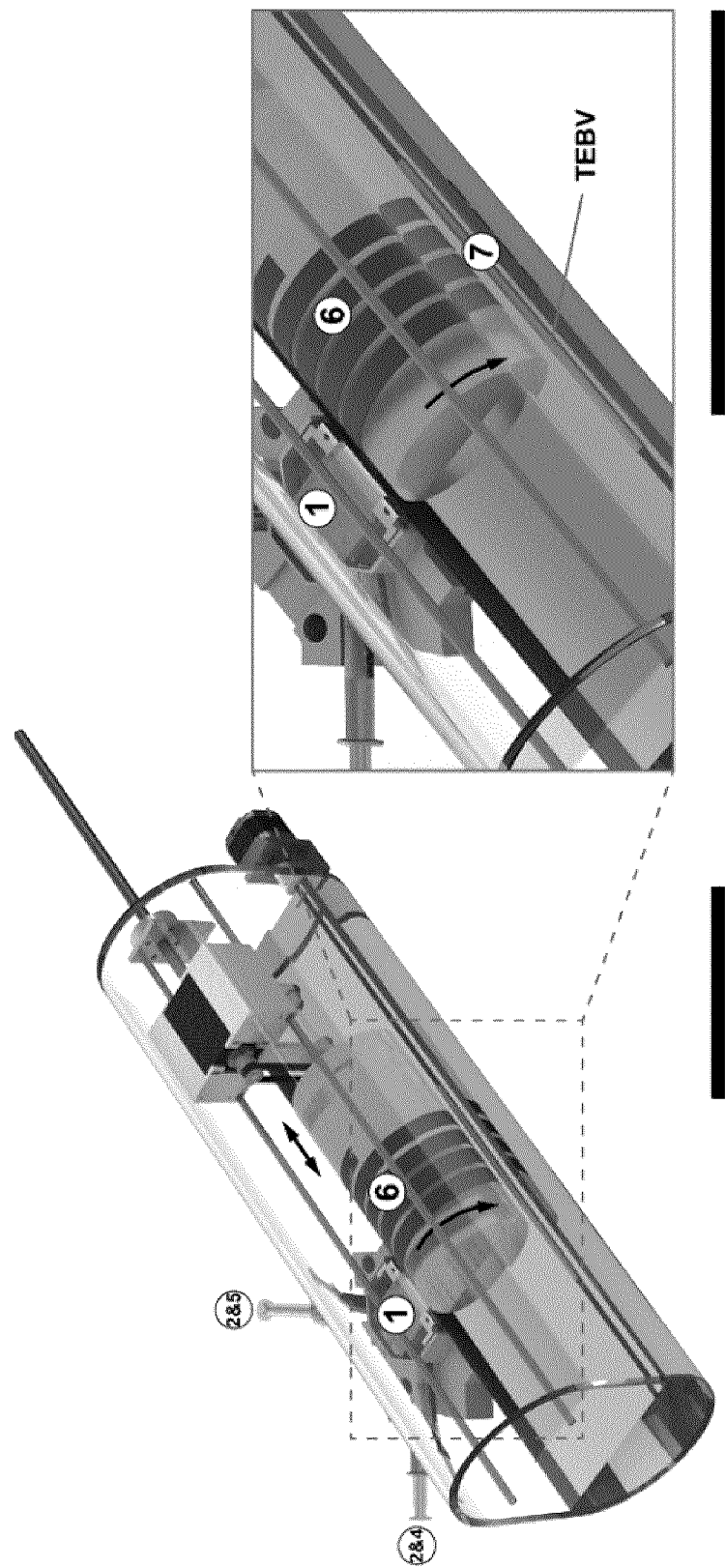

Referring now to the example embodiment shown in FIGS. 15B-D, the biopolymer and cell containing solutions, microfluidic portion and flow-focusing conduit, the first rotating collection device, and the second rotating collection device, are shown as components of a vascular bioprinter device. As shown in the figure, two or more components of the device may be provided in the form of a cartridge. According to one example method, tissue-engineered blood vessels are obtained in a multi-step process that is schematically illustrated in FIGS. 15B-D.

As shown in FIGS. 15B-D, the example device includes a print head (1) configured for the formation of an aligned collagen sheet, according to the example embodiments described above. For example, the print head may be an integrated or hybrid multilayer fluidic device that includes a microfluidic distribution network for generating layered flow of a polymer liquid sheet sandwiched between respective sheets of flow-confining liquid, and a flow-focusing region for inducing alignment in the polymer liquid sheet prior to, or during, its solidification, as described in the preceding example embodiments.

The print head (1) produces an aligned collagen sheet. For example, aligned collagen sheets are initially formed by the print head (1) from acidic collagen solution, according to the methods described above, and collected onto a first rotating collection device (6). The first rotating collection device (6) may, for example, possess the shape of a cylinder (as shown in the figure) or the form of another shape or structure suitable for collection, such as a fork. During sheet formation and collection, the first collection device (6) is translated during rotation in the axial direction with respect to the print head (1). The translation and rotation may be configured such that the pitch exceeds the sheet width, e.g., so that the sheet is collected on the first collection device without overlap. In the case that the first collection device has a cylindrical shape, its diameter may be, for example, between 5 mm and 300 mm and its length may be, for example, between 50 mm and 500 mm. The surface area of the first collection device will allow for the continuous deposition of aligned collagen sheets with lengths between 50 mm and 7,000 mm.

After deposition at the first collection device (6), the sheet may be further processed according one or more protocols, e.g., by placement in fibril incubation buffer and subsequent drying.

In a second deposition, step a second biopolymer sheet may be deposited on top of the aligned collagen sheet that was collected onto the first collection device (6) in order to form a second layer. The second layer may be solidified onto the first layer (the aligned collagen sheet) via temperature-induced gelation of cell containing neutral pH collagen solution. This deposition step may be performed by employing the print head (1) to dispense additional biomaterial liquids onto the collagen sheet that was previously collected onto the first collection device (6) while translating the print head (1) relative to the first collection device (6). For example, the additional biomaterials may include SMCs and other biopolymers, such as elastin. Biopolymer and cell containing solutions (2-5) are controllably supplied to the print head (1) to form the cell-collagen sheet construct on the first collection device (6).

After gelation, the bi-layered sheet may be transferred to a second collection device (7) to define a tissue-engineered blood vessel. The deposition onto the second collection device may be conducted, for example, with an overlap between 10% and 90%. By overlapping multiple bilayers, a large number of deposited layers may be employed to produce a tissue engineered blood vessel with clinically relevant inner diameter, wall thickness, length, burst pressure, suture retention strength, and compliance.

FIG. 15D provides a rendered 3D design drawing of an example vascular bioprinter cartridge (to scale; scale bars are 200 mm (left and right)). In order to facilitate scalable manufacturing, one or more of the components of the integrated device (e.g. cartridge) may be produced using thermoplastic substrates by commercial processes, e.g., injection molding in conjunction with hot embossing, carbon dioxide laser micromachining, and thermal bonding. In some example implementations, a bioprinter cartridge may be supplied in a single-use, sterile pack, in a format similar to that of commercial laser printer cartridges.

It will be understood that although the preceding examples pertain to the fabrication of artificial blood vessels, various embodiments of the present disclosure may be adapted to form other types of tubular tissue structures. For example, in addition to tissue engineered arteries and veins, additional non-limiting examples of tissue engineered multilayer hollow tubes include lymphatic vessels, ureter, trachea, esophagus, and intestine. It will also be understood that artificial tubular structures need not be hollow in other adaptations of the embodiments disclosed herein, For example, a non-limiting example of a solid tissue engineered tubular structure is a tendon.

Figure 16A:
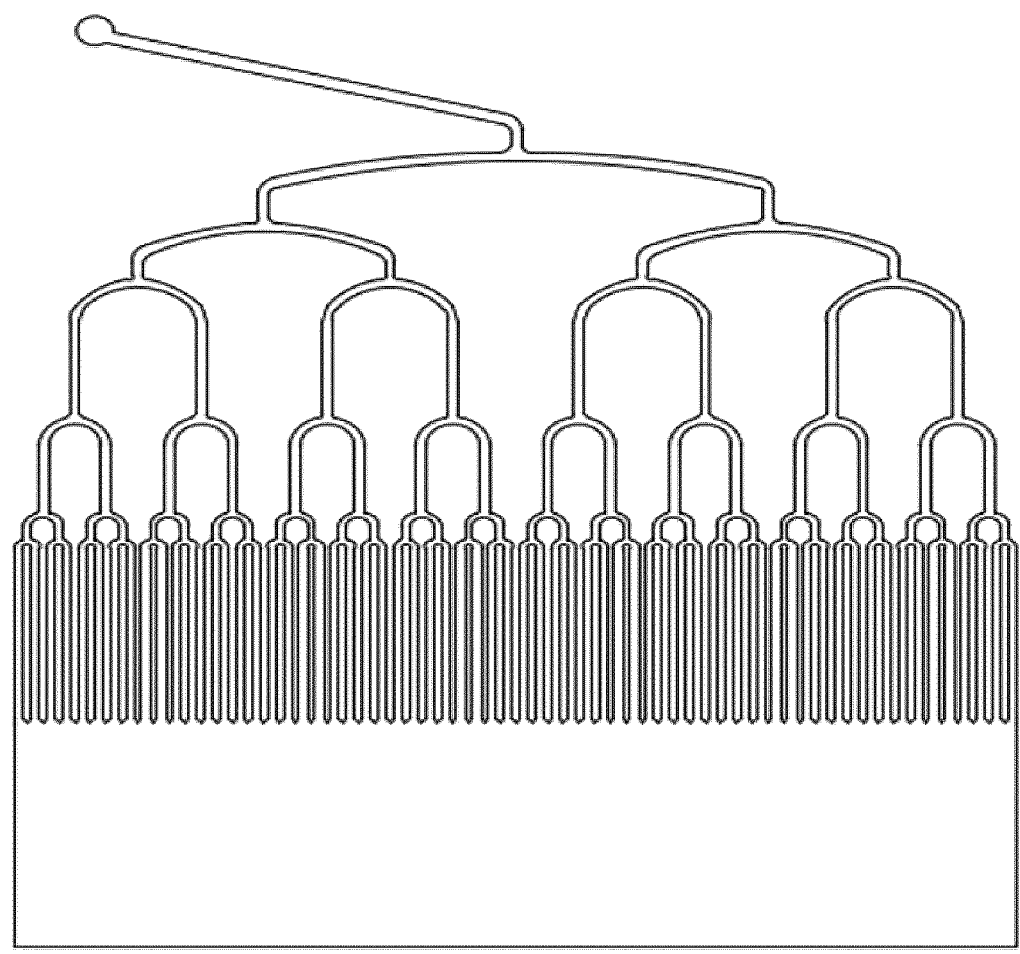
FIGS. 16A-C show various example designs of the microfluidic portion of the fluidic device.
Figure 16B:
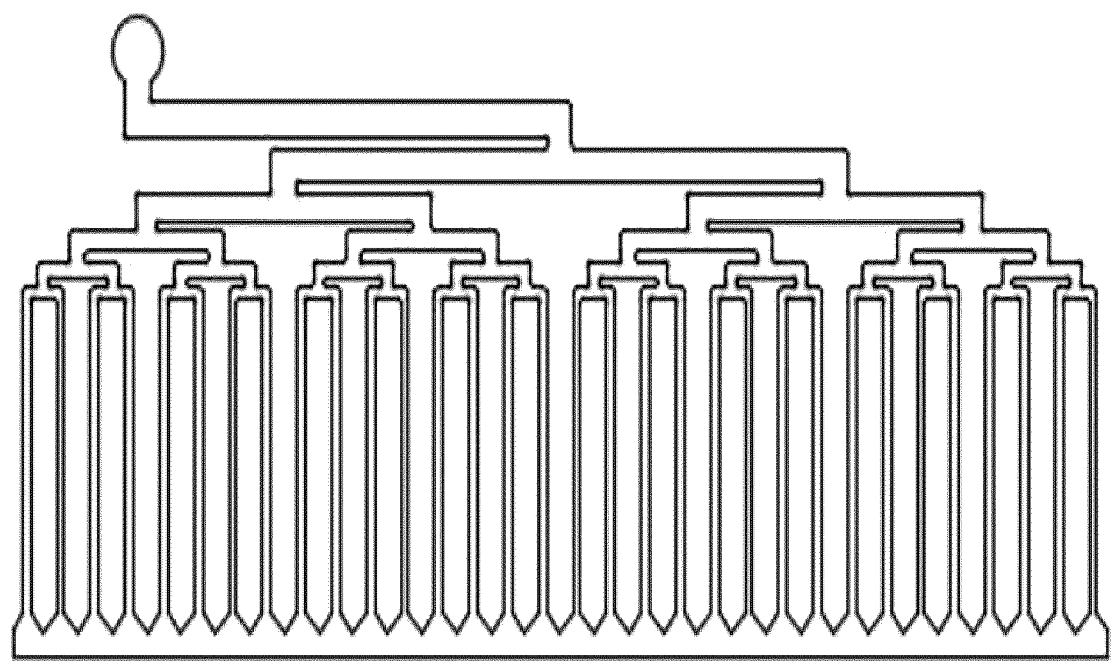
Figure 16C:
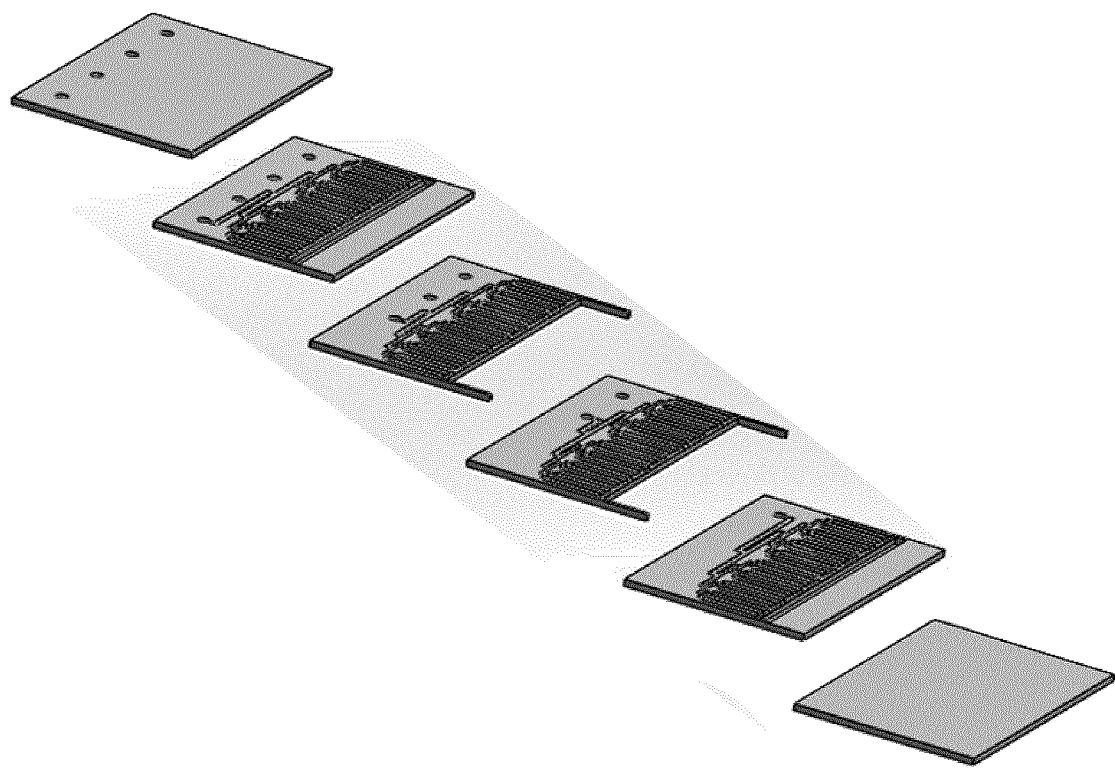

FIGS. 16A-C show various example designs of the microfluidic portion of the fluidic device. FIG. 16A shows a first-generation microfluidic chip, with channel width ranging from 300 to 400 um, dead volume of 0.049 mL, and device footprint of 37.95 mm×40 mm. FIG. 16B shows a second-generation of microfluidic chip, with channel widths obeying Murray's Law, ranging from 250 to 800 um, dead volume of 0.0228 mL, and a device footprint of 46 mm×25 mm.

FIG. 16C shows an exploded view of the multi-layered bonding of multiple-layered devices, with each layer being 1 mm in thickness. Each layer has features that are 150 um in depth, embossed or injection molded using a silicon wafer mold. The top layer, which serves as a lid for the microfluidic device, includes four holes as inlets for biopolymer delivery. The second layer is the first flow-confining layer which contains a 1.5 mm gap where the flow-confining fluid will be directed from the top to the layer below. The third layer is the polymer solution distribution layer, where there is a 5 mm constriction to enable the solution to be delivered through the microfluidic device but constrained by the focusing solution from the second and fifth layer. The fourth layer is an optional distribution layer that enables the delivery of one or more additional solutions (e.g. an additional polymer solution for forming an additional layer). The fifth layer is the second flow-confining layer which contains the 1.5 mm bottom gap that forces the flow-confining to be directed from the bottom to the layer above. Lastly, the sixth layer serves as the bottom lid for the microfluidic device.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

REFERENCES

1 Boland, E. D. et al. Electrospinning collagen and elastin: Preliminary vascular tissue engineering. *Frontiers in Bioscience* 9, 1422-1432, doi:10.2741/1313 (2004).

2 Ottani, V., Raspanti, M. & Ruggeri, A. Collagen structure and functional implications. *Micron* 32, 251-260, doi: 10.1016/s0968-4328(00)00042-1 (2001).

3 Muller, L. J., Marfurt, C. F., Kruse, F. & Tervo, T. M. T. Corneal nerves: structure, contents and function. *Exp. Eye Res.* 76, 521-542, doi:10.1016/s0014-4835(03)00050-2 (2003).

4 Ruberti, J. W., Roy, A. S. & Roberts, C. J. in *Annual Review of Biomedical Engineering, Vol* 13 Vol. 13 *Annual Review of Biomedical Engineering* (eds M. L. Yarmush, J. S. Duncan, & M. L. Gray) 269-295 (2011).

5 Muller, L. J., Pels, E. & Vrensen, G. The specific architecture of the anterior stroma accounts for maintenance of corneal curvature. *British Journal of Ophthalmology* 85, 437-443, doi:10.1136/bjo.85.4.437 (2001).

6 Mackenzie, I. C. & Hill, M. W. Connective-tissue influences on patterns of epithelial architecture and keratinization in skin and oral-mucosa of the adult-mouse. *Cell and Tissue Research* 235, 551-559 (1984).

7 Verhaegen, P. et al. Differences in collagen architecture between keloid, hypertrophic scar, normotrophic scar, and normal skin: An objective histopathological analysis. *Wound Repair and Regeneration* 17, 649-656, doi: 10.1111/j.1524-475X.2009.00533.x (2009).

8 Chen, X., Nadiarynkh, O., Plotnikov, S. & Campagnola, P. J. Second harmonic generation microscopy for quantitative analysis of collagen fibrillar structure. *Nature Protocols* 7, 654-669, doi:10.1038/nprot.2012.009 (2012).

9 Birk, D. E. & Trelstad, R. L. Extracellular compartments in tendon morphogenesis—collagen fibril, bundle, and macroaggregate formation. *Journal of Cell Biology* 103, 231-240, doi:10.1083/jcb.103.1.231 (1986).

10 Sharma, P. & Maffulli, N. Current concepts review tendon injury and tendinopathy: Healing and repair. *Journal of Bone and Joint Surgery-American Volume* 87A, 187-202, doi:10.2106/jbjs.d.01850 (2005).

11 Fratzl, P. & Weinkamer, R. Nature's hierarchical materials. *Progress in Materials Science* 52, 1263-1334, doi: 10.1016/j.pmatsci.2007.06.001 (2007).

12 Wang, N., Liu, W., Huang, J. & Ma, K. The structure-mechanical relationship of palm vascular tissue. *Journal of the mechanical behavior of biomedical materials* 36, 1-11, doi:10.1016/j.jmbbm.2014.04.001 (2014).

13 Hutmacher, D. W. Scaffold design and fabrication technologies for engineering tissues—state of the art and future perspectives. *J. Biomater. Sci.-Polym. Ed.* 12, 107-124, doi:10.1163/156856201744489 (2001).

14 Holmes, D. F. et al. Corneal collagen fibril structure in three dimensions: Structural insights into fibril assembly, mechanical properties, and tissue organization. *Proceedings of the National Academy of Sciences of the United States of America* 98, 7307-7312, doi:10.1073/pnas.111150598 (2001).

15 Gelse, K., Poschl, E. & Aigner, T. Collagens—structure, function, and biosynthesis. *Advanced Drug Delivery Reviews* 55, 1531-1546, doi:10.1016/j.addr.2003.08.002 (2003).

16 Zhao, J.-Y. et al. Influence of hyaluronic acid on wound healing using composite porcine acellular dermal matrix grafts and autologous skin in rabbits. *International Wound Journal* 10, 562-572, doi:10.1111/j.1742-481X.2012.01023.x (2013).

17 Brodsky, B., Eikenberry, E. F. & Cassidy, K. Unusual collagen periodicity in skin. *Biochimica Et Biophysica Acta* 621, 162-166, doi:10.1016/0005-2795(80)90072-0 (1980).

18 Hofmann, H., Fietzek, P. P. & Kuhn, K. Role of polar and hydrophobic interactions for molecular packing of type-I collagen—3-dimensional evaluation of amino-acid sequence. *Journal of Molecular Biology* 125, 137-165, doi:10.1016/0022-2836(78)90342-x (1978).

19 Amiel, D., Frank, C., Harwood, F., Fronek, J. & Akeson, W. Tendons and ligaments: A morphological and biochemical comparison. *Journal of Orthopaedic Research* 1, 257-265 (1984).

20 Diamant, J., Arridge, R. G. C., Baer, E., Litt, M. & Keller, A. Collagen-ultrastructure and its relation to mechanical properties as a function of aging. *Proceedings of the Royal Society Series B-Biological Sciences* 180, 293-+, doi:10.1098/rspb.1972.0019 (1972).

21 Komai, Y. & Ushiki, T. The 3-dimensional organization of collagen fibrils in the human cornea and sclera. *Investigative Ophthalmology & Visual Science* 32, 2244-2258 (1991).

22 Beenakker, J. W. M., Ashcroft, B. A., Lindeman, J. H. N. & Oosterkamp, T. H. Mechanical properties of the extracellular matrix of the aorta studied by enzymatic treatments. *Biophysical Journal* 8, 1731-1737 (2012).

23 Canham, P. B., Finlay, H. M. & Boughner, D. R. Contrasting structure of the saphenous vein and internal mammary artery used as coronary bypass vessels. *Cardiovascular Research* 34, 557-567, doi:10.1016/s0008-6363(97)00056-4 (1997).

24 Shadwick, R. E. Mechanical design in arteries. *Journal of Experimental Biology* 202, 3305-3313 (1999).

25 Berillis, P. The role of collagen in the aorta's structure. *The Open Circulation and Vascular Journal* 6, 1-8 (2013).

26 Wollensak, G., Spoerl, E. & Seiler, T. Stress-strain measurements of human and porcine corneas after riboflavin-ultraviolet-A-induced cross-linking. *Journal of Cataract and Refractive Surgery* 29, 1780-1785, doi:10.1016/s0886-3350(03)00407-3 (2003).

27 Rafat, M. et al. PEG-stabilized carbodiimide crosslinked collagen-chitosan hydrogels for corneal tissue engineering. *Biomaterials* 29, 3960-3972, doi:10.1016/j.biomaterials.2008.06.017 (2008).

28 Weinberg, C. B. & Bell, E. A blood vessel model constructed from collagen and cultured vascular cells. *Science* 231, 397-400 (1986).

29 L'Heureux, N., Pâquet, S., Labbé, R., Germain, L. & Auger, F. A. A completely biological tissue-engineered human blood vessel. *FASEB J.* 12, 47-56 (1998).

30 Berglund, J. D., Mohseni, M. M., Nerem, R. M. & Sambanis, A. A biological hybrid model for collagen-based tissue engineered vascular constructs. *Biomaterials* 24, 1241-1254 (2003).

31 Caves, J. M. et al. Fibrillogenesis in Continuously Spun Synthetic Collagen Fiber. *Journal of Biomedical Materials Research Part B-Applied Biomaterials* 93B, 24-38, doi:10.1002/jbm.b.31555 (2010).

32 Koester, S., Evans, H. M., Wong, J. Y. & Pfohl, T. An in situ study of collagen self-assembly processes. *Biomacromolecules* 9, 199-207, doi:10.1021/bm700973t (2008).

33 Hakansson, K. M. O. et al. Hydrodynamic alignment and assembly of nanofibrils resulting in strong cellulose filaments. *Nature Communications* 5, doi:10.1038/ncomms5018 (2014).

34 Lanfer, B. et al. Aligned fibrillar collagen matrices obtained by shear flow deposition. *Biomaterials* 29, 3888-3895, doi:10.1016/j.biomaterials.2008.06.016 (2008).

35 Lai, E. S., Huang, N. F., Cooke, J. P. & Fuller, G. G. Aligned nanofibrillar collagen regulates endothelial organization and migration. *Regenerative Medicine* 7, 649-661, doi:10.2217/rme.12.48 (2012).

36 Eastwood, M., Porter, R., Khan, U., McGrouther, G. & Brown, R. Quantitative analysis of collagen gel contractile forces generated by dermal fibroblasts and the relationship to cell morphology. *Journal of Cellular Physiology* 166, 33-42, doi:10.1002/(sici)1097-4652(199601)166:1<33::aid-jcp4>3.0.co;2-h (1996).

37 Thomopoulos, S., Fomovsky, G. M. & Holmes, J. W. The development of structural and mechanical anisotropy in fibroblast populated collagen gels. *Journal of Biomechanical Engineering-Transactions of the Asme* 127, 742-750, doi:10.1115/1.1992525 (2005).

38 Lee, P., Lin, R., Moon, J. & Lee, L. P. Microfluidic alignment of collagen fibers for in vitro cell culture. *Biomedical Microdevices* 8, 35-41, doi:10.1007/s10544-006-6380-z (2006).

39 Cheng, X. et al. An electrochemical fabrication process for the assembly of anisotropically oriented collagen bundles. *Biomaterials* 29, 3278-3288, doi:10.1016/j.biomaterials.2008.04.028 (2008).

40 Xu, B., Chow, M.-J. & Zhang, Y. Experimental and modeling study of collagen scaffolds with the effects of crosslinking and fiber alignment. *International journal of biomaterials* 2011, 172389-172389, doi:10.1155/2011/172389 (2011).

41 Guo, C. & Kaufman, L. J. Flow and magnetic field induced collagen alignment. *Biomaterials* 28, 1105-1114, doi:10.1016/j.biomaterials.2006.10.010 (2007).

42 Novak, T., Shannon, G., Mousoulis, C., Voytik-Harbin, S. L. & Neu, C. P. Controlled fibrillogenesis for improved magnetic alignment of collagen. *J. Tissue Eng. Regen. Med.* 8, 268-269 (2014).

43 Torbet, J. & Ronziere, M. C. Magnetic alignment of collagen during self-assembly. *Biochem. J.* 219, 1057-1059 (1984).

44 Barocas, V. H., Girton, T. S. & Tranquillo, R. T. Engineered alignment in media equivalents: Magnetic prealignment and Mandrel compaction. *Journal of Biomechanical Engineering-Transactions of the Asme* 120, 660-666, doi:10.1115/1.2834759 (1998).

45 Torbet, J. et al. Orthogonal scaffold of magnetically aligned collagen lamellae for corneal stroma reconstruction. *Biomaterials* 28, 4268-4276, doi:10.1016/j.biomaterials.2007.05.024 (2007).

46 Oryan, A., Moshiri, A. & Meimandi-Parizi, A. In vitro characterization of a novel tissue engineered based hybridized nano and micro structured collagen implant and its in vivo role on tenoinduction, tenoconduction, tenogenesis and tenointegration. *Journal of Materials Science-Materials in Medicine* 25, 873-897, doi:10.1007/s10856-013-5110-3 (2014).

47 Zhong, S. P. et al. An aligned nanofibrous collagen scaffold by electrospinning and its effects on in vitro fibroblast culture. *J. Biomed. Mater. Res. Part A* 79A, 456-463, doi:10.1002/jbm.a.30870 (2006).

48 Xie, J. W., Li, X. R. & Xia, Y. N. Putting Electrospun Nanofibers to Work for Biomedical Research. *Macromol. Rapid Commun.* 29, 1775-1792, doi:10.1002/marc.200800381 (2008).

49 Dahl, S. L. M., Vaughn, M. E. & Niklason, L. E. An ultrastructural analysis of collagen in tissue engineered arteries. *Annals of Biomedical Engineering* 35, 1749-1755, doi:10.1007/s10439-007-9340-8 (2007).

50 Dahl, S. L. M., Rhim, C., Song, Y. C. & Niklason, L. E. Mechanical properties and compositions of tissue engineered and native arteries. *Annals of Biomedical Engineering* 35, 348-355, doi:10.1007/s10439-006-9226-1 (2007).

51 McDonald, J. C. et al. Fabrication of microfluidic systems in poly(dimethylsiloxane). *Electrophoresis* 21, 27-40 (2000).

52 Gervais, T., El-Ali, J., Gunther, A. & Jensen, K. F. Flow-induced deformation of shallow microfluidic channels. *Lab on a Chip* 6, 500-507, doi:10.1039/b513524a (2006).

53 Cuneo, P., Magri, E., Verzola, A. & Grazi, E. Macromolecular crowding is a primary factor in the organization of the cytoskeleton. *Biochem. J.* 281, 507-512 (1992).

54 Zhou, H. X., Rivas, G. & Minton, A. P. Macromolecular crowding and confinement: biochemical, biophysical, and potential physiological consequences. *Annual Review Biophysics* 37, 375-397 (2008).

55 Minton, A. P. The influence of macromolecular crowding and macromolecular confinement on biochemical reactions in physiological media. *Journal of Biological Chemistry* 276, 10577-10580 (2001).

56 Saeidi, N. et al. Molecular crowding of collagen: A pathway to produce highly-organized collagenous structures. *Biomaterials* 33, 7366-7374, doi:10.1016/j.biomaterials.2012.06.041 (2012).

57 Cavallaro, J. F., Kemp, P. D. & Kraus, K. H. Collagen fabrics as biomaterials. *Biotechnology and Bioengineering* 44, 146 (1994).

58 Paten, J. A. et al. Utility of an optically-based, micromechanical system for printing collagen fibers. *Biomaterials* 34, 2577-2587, doi:10.1016/j.biomaterials.2012.12.028 (2013).

59 Kemp, P. D., Cavallaro, J. F. & Hastings, D. N. Effects of carbodiimide crosslinking and load environment on the remodeling of collagen scaffolds. *Tissue Engineering* 1, 71-79 (1995).

60 Zeugolis, D. I., Paul, R. G. & Attenburrow, G. Extruded collagen fibres for tissue-engineering applications: influence of collagen concentration and NaCl amount. *J. Biomater. Sci.-Polym. Ed.* 20, 219-234 (2009).

61 Goublomme, A., Draily, B. & Crochet, M. J. Numerical prediction of extrudate swell of a high-density polyethylene. *J. Non-Newton. Fluid Mech.* 44, 171-195, doi:10.1016/0377-0257(92)80050-8 (1992).

62 Mitsoulis, E., Abdali, S. S. & Markatos, N. C. Flow simulation of herschel-bulkley fluids through extrusion dies. *Can. J. Chem. Eng.* 71, 147-160 (1993).

63 Kumar, V. A. C., J. M.; Haller, C. A.; Dai, E.; Liu, L.; Grainger, S.; Chaikof, E. L. Acellular vascular grafts generated from collagen and elastin analogs. *Acta biomaterialia* 9, 8067-8074 (2013).

64 Wanjare, M., Kuo, F. & Gerecht, S. Derivation and maturation of synthetic and contractile vascular smooth muscle cells from human pluripotent stem cells. *Cardiovascular Research* 97, 321-330 (2013).

65 Silver, F. H. & Trelstad, R. L. Type-I collagen in solution-structure and properties of fibril fragments. *Journal of Biological Chemistry* 255, 9427-9433 (1980).

66 Saeidi, N., Sander, E. A. & Ruberti, J. W. Dynamic shear-influenced collagen self-assembly. *Biomaterials* 30, 6581-6592, doi:10.1016/j.biomaterials.2009.07.070 (2009).

67 Caves, J. M. et al. The use of microfiber composites of elastin-like protein matrix reinforced with synthetic collagen in the design of vascular grafts. *Biomaterials* 31, 7175-7182, doi:10.1016/j.biomaterials.2010.05.014 (2010).

68 Kumar, V. A. et al. Acellular vascular grafts generated from collagen and elastin analogs. *Acta biomaterialia* 9, 8067-8074, doi:10.1016/j.actbio.2013.05.024 (2013).

69 Levesque, M. J., Liepsch, D., Moravec, S. & Nerem, R. M. Correlation of endothelial-cell shape and wall shear-stress in a stenosed dog aorta. *Arteriosclerosis* 6, 220-229 (1986).

70 Cicchi, R. et al. From molecular structure to tissue architecture: collagen organization probed by SHG microscopy. *Journal of Biophotonics* 6, 129-142, doi:10.1002/jbio.201200092 (2013).

71 Daxer, A., Misof, K., Grabner, B., Ettl, A. & Fratzl, P. Collagen fibrils in the human corneal stroma: Structure and aging. *Investigative Ophthalmology & Visual Science* 39, 644-648 (1998).

72 Achilli, M. & Mantovani, D. Tailoring mechanical properties of collagen-based scaffolds for vascular tissue engineering: the effects of pH, temperature and ionic strength on gelation. *Polymers* 2, 664-680, doi:10.3390/polym2040664 (2010).

Therefore what is claimed is:

1. A fluidic device for forming a polymer sheet from a polymer liquid while applying flow constriction thereto, comprising:

a polymer distribution fluidic network comprising a plurality of polymer distribution microfluidic or mesofluidic channels, said polymer distribution microfluidic or mesofluidic channels comprising laterally arrayed outlets arranged to form the polymer solution liquid sheet when a polymer solution is provided to a proximal inlet of said polymer distribution fluidic network;

a first flow-confining distribution fluidic network comprising a plurality of first flow-confining microfluidic or mesofluidic channels, said first flow-confining microfluidic or mesofluidic channels comprising laterally arrayed outlets arranged to form a first flow-confining liquid sheet when a flow-confining solution is provided to a proximal inlet of said first flow-confining distribution fluidic network;

a second flow-confining distribution fluidic network comprising a plurality of second flow-confining microfluidic or mesofluidic channels, said second flow-confining microfluidic or mesofluidic channels comprising laterally arrayed outlets arranged to form a second flow-confining liquid sheet when the flow-confining solution is provided to a proximal inlet of said second flow-confining distribution fluidic network;

a first flow conduit having an inlet in flow communication with said laterally arrayed outlets of said polymer distribution fluidic network, said laterally arrayed outlets of said first flow-confining distribution fluidic network and said laterally arrayed outlets of said second flow-confining distribution fluidic network, wherein distal portions of said polymer distribution fluidic network, said first flow-confining distribution fluidic network and said second flow-confining distribution fluidic network are arranged in a stacked configuration along a stacking direction, such that a layered flow is formed within said first flow conduit when the flow-confining solution is provided to said proximal inlets of said first flow-confining distribution fluidic network and said second flow-confining distribution fluidic network, the layered flow comprising the polymer solution liquid sheet, contacted and sheathed on opposing sides thereof by the first flow-confining liquid sheet and the second flow-confining liquid sheet; and a second flow conduit having an inlet in flow communication with an outlet of said first flow conduit, said second flow conduit having a height, as determined along the stacking direction, that is less than the height of said first flow conduit, and said second flow conduit having a cross-sectional area, perpendicular to a flow direction, that is less than a cross-sectional area of said first flow conduit, the second flow conduit thereby forming a flow constriction suitable for reducing a thickness of the polymer liquid sheet via hydrodynamic focusing as the layered flow flows into and through said second flow conduit.

2. The fluidic device according to claim 1 wherein the height of the first flow conduit is greater than an initial thickness of the layered flow.

3. The fluidic device according to claim 1 wherein said polymer distribution fluidic network, said first flow-confining distribution fluidic network and said second flow-confining distribution fluidic network are provided in a microfluidic device; and wherein said first flow conduit and said second flow conduit are provided in a flow-focusing unit that is interfaced to said microfluidic device.

4. The fluidic device according to claim 1 wherein said polymer distribution fluidic network, said first flow-confining distribution fluidic network and said second flow-confining distribution fluidic network are provided in a microfluidic device; and wherein said first flow conduit and said second flow conduit are provided in a flow-focusing unit that is integrally formed with said microfluidic device.

5. The fluidic device according to claim 1 further comprising a third flow conduit in flow communication with said second flow conduit, wherein a height of said third flow conduit is greater than the height of the second flow conduit.

6. The fluidic device according to claim 1 wherein the height of said second flow conduit decreases from a proximal region thereof to a distal region thereof.

7. A method of forming an anisotropic polymer material, the method comprising:
providing a fluidic device according to claim 1;
flowing the polymer solution into said polymer distribution fluidic network at a first controlled rate;

flowing the flow-confining solution into the first flow-confining distribution fluidic network and the second flow-confining distribution fluidic network at a second controlled rate;

wherein a composition of the polymer solution is selected such that at least an outer portion of the polymer solution liquid sheet is hardened as the polymer solution liquid sheet flows through the second flow conduit, thereby forming a polymer sheet; and extracting the polymer sheet under applied tension, wherein the applied tension and confinement provided by the second flow conduit are selected such that the collected polymer sheet exhibits anisotropic properties.

8. The method according to claim 7 wherein the flow-confining solution is selected such that the polymer solution is cross-linked upon contact therewith.

9. The method according to claim 8 wherein the polymer solution is a collagen solution, and wherein the polymer sheet is an aligned collagen sheet.

10. The method according to claim 9 wherein the flow-confining solution is a polyethylene glycol solution.

11. The method according to claim 9 further comprising:
collecting the aligned collagen sheet on a rotating collection device in the absence of overlap of the aligned collagen sheet;
seeding the aligned collagen sheet with smooth muscle cells and culturing the smooth muscle cells on the aligned collagen sheet; and
collecting the seeded aligned collagen sheet onto a rotating mandrel.

12. The method according to claim 9 further comprising:
collecting the aligned collagen sheet on a rotating collection device in the absence of overlap of the aligned collagen sheet;
employing the fluidic device to deposit a second collagen layer onto the aligned collagen sheet, the second collagen layer comprising smooth muscle cells, thereby forming a collagen bilayer; and
collecting the collagen bilayer onto a rotating mandrel.

13. The method according to claim 12 wherein the second collagen layer is deposited onto the aligned collagen sheet while the aligned collagen sheet is retained on the rotating collection device.

14. The method according to claim 12 further comprising contacting the aligned collagen sheet with a fibril incubation buffer and drying the aligned collagen sheet prior to depositing the second collagen layer onto the aligned collagen sheet.

15. The method according to claim 9 wherein the first controlled rate and the second controlled rate are selected such that collagen fibrillogenesis occurs within at least the outer portion of the polymer solution liquid sheet within the second flow conduit.

16. The method according to claim 8 wherein the polymer solution liquid sheet is cross-linked by one of photochemical cross-linking, ionic cross-linking, and thermal cross-linking.

17. The method according to claim 7 wherein the polymer sheet emerges from the fluidic device onto the surface of a liquid provided within a liquid reservoir, and wherein the polymer sheet is extracted and tensioned by passage thereof over a rotating cylinder partially submerged within said liquid without collecting the polymer sheet on the rotating cylinder.

18. The method according to claim 7 wherein the polymer sheet is collected on a rotating collection device.

19. The method according to claim 18 wherein the rotating collection device is one of a rotating mandrel and a rotating open frame.

20. The method according to claim 19 wherein the rotating collection device is translated during collection of the polymer sheet, such that the polymer sheet is collected in a spiral pattern without overlap.

21. The method according to claim 20 wherein the rotating collection device is configured to collect the polymer sheet with overlap.

22. The method according to claim 18 wherein a rotation axis of the rotating collection device is directed at angle relative to an extrusion direction of the polymer sheet.

23. The method according to claim 22 wherein the angle is between 45 degrees and 120 degrees.

24. The method according to claim 7 wherein the polymer sheet passes between a pair of counter-rotating cylinders after emerging from the fluidic device.

25. The method according to claim 24 wherein one or both of pair of counter-rotating cylinders has a surface pattern configured to induce crimping.

26. The method according to claim 24 wherein the polymer sheet is collected on a rotating collection device.

27. The method according to claim 26 wherein a tangential velocity of the rotating collection device is less than a tangential velocity of the pair of counter-rotating cylinders, such that the polymer sheet is crimped.

28. The method according to claim 26 wherein the rotating collection device is translated during collection of the polymer sheet, such that the polymer sheet is collected in a spiral pattern without overlap.

29. The method according to claim 7 wherein an extrusion velocity of the polymer sheet is $V_P$, a flow rate of the polymer solution is $Q_M$, a flow rate of the flow-confining solution is $Q_F$, the cross-sectional area of the second flow conduit is A, and the total velocity of the working fluids is $V_T=(Q_M+Q_F)/A$, and wherein $Q_M$, $Q_F$ and $V_P$ are controlled such that $V^*>2$, where $V^*=(V_P-V_T)/V_T$.

30. The method according to claim 29 wherein $Q_M$, $Q_F$ and $V_P$ are controlled such that $V^*>4$.

31. The method according to claim 7 wherein a thickness of said polymer sheet emerging from the second flow conduit is less than 100 microns.

32. The method according to claim 7 wherein a thickness of said polymer sheet emerging from the second flow conduit is less than 10 microns.

33. The method according to claim 7 wherein a thickness of said polymer sheet emerging from the second flow conduit is less than 3 microns.

34. A method of forming an anisotropic polymer material, the method comprising:
providing a fluidic device according to claim 1;
flowing the polymer solution into said polymer distribution fluidic network at a first controlled rate;
flowing the flow-confining solution into the first flow-confining distribution fluidic network and the second flow-confining distribution fluidic network at a second controlled rate;
the polymer solution being provided at a flow rate such that the combination of flow-focusing and shear generated within the second flow conduit reduces a thickness of the polymer sheet to a thickness less than 10 microns.

35. A system for forming an anisotropic polymer material, the system comprising:
a fluidic device according to claim 1;
a polymer solution dispensing device in flow communication with said proximal inlet of said polymer distribution fluidic network for providing the polymer liquid thereto at a first controlled flow rate;
a flow-confining solution dispensing device in flow communication with said proximal inlets of said first flow-confining distribution fluidic network and said second flow-confining distribution fluidic network for providing the flow-confining solution thereto at a second controlled flow rate; and
an extraction device configured to apply tension to a polymer sheet produced by the fluidic device as the polymer sheet emerges from the fluidic device.

36. The system according to claim 35 further comprising a liquid reservoir for receiving the polymer sheet on a liquid surface when the polymer sheet emerges from the fluidic device; and
a rotating cylinder configured to be partially submerged by a liquid provided within said liquid reservoir for applying tension to the polymer sheet when the polymer sheet is passed over said rotating cylinder.

37. The system according to claim 35 wherein said extraction device is a rotating collection device configured to collect the polymer sheet as the polymer sheet emerges from the fluidic device.

38. The system according to claim 37 wherein said rotating collection device is one of a rotating mandrel and a rotating open frame.

39. The system according to claim 37 wherein said rotating collection device is translated during collection of the polymer sheet, such that the polymer sheet is collected in a spiral pattern without overlap.

40. The system according to claim 39 wherein said fluidic device is further configured to deposit one or more additional layers onto the polymer sheet when the polymer sheet is retained on said rotating collection device, the system further comprising:
a rotating mandrel configured to collect the polymer sheet from said rotating collection device after deposition of the one or more additional layers.

41. The system according to claim 37 wherein a rotation axis of said rotating collection device is directed at a fixed or time-variable angle relative to an extrusion direction of the polymer sheet.

42. The system according to claim 41 wherein the angle is between 45 degrees and 120 degrees.

43. The system according to claim 35 wherein said extraction device is a pair of counter-rotating cylinders configured to receive the polymer sheet.

44. The system according to claim 43 wherein one or both of pair of counter-rotating cylinders has a surface pattern configured to induce crimping.

45. The system according to claim 43 further comprising a rotating collection device configured to collect the polymer sheet after the polymer sheet passes between said pair of counter-rotating cylinders.

46. The system according to claim 45 wherein said rotating collection device is configured to rotate a rotation rate that is less than a rotation rate of said pair of counter-rotating cylinders.

47. The system according to claim 46 wherein said rotating collection device is translated during collection of the polymer sheet, such that the polymer sheet is collected in a spiral pattern without overlap.

48. The system according to claim 35 wherein an extrusion velocity of the polymer sheet is $V_P$, a flow rate of the polymer solution is $Q_M$, a flow rate of the flow-confining solution is $Q_F$, the cross-sectional area of the second flow conduit is A, and the total velocity of the working fluids is $V_T=(Q_M+Q_F)/A$, and wherein $Q_M$, $Q_F$ and $V_P$ are controlled such that $V^*>2$, where $V^*=(V_P-V_T)/V_T$.

49. The system according to claim 48 wherein $Q_M$, $Q_F$ and $V_P$ are controlled such that $V^*>4$.

50. A system for forming an anisotropic polymer material, the system comprising:
- a fluidic device according to claim 1;
- a polymer solution dispensing device in flow communication with said proximal inlet of said polymer distribution fluidic network for providing the polymer liquid thereto at a first controlled flow rate;
- a flow-confining solution dispensing device in flow communication with said proximal inlets of said first flow-confining distribution fluidic network and said second flow-confining distribution fluidic network for providing the flow-confining solution thereto at a second controlled flow rate;
- wherein the first controlled flow rate is controlled such that the combination of flow-focusing and shear generated within the second flow conduit produces anisotropy with the polymer sheet.

* * * * *